United States Patent
Lever et al.

(10) Patent No.: US 11,034,654 B2
(45) Date of Patent: Jun. 15, 2021

(54) 2,3-DIHYDROISOINDOLE-1-CARBOXAMIDES USEFUL AS ROR-GAMMA MODULATORS

(71) Applicant: AstraZeneca AB, Södertälje (SE)

(72) Inventors: Sarah Lever, Södertälje (SE); Frank Narjes, Södertälje (SE); Roine Ingemar Olsson, Södertälje (SE); Stefan Von Berg, Södertälje (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 16/621,872

(22) PCT Filed: Jun. 13, 2018

(86) PCT No.: PCT/EP2018/065712
§ 371 (c)(1),
(2) Date: Dec. 12, 2019

(87) PCT Pub. No.: WO2018/229155
PCT Pub. Date: Dec. 20, 2018

(65) Prior Publication Data
US 2020/0115338 A1   Apr. 16, 2020

Related U.S. Application Data

(60) Provisional application No. 62/519,263, filed on Jun. 14, 2017.

(51) Int. Cl.
*C07D 209/44* (2006.01)
*C07D 403/12* (2006.01)
*C07D 405/12* (2006.01)
*C07D 413/12* (2006.01)
*A61K 45/06* (2006.01)

(52) U.S. Cl.
CPC ......... *C07D 209/44* (2013.01); *C07D 403/12* (2013.01); *C07D 405/12* (2013.01); *C07D 413/12* (2013.01); *A61K 45/06* (2013.01)

(58) Field of Classification Search
CPC .................................................. C07D 209/44
See application file for complete search history.

(56) References Cited

U.S. PATENT DOCUMENTS

| | | |
|---|---|---|
| 10,011,566 B2 | 7/2018 | Narjes et al. |
| 10,526,286 B2 | 1/2020 | Narjes et al. |
| 2005/0165218 A1 | 7/2005 | Beerli et al. |
| 2015/0218160 A1 | 8/2015 | Claremon et al. |
| 2016/0122318 A1 | 5/2016 | Claremon et al. |
| 2016/0122345 A1 | 5/2016 | Claremon et al. |
| 2017/0050974 A1 | 2/2017 | Yamamoto et al. |
| 2017/0107240 A1 | 4/2017 | Yamamoto et al. |
| 2017/0233390 A1 | 8/2017 | Schnute et al. |

FOREIGN PATENT DOCUMENTS

| | | |
|---|---|---|
| EP | 2076260 B1 | 7/2009 |
| EP | 3018123 A1 | 5/2016 |
| EP | 3018126 A1 | 5/2016 |
| JP | 2009051827 | 3/2009 |
| JP | 2009051828 | 3/2009 |
| WO | WO1996002537 A1 | 2/1996 |
| WO | WO1997027852 A1 | 8/1997 |
| WO | WO1999043672 A1 | 9/1999 |
| WO | WO2000054759 A2 | 9/2000 |
| WO | WO2001003705 A1 | 1/2001 |
| WO | WO2001085695 A1 | 11/2001 |
| WO | WO2002020463 A2 | 3/2002 |
| WO | WO2002046164 A1 | 6/2002 |
| WO | WO2002058690 A2 | 8/2002 |
| WO | WO2003041641 A2 | 5/2003 |
| WO | WO2003082198 A2 | 10/2003 |
| WO | WO2005009383 A2 | 2/2005 |
| WO | WO2005013946 A2 | 2/2005 |
| WO | WO2005055998 A1 | 6/2005 |
| WO | WO2006091862 A2 | 8/2006 |
| WO | WO2007055374 | 5/2007 |
| WO | WO2007058990 A2 | 5/2007 |
| WO | WO2007088999 A1 | 8/2007 |

(Continued)

OTHER PUBLICATIONS

Diabetes Mellitus (DM) online; retrieved from the internet on May 29, 2017; URL; http://www.merckmanuals.com/professional/endocrine-and-metabolic-disorder/diabetes-mellitus-dm.*
Bartlett et al., Targeting the IL-17-T$_H$17, Nature Reviews, 2015, pp. 11-12, vol. 14.
CAS Registry No. 1009689-67-1, Entered STN Mar. 23, 2008, CHEMCATS (Chemical Catalogs Online).
CAS Registry No. 1030916-68-7, Entered STN Jun. 26, 2008, CHEMCATS (Chemical Catalogs Online).
CAS Registry No. 1792962-73-2, Entered STN Jul. 1, 2015, CHEMCATS (Chemical Catalogs Online).
Cheng et al., Heteroaryl substituted bis-trifluoromethyl carbinols as malonyl-CoA decarboxylase inhibitors, Bioorganic & Medicinal Chemistry Letters, 2006, pp. 3484-3488, vol. 16.

(Continued)

*Primary Examiner* — Shawquia Jackson

(57) ABSTRACT

The present specification provides a compound of formula (I):

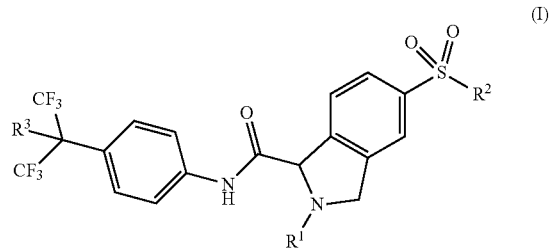

or a pharmaceutically acceptable salt thereof; a process for preparing such a compound; and to the use of such a compound in the treatment of an RORγ and/or RORγt mediated disease state.

12 Claims, No Drawings

Specification includes a Sequence Listing.

(56) References Cited

FOREIGN PATENT DOCUMENTS

| | | |
|---|---|---|
| WO | WO2007106525 A1 | 9/2007 |
| WO | WO2007146712 A2 | 12/2007 |
| WO | WO2008008020 A1 | 1/2008 |
| WO | WO2008008022 A1 | 1/2008 |
| WO | WO2011115892 A1 | 9/2011 |
| WO | WO2012027965 A1 | 3/2012 |
| WO | WO2012028100 A1 | 3/2012 |
| WO | WO2012100732 A1 | 8/2012 |
| WO | WO2012100734 A1 | 8/2012 |
| WO | WO2012106995 A1 | 8/2012 |
| WO | WO2012158784 A2 | 11/2012 |
| WO | WO2013029338 A1 | 3/2013 |
| WO | WO2013100027 A1 | 7/2013 |
| WO | WO2013120835 A1 | 8/2013 |
| WO | WO2013159095 A1 | 10/2013 |
| WO | WO2013166013 A1 | 11/2013 |
| WO | WO2013166015 A1 | 11/2013 |
| WO | WO2013171729 A2 | 11/2013 |
| WO | WO2014125426 A1 | 8/2014 |
| WO | WO2014165816 A1 | 10/2014 |
| WO | WO2014179564 A1 | 11/2014 |
| WO | WO2015017335 A1 | 2/2015 |
| WO | WO2015035032 A1 | 3/2015 |
| WO | WO2015082533 A1 | 6/2015 |
| WO | WO2015083130 A1 | 6/2015 |
| WO | WO2015101928 A1 | 7/2015 |
| WO | WO2015116904 A1 | 8/2015 |
| WO | WO2015129853 A1 | 9/2015 |
| WO | WO2015145371 A1 | 10/2015 |
| WO | WO2015159233 A1 | 10/2015 |
| WO | WO2015160654 A1 | 10/2015 |
| WO | WO2016002968 A1 | 1/2016 |
| WO | WO2016020288 A1 | 2/2016 |
| WO | WO2016046755 A1 | 3/2016 |
| WO | WO2016061160 A1 | 4/2016 |
| WO | WO2016073633 A1 | 5/2016 |
| WO | WO2016176399 A1 | 11/2016 |
| WO | WO2016185342 A1 | 11/2016 |
| WO | WO2016193452 A1 | 12/2016 |
| WO | WO2016193459 A1 | 12/2016 |
| WO | WO2016193461 A1 | 12/2016 |
| WO | WO2016193468 A1 | 12/2016 |
| WO | WO2016193470 A1 | 12/2016 |
| WO | WO2017010399 A1 | 1/2017 |
| WO | WO2017024018 A1 | 2/2017 |
| WO | WO2017058831 A1 | 4/2017 |
| WO | WO2017102784 A1 | 6/2017 |

OTHER PUBLICATIONS

Fauber et al., Journal of Medicinal Chemistry 2014 57:5871-5892.
Gaffen et al., IL-23-IL-17 immune axis: Discovery, Mechanistic Understanding, and Clinical Testing, Nat. Rev. Immunol., 2014, pp. 585-600, vol. 14 (9).
He et al., RORγt, a Novel Isoform of an Orphan Receptor, Negatively Regulates Fas Ligand Expression and IL-2 Production in T Cells, Immunity, 1998, pp. 797-806, vol. 9 (6).
Ivanov et al., The Orphan Nuclear Receptor RORgt Directs the Differentiation Program of Proinflammatory IL-17+ T Helper Cells, Cell, Sep. 22, 2006, pp. 1121-1133, vol. 126.
Jetten et al., The RoR Nuclear Orphan Receptor Subfamily: Critical Regulators of Multiple Biological Processes, Progress in Nucleic Acid Research and Molecular Biology, 2001, pp. 205-247, vol. 69.
Kamenecka et al., Med. Chem. Comm. 2013 4:764-776.
Morán-Ramallal, Dynamic Kinetic Resolution of 1,3-Dihydro-2H-isoindole-1-carboxylic Acid Methyl Ester: Asymmetric Transformations toward Isoindoline Carbamates, Organic Letters, 2012, pp. 1696-1699, vol. 14 (7).
Narjes et al., Potent and Orally Bioavailable Inverse Agonists of RORγt Resulting from Structure-Based Design, J. Med. Chem., 2018, pp. 7796-7813, vol. 61.
Narjes, The discovery of AZD0284, Symposium presentation, Sep. 13, 2017, 1-31, Cambridge, United Kingdom.
Narjes, "The discovery of AZD0284, an inverse agonist of the nuclear receptor RORγ," American Chemical Society, 2017 Drug Design and Delivery Symposium Webinar, Oct. 26, 2017 (Webinar Slides).
Narjes, "The discovery of AZD0284, an inverse agonist of the nuclear receptor RORγ," American Chemical Society, 2017 Drug Design and Delivery Symposium Webinar, Oct. 26, 2017 (Slides posted at https://www.acs.org/content/dam/acsorg/events/drug-discovery/slides/2017-10-26-ddds9-psoriasis-public-slides.pdf).
Nishimura, Small Molecule Disruptors of the Glucokinase—Glucokinase Regulatory Protein Interaction: 3. Structure—Activity Relationships within the Aryl Carbinol Region of the N-Arylsulfonamido-N'-arylpiperazine Series, J. Med. Chem., 2014, pp. 3094-3116, vol. 57.
Wang et al., ACS Medicinal Chemistry Letters 2015 6:787-792.
Wang et al., Bioorganic and Medicinal Chemistry 2015 23:5293-5302.
Wilke, Deciphering the role of Th17 cells in human disease, Trends Immunol., 2011, pp. 603-611, vol. 32 (12).
Zhang et al., Acta Pharmacologica Sinica 2015 36:71-87.
Interational Search Report and Written Opinion dated Mar. 14, 2017 for Application No. PCT/EP2016/080885.
Mease, Philip J., Inhibition of interleukin-17, interleukin-23 and the TH17 cell pathway in the treatment of psoriatic arthritis and psoriasis, Curr. Opin. Rheumatol., 2015, 27(2):127-133.
Cosmi, et al., Th17 regulating lower airway disease, Curr. Opin. Allergy Clin. Immunol., 2016, 16(1):1-6.
Von Berg, et al., Discovery of Potent and Orally Bioavailable Inverse Agonists of the Retinoic Acid Receptor-Related Orphan Receptor C2, ACS Med. Chem. Lett., 2019, 10(6):972-977.
Bronner et al., "ROR[gamma] antagonists and inverse agonists: a patent review", Expert Opinion on Therapeutic Patents, vol. 27, No. 1, Jan. 2, 2017, pp. 101-112.
Psoriasis [online], retrieved from the internet on Nov. 26, 2017; URL https://medicinenet.com/psoriasis/article.htm.
Diabetes Mellitus (DM) online; retrieved from the internet on May 29, 2017; URL; http://www.merckmanuals.com/professional/endocrine-and-metabolic-disorders/diabetes-mellitus-dm.
International Search Report and Written Opinion dated Aug. 24, 2018 for Application No. PCT/EP2018/065712.

* cited by examiner

2,3-DIHYDROISOINDOLE-1-CARBOXAMIDES USEFUL AS ROR-GAMMA MODULATORS

This specification relates to arylamide compounds having pharmaceutical activity, to processes for preparing such compounds, to pharmaceutical compositions comprising such compounds and to the use of such compounds as active therapeutic agents.

Retinoic acid receptor-related orphan receptors (RORs) are a family of transcription factors which belong to the nuclear receptor superfamily. The family is comprised of three genes, RORA, RORB, and RORC, all of which express more than one isoform of the protein (Jetten, A M; Kurebayashi, S; Ueda, E. (2006) Prog. Nucleic Acid Res. Mol. Biol. 69:205-47). RORC (also known as RORγ or NR1F3) is translated into two major protein isoforms which share most of the amino acid sequence, including the ligand binding domain, but differ 21 amino acids in length in the N-terminal end. The two isoforms are differentially expressed. The longer form (RORγ) is found in many tissues such as liver, kidney, muscle and some cells of hematopoietic origin whereas the shorter form (RORγt) is expressed in the thymus and cells of the immune system (He, Y W; Deftos, M L; Ojala, E W; Bevan, M J (1998) Immunity 9(6):797-806). RORγt has been shown to be required for differentiation and function of Th17 cells and coordinates the expression of IL17 in many immune cells (Ivanov, I I; McKenzie, B S; Zhou, L; Littman, D R et al. (2006) Cell 126:1121-1133). Th17 cells are a subset of T helper cells that produce IL17, IL22, and other cytokines. They attain their Th17 phenotype through local exposure to a combination of cytokines such as TGFβ, IL1β and IL23. The mediators and transcription factors that are required for their differentiation, polarization and effector function are referred to as the Th17 axis, and the Th17 axis includes other cell types which produce the same cytokines (and corresponding receptors), such as innate lymphoid cells (ILCs) and γδ T cells.

The Th17 axis of biological processes has been implicated in the pathology of many human diseases with an immune component or autoimmune pathology, such as psoriasis, ankylosing spondylitis, psoriatic arthritis, asthma, chronic obstructive pulmonary disease, ulcerative colitis, Crohn's disease, multiple sclerosis, inflammatory bowel disease, rheumatoid arthritis, graft versus host disease, systemic lupus erythematosus, lupus nephritis, insulin dependent diabetes type I, and also in cancer (Wilke C M, Bishop K, Fox D, Zou W (2011) Trends Immunol. 32(12):603-11; Bartlett, H S; Million, R P (2015) Nat. Rev. Drug Discovery 14:11-12). Many of these diseases share genetic associations to genes contained in the Th17 axis (Gaffen S L, Jain R, Garg A V, Cua D J (2014) Nat. Rev. Immunol. 14(9):585-600).

RORγt is central to the Th17 axis since it is required for the function of Th17 cells and governs cytokine production and related biological processes in many other cell types. Due to the central role of RORγt it is desirable to regulate RORγt activity as a means of treatment of diseases where the Th17 axis is perturbed. Accordingly there is a need for new therapeutic agents which modulate RORγt.

Briefly, this specification describes, in part, a compound of formula (I):

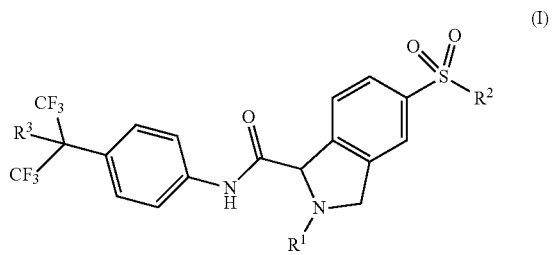

wherein:

$R^1$ is H, (CO)$R^4$ or (CO)NH—$C_{1-6}$ alkyl;

$R^2$ is $C_{1-6}$ alkyl or $CH_2$-cyclopropyl;

$R^3$ is $C_{1-6}$ alkyl, $C_{1-6}$ alkoxy, CN, heterocycloalkyl, heteroaryl, $NR^5R^6$, $CH_2$(CO)—O—$C_{1-6}$ alkyl, $CH_2$(CO)$NR^7R^8$, wherein said $C_{1-6}$ alkyl is further optionally substituted with one substituent selected from OH, halo, CN, heteroaryl, or NH(CO)Me, and wherein each heteroaryl is further optionally substituted with one methyl group;

$R^4$ is:
H;
$C_{1-6}$ alkyl optionally substituted with one substituent selected from OH, $C_{1-6}$ alkoxy, COOH or $NH_2$;
$C_{3-7}$ cycloalkyl optionally substituted with $C_{1-6}$ alkoxy; or
$C_{1-6}$ alkoxy;

$R^5$ is H or $C_{1-6}$ alkyl;

$R^6$ is $C_{1-6}$ alkyl or heterocycloalkyl, wherein said $C_{1-6}$ alkyl is further optionally substituted with one substituent selected from OH, $C_{1-6}$ alkoxy, $C_{3-7}$ cycloalkyl (itself optionally substituted by $C_{1-6}$ alkoxy) or $SO_2Me$;

$R^7$ is H or $C_{1-6}$ alkyl;

$R^8$ is $C_{3-7}$ cycloalkyl or $C_{1-6}$ alkyl wherein said $C_{1-6}$ alkyl is further optionally substituted with halo; or $R^7$ and $R^8$ together with the nitrogen atom to which they are both attached form a heterocycloalkyl (itself optionally substituted with one or two substituents selected from $C_{1-6}$ alkyl or halo);

or a pharmaceutically acceptable salt thereof.

This specification also describes, in part, pharmaceutical compositions which comprise a compound of formula (I), or a pharmaceutically acceptable salt thereof, and one or more pharmaceutically acceptable excipients.

This specification also describes, in part, a compound of formula (I), or a pharmaceutically acceptable salt thereof, for use in therapy.

This specification also describes, in part, a compound of formula (I), or a pharmaceutically acceptable salt thereof, for the treatment or prevention of an RORγ and/or RORγt mediated disease state.

This specification also describes, in part, the use of a compound of formula (I), or a pharmaceutically acceptable salt thereof, in the manufacture of a medicament for use in the treatment or prevention of an RORγ and/or RORγt mediated disease state.

This specification also describes, in part, a method of treating or preventing an RORγ and/or RORγt mediated disease state in a mammal suffering from, or at risk of, said disease, which comprises administering to a mammal in need of such treatment a therapeutically effective amount of a compound of formula (I), or a pharmaceutically acceptable salt thereof.

Further aspects of the specification will be apparent to one skilled in the art from reading this specification.

The compounds of the specification may exist in salt-form or in non-salt form (i.e. as a free base), and the present specification covers both salt forms and non-salt forms. Compounds described in this specification may form acid addition salts or base addition salts. In general, an acid addition salt can be prepared using various inorganic or organic acids. Such salts can typically be formed by, for example, mixing the compound with an acid (e.g. a stoichiometric amount of an acid) using various methods known in the art. This mixing may occur in water, an organic solvent (e.g. ether, ethyl acetate, ethanol, methanol, isopropanol, or acetonitrile), or an aqueous/organic mixture. In another aspect of the specification acid addition salts are, for example, trifluoroacetate, formate, acetate or hydrochloric. In general, a base addition salt can be prepared using various inorganic or organic bases, for example an alkali or alkaline earth metal salt such as a sodium, calcium or magnesium salt, or other metal salts, such as potassium or zinc, or an ammonium salt, or a salt with an organic base such as methylamine, dimethylamine, trimethylamine, piperidine or morpholine. The skilled person will be aware of the general principles and techniques of preparing pharmaceutical salts, such as those described in, for example, Berge et al., *J. Pharm. Sci.*, 66, 1-19 (1977).

Compounds and salts described in this specification include one or more chiral (i.e. asymmetric) centres. To the extent a structure or chemical name in this specification does not indicate the chirality, the structure or name is intended to encompass any single stereoisomer (i.e. any single chiral isomer) corresponding to that structure or name, as well as any mixture of stereoisomers (e.g. a racemate). For example, a single stereoisomer could be obtained by isolating it from a mixture of isomers (e.g. a racemate) using, for example, chiral chromatographic separation. For instance, a single stereoisomer could be obtained through direct synthesis from, for example, an enantiomerically pure starting material.

A particular enantiomer of a compound described herein may be more active than the other enantiomer of the same compound.

According to one embodiment there is provided a compound of formula (I), or a pharmaceutically acceptable salt thereof, which is a single enantiomer being in an enantiomeric excess (% ee) of ≥95, ≥98% or ≥99%. Conveniently, the single enantiomer is present in an enantiomeric excess (% ee) of ≥99%.

According to another embodiment there is provided a pharmaceutical composition, which comprises a compound of formula (I), which is a single enantiomer being in an enantiomeric excess (% ee) of ≥95, ≥98% or ≥99% or a pharmaceutically acceptable salt thereof, in association with one or more pharmaceutically acceptable excipients. Conveniently, the single enantiomer is present in an enantiomeric excess (% ee) of ≥99%.

When in solid crystalline form a compound of formula (I) can be in the form of a co-crystal with another chemical entity and the specification encompasses all such co-crystals.

The compounds of the specification may exist as a solvate (such as a hydrate) as well as unsolvated forms, and the present specification covers all such solvates.

Compounds and salts described in this specification may exist in various tautomeric forms and the specification encompasses all such tautomeric forms. "Tautomers" are structural isomers that exist in equilibrium resulting from the migration of a hydrogen atom.

Compounds and salts described in this specification may be isotopically-labeled (or "radio-labeled"). In that instance, one or more atoms are replaced by an atom having an atomic mass or mass number different from the atomic mass or mass number typically found in nature. The specification encompasses isotopically-labelled forms of compounds disclosed herein. Examples of isotopes that may be incorporated include $^2$H (also written as "D" for deuterium), $^3$H (also written as "T" for tritium), $^{11}$C, $^{13}$C, $^{14}$C, $^{13}$N, $^{15}$N, $^{15}$O, $^{17}$O, $^{18}$O, $^{18}$F and $^{36}$Cl. The isotope that is used will depend on the specific application of that radio-labeled derivative. For example, for in vitro receptor labeling and competition assays, $^3$H or $^{14}$C are often useful. For radio-imaging applications, $^{11}$C is often useful. In some embodiments, the radionuclide is $^3$H. In some embodiments, the radionuclide is $^{14}$C. In some embodiments, the radionuclide is $^{11}$C.

Unless otherwise stated, halo is selected from chloro (Cl), fluoro (F), bromo (Br) and iodo (I), such as fluoro.

Cycloalkyl is a non-aromatic carbocyclic ring. The carbocyclic ring may be saturated or unsaturated and may be bridged or unbridged. $C_{3-7}$ cycloalkyl is any such carbocyclic ring containing 3 to 7 carbon atoms. An example of $C_{3-7}$ cycloalkyl is a saturated, non-aromatic carbocyclic ring containing 3 to 7 carbon atoms. Examples of suitable cycloalkyl groups are cyclopropyl, cyclobutyl, cyclopentyl, cyclohexyl and cycloheptyl, such as cyclopropyl.

Heterocycloalkyl is a 3 to 9 membered non-aromatic, mono- or bi-cyclic ring comprising one or two heteroatoms independently selected from nitrogen, oxygen or sulphur; or an N-oxide thereof, or an S-oxide or S-dioxide thereof. The ring may be saturated or unsaturated, and may be bridged or unbridged. An example of heterocycloalkyl is a saturated 4 to 6 membered non-aromatic, mono-cyclic ring comprising one or two heteroatoms independently selected from nitrogen or oxygen. Examples of suitable heterocycloalkyl groups include azetidinyl, oxetanyl, tetrahydrofuranyl, pyrrolidinyl, tetrahydropyranyl, piperidinyl, morpholinyl, thiomorpholinyl, and piperazinyl, such as azetidinyl, oxetanyl, pyrrolidinyl, tetrahydropyranyl or morpholinyl.

Aryl is an aromatic ring containing 6 or 10 carbon atoms. Examples of suitable aryl groups include phenyl and naphthyl, such as phenyl.

Heteroaryl is a 5 to 6 membered aromatic, mono- or bi-cyclic ring comprising 3 to 4 heteroatoms independently selected from nitrogen, oxygen and sulphur. An example of heteroaryl is an aromatic 5 membered, mono-cyclic ring comprising three or four heteroatoms independently selected from nitrogen or oxygen. Examples of suitable heteroaryl groups include triazolyl, furazanyl, oxadiazolyl, thiadiazolyl, dithiazolyl or tetrazolyl, such as triazolyl, oxadiazolyl and tetrazolyl. For the avoidance of doubt, optional substituents on the heterocyloaryl ring may be linked via either a carbon atom or a heteroatom.

Unless otherwise stated alkyl and alkoxy groups containing the requisite number of carbon atoms can be branched or unbranched. Examples of suitable $C_{1-6}$ alkyl groups include methyl (Me), ethyl (Et), n-propyl, i-propyl, n-butyl, sec-butyl, i-butyl, t-butyl, n-pentyl, i-pentyl, neo-pentyl, n-hexyl and i-hexyl, such as methyl, ethyl, n-propyl, i-propyl, and t-butyl. Examples of suitable $C_{1-6}$ alkoxy groups include methoxy, ethoxy, n-propoxy, i-propoxy, n-butoxy, sec-butoxy, t-butoxy, n-pentoxy, i-pentoxy, n-hexoxy, i-hexoxy, methoxyethyl, methoxypropyl, ethoxyethyl and methoxybutyl, such as methoxy, and i-propoxy.

In one embodiment R¹ is (CO)R⁴ or (CO)NH—C₁₋₆ alkyl.
In another embodiment R¹ is (CO)R⁴.
In one embodiment R² is unsubstituted C₁₋₆ alkyl.
In one embodiment R² is methyl or ethyl.
In one embodiment R² is methyl.
In one embodiment R² is CH₂-cyclopropyl.
In one embodiment R³ is CN, C₁₋₆ alkoxy or heterocycloalkyl.
In another embodiment R³ is CN, C₁₋₆ alkoxy or a saturated 4 to 6-membered non-aromatic, unsubstituted, mono-cyclic ring comprising one or two heteroatoms independently selected from nitrogen or oxygen.
In another embodiment R³ is CN, C₁₋₆ alkoxy or an unsubstituted pyrrolidinyl.
In another embodiment R³ is CN, methoxy or an unsubstituted pyrrolidinyl.
In another embodiment R³ is CN.
In another embodiment R³ is methoxy.
In another embodiment R³ is unsubstituted pyrrolidinyl.
In another embodiment R³ is C₁₋₆ alkyl (substituted with OH, halo, CN, heteroaryl optionally substituted with one methyl group, NH(CO)Me), CN, NR⁵R⁶, CH₂(CO)—O—C₁₋₆ alkyl (such as CH₂(CO)—O-Me, CH₂(CO)—O-Et, CH₂(CO)—O-iPr, CH₂(CO)—O-tBu) or CH₂(CO)NR⁷R⁸).
In another embodiment R³ is C₁₋₆ alkyl (substituted with OH, halo, CN, oxadiazole optionally substituted with one methyl, NH(CO)Me), CN, NR⁵R⁶, CH₂(CO)—O—C₁₋₆ alkyl (such as CH₂(CO)—O-Me, CH₂(CO)—O-Et, CH₂(CO)—O-iPr, CH₂(CO)—O-tBu) or CH₂(CO)NR⁷R⁸).
In another embodiment R³ is CN, NR⁵R⁶, CH₂(CO)—O—C₁₋₆ alkyl (such as CH₂(CO)—O-Me, CH₂(CO)—O-Et, CH₂(CO)—O-iPr, CH₂(CO)—O-tBu) or CH₂(CO)NR⁷R⁸).
In another embodiment R³ is CN or NR⁵R⁶.
In another embodiment R³ is heterocycloalkyl.
In another embodiment R³ is a saturated 4 to 6 membered non-aromatic, unsubstituted, mono-cyclic ring comprising one or two heteroatoms independently selected from nitrogen or oxygen.
In another embodiment R³ is pyrrolidinyl or morpholinyl.
In another embodiment R³ is heteroaryl optionally substituted by methyl.
In another embodiment R³ is an aromatic 5 membered, mono-cyclic ring comprising three or four nitrogen heteroatoms optionally substituted by methyl.
In another embodiment R³ is triazole or tetrazole optionally substituted by methyl.
In one embodiment R⁴ is C₁₋₆ alkyl optionally substituted with OH, C₁₋₆ alkoxy, COOH, NH₂ or C₁₋₆ alkoxy (such as methoxy).
In one embodiment R⁴ is C₁₋₆ alkyl (such as methyl) optionally substituted with OH or C₁₋₆ alkoxy (such as methoxy).
In one embodiment R⁴ is unsubstituted methyl or methyl substituted with OH or methoxy.
In one embodiment R⁴ is unsubstituted methyl.
In one embodiment R⁴ is methyl substituted with OH.
In one embodiment R⁴ is methoxy.
In one embodiment R⁴ is C₁₋₆ alkyl (such as methyl or ethyl) optionally substituted with OH, C₁₋₆ alkoxy, COOH, NH₂.
In one embodiment R⁴ is unsubstituted C₁₋₆ alkyl.
In one embodiment R⁵ is H.
In one embodiment R⁵ is methyl.
In one embodiment R⁶ is C₁₋₆ alkyl optionally substituted with one substituent independently selected from the group consisting of OH, C₁₋₆ alkoxy, C₃₋₇ cycloalkyl (itself optionally substituted by C₁₋₆ alkoxy) and SO₂Me.

In another embodiment R⁶ is C₁₋₆ alkyl (such as methyl, ethyl or n-propyl) optionally substituted with one substituent independently selected from the group consisting of OH, C₁₋₆ alkoxy, C₃₋₇ cycloalkyl (itself optionally substituted by C₁₋₆ alkoxy) and SO₂Me.
In another embodiment R⁶ is -Me,

—CH₂CH₂OMe, —CH₂CH₂OH, —CH₂CH₂SO₂Me, —CH₂CH₂O'Pr, —CH₂CH₂Me or —CH₂CH₂CH₂SO₂Me.
In another embodiment R⁶ is a saturated 4 to 6 membered non-aromatic, unsubstituted, mono-cyclic ring comprising one oxygen atom.
In another embodiment R⁶ is unsubstituted oxetanyl or unsubstituted tetrahydropyranyl.
In one embodiment R⁷ is H.
In another embodiment R⁷ is methyl.
In one embodiment R⁸ is C₁₋₆ alkyl (such as methyl, ethyl or t-butyl) optionally substituted with halo (such as fluoro).
In another embodiment R⁸ is unsubstituted methyl, ethyl substituted with fluoro or unsubstituted t-butyl.
In one embodiment R⁷ and R⁸ together with the nitrogen atom to which they are both attached form a saturated 4-membered non-aromatic, mono-cyclic ring comprising one nitrogen heteroatom wherein the ring is di-substituted with a single methyl and a single halo.
In one embodiment R⁷ and R⁸ together form 3-fluoro-3-methylazetidin-1-yl.
In a further embodiment, there is provided a compound of formula (I) or a pharmaceutically acceptable salt thereof, wherein:
R¹ is (CO)R⁴ or (CO)NH—C₁₋₆ alkyl;
R² is C₁₋₆ alkyl or CH₂-cyclopropyl;
R³ is C₁₋₆ alkoxy, CN or heterocycloalkyl; and
R⁴ is:
C₁₋₆ alkyl optionally substituted with OH; or
C₁₋₆ alkoxy.
In another embodiment, there is provided the compound of formula (I) which exhibits R-stereochemistry at the carbon atom marked with an asterisk as shown below:

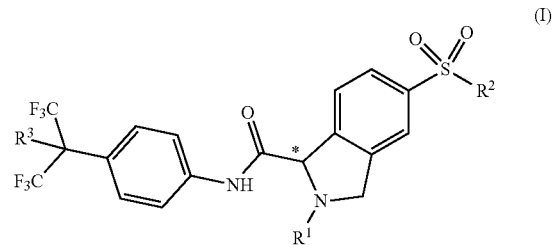

(I)

or a pharmaceutically acceptable salt thereof.
Where any embodiment within this specification includes a group which is said to be "optionally substituted", then unless otherwise stated the said group may be unsubstituted or may be substituted with 1, 2 or 3 substituents (such as 1 or 2 substituents, for example 1 substituent) independently selected from the list of substituents provided. For the avoidance of doubt a further embodiment will include that embodiment wherein the said group is unsubstituted.

Where any embodiment within this specification includes a sub-selection of a smaller group (using the words "such as" or "for example"), then for the avoidance of doubt each sub-selected group represents an additional embodiment.

An example of a compound of the specification is:

N-[4-(2-Cyano-1,1,1,3,3,3-hexafluoropropan-2-yl)phenyl]-5-(methylsulfonyl)-2,3-dihydro-1H-isoindole-1-carboxamide;

2-Acetyl-N-[4-(2-cyano-1,1,1,3,3,3-hexafluoropropan-2-yl)phenyl]-5-(methylsulfonyl)-2,3-dihydro-1H-isoindole-1-carboxamide;

N-[4-(2-Cyano-1,1,1,3,3,3-hexafluoropropan-2-yl)phenyl]-2-[(1-methoxycyclopropyl)carbonyl]-5-(methylsulfonyl)-2,3-dihydro-1H-isoindole-1-carboxamide;

$N^1$-[4-(2-Cyano-1,1,1,3,3,3-hexafluoropropan-2-yl)phenyl]-$N^2$-methyl-5-(methylsulfonyl)-1,3-dihydro-2H-isoindole-1,2-dicarboxamide;

N-[4-(2-Cyano-1,1,1,3,3,3-hexafluoropropan-2-yl)phenyl]-2-(hydroxyacetyl)-5-(methylsulfonyl)-2,3-dihydro-1H-isoindole-1-carboxamide;

N-[4-(2-Cyano-1,1,1,3,3,3-hexafluoropropan-2-yl)phenyl]-2-formyl-5-(methylsulfonyl)-2,3-dihydro-1H-isoindole-1-carboxamide;

Methyl 1-{[4-(2-cyano-1,1,1,3,3,3-hexafluoropropan-2-yl)phenyl]carbamoyl}-5-(methylsulfonyl)-1,3-dihydro-2H-isoindole-2-carboxylate;

N-[4-(2-Cyano-1,1,1,3,3,3-hexafluoropropan-2-yl)phenyl]-2-(methoxyacetyl)-5-(methylsulfonyl)-2,3-dihydro-1H-isoindole-1-carboxamide;

4-[1-{[4-(2-Cyano-1,1,1,3,3,3-hexafluoropropan-2-yl)phenyl]carbamoyl}-5-(methylsulfonyl)-1,3-dihydro-2H-isoindol-2-yl]-4-oxobutanoic acid;

N-[4-(2-Cyano-1,1,1,3,3,3-hexafluoropropan-2-yl)phenyl]-2-glycyl-5-(methylsulfonyl)-2,3-dihydro-1H-isoindole-1-carboxamide;

2-(3-Aminopropanoyl)-N-[4-[1-cyano-2,2,2-trifluoro-1-(trifluoromethyl)ethyl]phenyl]-5-methylsulfonyl-isoindoline-1-carboxamide;

N-[4-(2-Cyano-1,1,1,3,3,3-hexafluoropropan-2-yl)phenyl]-5-[(cyclopropylmethyl)sulfonyl]-2,3-dihydro-1H-isoindole-1-carboxamide;

2-Acetyl-N-[4-(2-cyano-1,1,1,3,3,3-hexafluoropropan-2-yl)phenyl]-5-[(cyclopropylmethyl)sulfonyl]-2,3-dihydro-1H-isoindole-1-carboxamide;

2-Acetyl-N-[4-(2-cyano-1,1,1,3,3,3-hexafluoropropan-2-yl)phenyl]-5-(ethylsulfonyl)-2,3-dihydro-1H-isoindole-1-carboxamide;

2-Acetyl-N-{4-[1,1,1,3,3,3-hexafluoro-2-(pyrrolidin-1-yl)propan-2-yl]phenyl}-5-(methylsulfonyl)-2,3-dihydro-1H-isoindole-1-carboxamide;

2-Acetyl-N-{4-[1,1,1,3,3,3-hexafluoro-2-(propylamino)propan-2-yl]phenyl}-5-(methylsulfonyl)-2,3-dihydro-1H-isoindole-1-carboxamide;

2-Acetyl-N-(4-{1,1,1,3,3,3-hexafluoro-2-[(2-methoxyethyl)amino]propan-2-yl}phenyl)-5-(methylsulfonyl)-2,3-dihydro-1H-isoindole-1-carboxamide;

2-Acetyl-N-[4-(1,1,1,3,3,3-hexafluoro-2-{[(1-methoxycyclopropyl)methyl]amino}propan-2-yl)phenyl]-5-(methylsulfonyl)-2,3-dihydro-1H-isoindole-1-carboxamide;

2-Acetyl-N-{4-[1,1,1,3,3,3-hexafluoro-2-(oxetan-3-ylamino)propan-2-yl]phenyl}-5-(methylsulfonyl)-2,3-dihydro-1H-isoindole-1-carboxamide;

2-Acetyl-N-{4-[1,1,1,3,3,3-hexafluoro-2-(tetrahydro-2H-pyran-4-ylamino)propan-2-yl]phenyl}-5-(methylsulfonyl)-2,3-dihydro-1H-isoindole-1-carboxamide;

2-Acetyl-N-(4-{1,1,1,3,3,3-hexafluoro-2-[(2-hydroxyethyl)amino]propan-2-yl}phenyl)-5-(methylsulfonyl)-2,3-dihydro-1H-isoindole-1-carboxamide;

2-Acetyl-N-[4-(1,1,1,3,3,3-hexafluoro-2-{[3-(methylsulfonyl)propyl]amino}propan-2-yl)phenyl]-5-(methylsulfonyl)-2,3-dihydro-1H-isoindole-1-carboxamide;

2-Acetyl-N-{4-[1,1,1,3,3,3-hexafluoro-2-(morpholin-4-yl)propan-2-yl]phenyl}-5-(methylsulfonyl)-2,3-dihydro-1H-isoindole-1-carboxamide;

2-Acetyl-N-{4-[1,1,1,3,3,3-hexafluoro-2-(methylamino)propan-2-yl]phenyl}-5-(methylsulfonyl)-2,3-dihydro-1H-isoindole-1-carboxamide;

2-Acetyl-N-{4-[2-(dimethylamino)-1,1,1,3,3,3-hexafluoropropan-2-yl]phenyl}-5-(methylsulfonyl)-2,3-dihydro-1H-isoindole-1-carboxamide;

2-Acetyl-N-[4-(1,1,1,3,3,3-hexafluoro-2-{[2-(methylsulfonyl)ethyl]amino}propan-2-yl)phenyl]-5-(methylsulfonyl)-2,3-dihydro-1H-isoindole-1-carboxamide;

2-Acetyl-N-[4-(1,1,1,3,3,3-hexafluoro-2-{[2-(propan-2-yloxy)ethyl]amino}propan-2-yl)phenyl]-5-(methylsulfonyl)-2,3-dihydro-1H-isoindole-1-carboxamide;

2-Acetyl-N-[4-(1,1,1,3,3,3-hexafluoro-2-methoxypropan-2-yl)phenyl]-5-(methylsulfonyl)-2,3-dihydro-1H-isoindole-1-carboxamide;

2-Acetyl-N-{4-[1,1,1,3,3,3-hexafluoro-2-(1H-1,2,3-triazol-1-yl)propan-2-yl]phenyl}-5-(methylsulfonyl)-2,3-dihydro-1H-isoindole-1-carboxamide;

2-Acetyl-N-{4-[1,1,1,3,3,3-hexafluoro-2-(2-methyl-2H-tetrazol-5-yl)propan-2-yl]phenyl}-5-(methylsulfonyl)-2,3-dihydro-1H-isoindole-1-carboxamide;

Methyl 4,4,4-trifluoro-3-[4-[(5-methylsulfonylisoindoline-1-carbonyl)amino]phenyl]-3-(trifluoromethyl)butanoate;

Methyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate;

2-Acetyl-5-(methylsulfonyl)-N-{4-[1,1,1-trifluoro-4-hydroxy-2-(trifluoromethyl)butan-2-yl]phenyl}-2,3-dihydro-1H-isoindole-1-carboxamide;

2-Acetyl-N-(4-{1,1,1,3,3,3-hexafluoro-2-[(3-methyl-1,2,4-oxadiazol-5-yl)methyl]propan-2-yl}phenyl)-5-(methylsulfonyl)-2,3-dihydro-1H-isoindole-1-carboxamide;

2-Acetyl-5-(methylsulfonyl)-N-{4-[1,1,1,4-tetrafluoro-2-(trifluoromethyl)butan-2-yl]phenyl}-2,3-dihydro-1H-isoindole-1-carboxamide;

2-Acetyl-N-{4-[2-(cyanomethyl)-1,1,1,3,3,3-hexafluoropropan-2-yl]phenyl}-5-(methylsulfonyl)-2,3-dihydro-1H-isoindole-1-carboxamide;

Ethyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate;

2-Acetyl-N-{4-[4-(cyclopropylamino)-1,1,1-trifluoro-4-oxo-2-(trifluoromethyl)butan-2-yl]phenyl}-5-(methylsulfonyl)-2,3-dihydro-1H-isoindole-1-carboxamide;

2-Acetyl-5-(methylsulfonyl)-N-{4-[1,1,1-trifluoro-4-(3-fluoro-3-methylazetidin-1-yl)-4-oxo-2-(trifluoromethyl)butan-2-yl]phenyl}-2,3-dihydro-1H-isoindole-1-carboxamide;

Propan-2-yl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate;

2-Acetyl-5-(methylsulfonyl)-N-(4-{1,1,1-trifluoro-4-[(2-fluoroethyl)amino]-4-oxo-2-(trifluoromethyl)butan-2-yl}phenyl)-2,3-dihydro-1H-isoindole-1-carboxamide;

2-Acetyl-N-{4-[4-(dimethylamino)-1,1,1-trifluoro-4-oxo-2-(trifluoromethyl)butan-2-yl]phenyl}-5-(methylsulfonyl)-2,3-dihydro-1H-isoindole-1-carboxamide;

2-Acetyl-N-{4-[4-(tert-butylamino)-1,1,1-trifluoro-4-oxo-2-(trifluoromethyl)butan-2-yl]phenyl}-5-(methylsulfonyl)-2,3-dihydro-1H-isoindole-1-carboxamide;
tert-Butyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate; and
2-Acetyl-N-{4-[4-(acetylamino)-1,1,1-trifluoro-2-(trifluoromethyl)butan-2-yl]phenyl}-5-(methylsulfonyl)-2,3-dihydro-1H-isoindole-1-carboxamide;
or a pharmaceutically acceptable salt thereof.

A further example of a compound of the specification is:
2-Acetyl-N-[4-(2-cyano-1,1,1,3,3,3-hexafluoropropan-2-yl)phenyl]-5-(methylsulfonyl)-2,3-dihydro-1H-isoindole-1-carboxamide;
$N^1$-[4-(2-Cyano-1,1,1,3,3,3-hexafluoropropan-2-yl)phenyl]-$N^2$-methyl-5-(methylsulfonyl)-1,3-dihydro-2H-isoindole-1,2-dicarboxamide;
N-[4-(2-Cyano-1,1,1,3,3,3-hexafluoropropan-2-yl)phenyl]-2-(hydroxyacetyl)-5-(methylsulfonyl)-2,3-dihydro-1H-isoindole-1-carboxamide;
Methyl 1-{[4-(2-cyano-1,1,1,3,3,3-hexafluoropropan-2-yl)phenyl]carbamoyl}-5-(methylsulfonyl)-1,3-dihydro-2H-isoindole-2-carboxylate;
2-Acetyl-N-[4-(2-cyano-1,1,1,3,3,3-hexafluoropropan-2-yl)phenyl]-5-[(cyclopropylmethyl)sulfonyl]-2,3-dihydro-1H-isoindole-1-carboxamide;
2-Acetyl-N-[4-(2-cyano-1,1,1,3,3,3-hexafluoropropan-2-yl)phenyl]-5-(ethylsulfonyl)-2,3-dihydro-1H-isoindole-1-carboxamide;
2-Acetyl-N-{4-[1,1,1,3,3,3-hexafluoro-2-(pyrrolidin-1-yl)propan-2-yl]phenyl}-5-(methylsulfonyl)-2,3-dihydro-1H-isoindole-1-carboxamide; and
2-Acetyl-N-[4-(1,1,1,3,3,3-hexafluoro-2-methoxypropan-2-yl)phenyl]-5-(methylsulfonyl)-2,3-dihydro-1H-isoindole-1-carboxamide;
or a pharmaceutically acceptable salt thereof.

A further feature is any of the embodiments described above with the proviso that any of the specific Examples are individually disclaimed. For example, a further feature is any of the embodiments described above with the proviso that any one or more of the compounds selected from the above list of examples of compounds of the specification are individually disclaimed.

In some embodiments, the compound is a compound of formula (I) excluding at least one compound recited in the Examples below. To illustrate, in some such embodiments, the compound is a compound of formula (I) excluding the compound disclosed in Example X, wherein X may be 1, 2, 3, etc. In other embodiments, the compound is a compound of formula (I) excluding the compounds disclosed in Examples Y, wherein Y may be any combination of 1, 2, 3, etc.

GENERAL METHODS

The compounds of general formula (I) described in the present invention can be readily prepared according to the following reaction schemes. Furthermore, a skilled person in the art will appreciate that where specific reaction conditions are used, it is understood that other suitable reaction conditions may be used to achieve the same transformation and are thus included in the present invention. It will also be clear to the skilled person that where synthetic schemes contain functionalities which may interfere with the desired reaction, suitable protecting groups can be applied. For examples of protecting groups see T. W. Greene and P. G. M. Wuts, "Protective Groups in Organic Synthesis", Third Edition, John Wiley & Sons, New York, 1999.

Scheme 1 represents a general reaction scheme for preparing compounds of formula (Ia).

In both schemes 1 and 2, Z is either acetyl, or a commonly used amine protecting group such as, but not limited to, tert-butyl carbamate (Boc), 9-fluorenylmethyl carbamate (Fmoc) or benzyl carbamate (Cbz). $R^2$ and $R^3$ are defined as above. An intermediate II is reacted with methanesulfonic anhydride and a base such as triethylamine and then further reacted with a suitable nucleophilic reagent such as an amine, an alcohol or a triazole to give compounds of Formula (Ia). In the case of ethers, alkylation of the hydroxyl group is possible.

Scheme 1

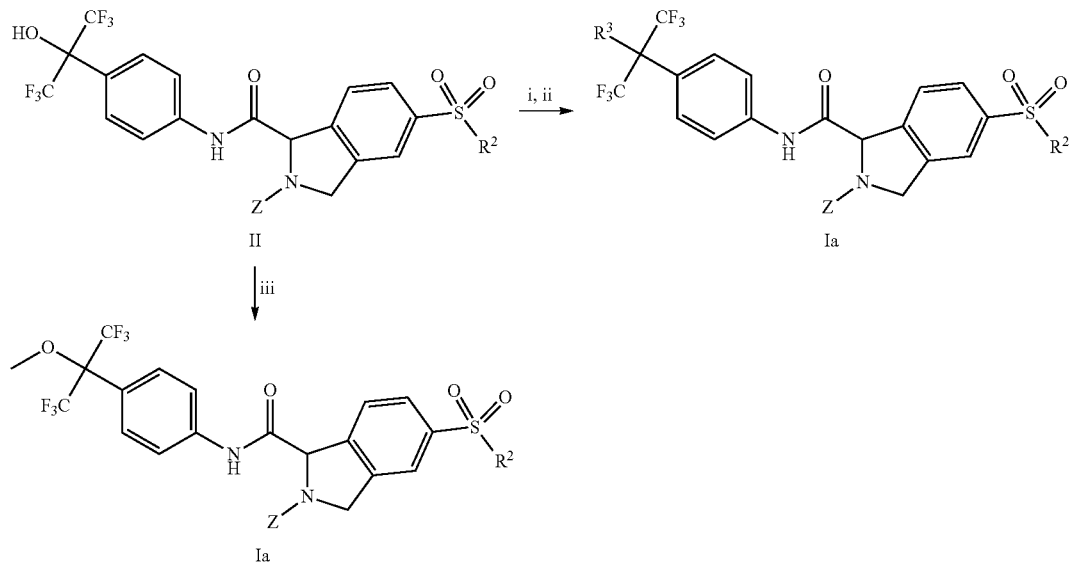

Exemplary conditions: i) Ms$_2$O, NEt$_3$, DCM, rt, ii) ROH, NR$_2$, or triazole, rt or 50° C.; iii) K$_2$CO$_3$, MeI.

Scheme 2 illustrates another general method for preparing compounds of formula (Ia), where Z, $R^2$ and $R^3$ are defined as above. Intermediate III is condensed under standard amide bond forming conditions with intermediate IV. Conditions for this transformation include, but are not limited to the use of commonly used peptide coupling reagents such as EDC and HOBt, HATU and T3P and are conducted in solvents such as DCM, ethyl actetate or DMF in the presence of bases such as triethylamine, DMAP, isopropyl ethylamine or 2,6-lutidine.

In the case where Z is a commonly used amine protecting group such as, but not limited to tert-butyl carbamate (Boc), 9-fluorenylmethyl carbamate (Fmoc) or benzyl carbamate (Cbz), this can be removed to give the amine V, a special case of compounds of formula I for $R^1$=H. These can be obtained either as the free base or as a salt, depending on the deprotection and isolation conditions (Scheme 3).

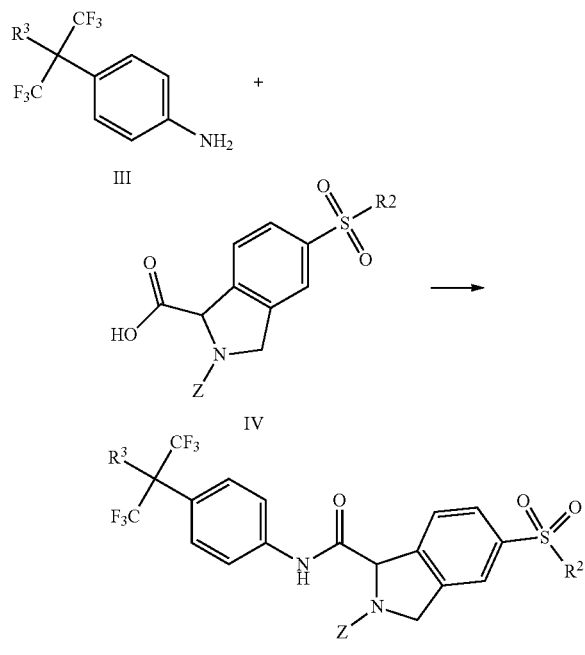

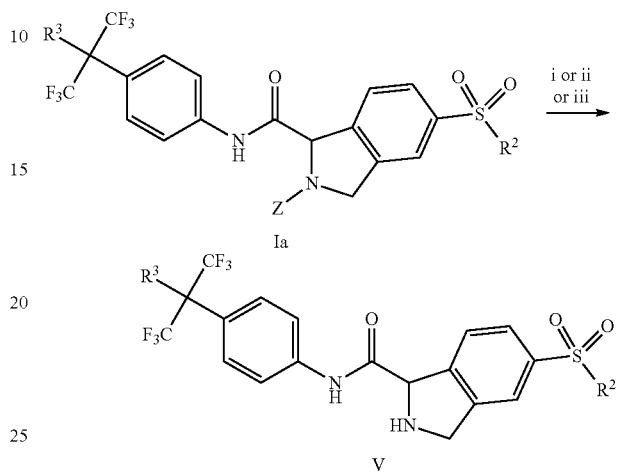

Exemplary conditions: i) Boc deprotection: TFA, DCM; or TBDMSOTf, DCM; or HCl, solvent; ii) Fmoc-deprotection: HNEt$_2$, CH$_3$CN; or morpholine, solvent; iii) Cbz-deprotection: H$_2$, Pd/C, solvent.

As shown in Scheme 4, amine V can then be transformed to an amide, a carbamate or an urea using standard organic chemistry procedures to give compounds of formula I. The reagents for these transformations such as, but not limited to, carboxylic acids, acid chlorides or anhydrides ($R^4CO_2H$, $R^4COCl$, $(R^4CO)_2O$), and corresponding chloroformates are either commercially available or can be prepared using methods known to those skilled in the art. Ureas can be formed from the reaction of V with isocyanates $C_{1-6}$alkyl-N=C=O.

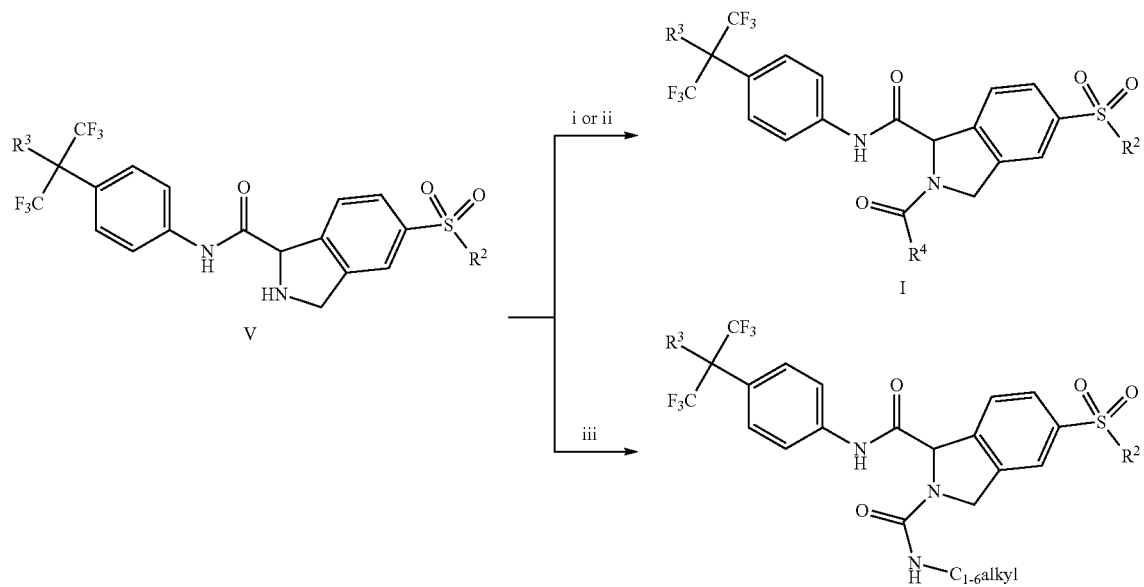

Exemplary conditions: i) Amide bond formation: $R^4CO_2H$, HATU, solvent, base or $R^4COCl$, solvent, base or $(R^4CO)_2O$, base; ii) carbamate formation: chloroformate, base, solvent; iii) urea formation: $C_{1-6}$alkyl-N=C=O, base, solvent A further way to obtain compounds of formula (I) is described in Schemes 5 and 6.
Esters such as VI can be transformed into an acid VII, an alcohol VIII or heterocycle such as IX using standard organic chemistry transformations (Scheme 5).
Scheme 5
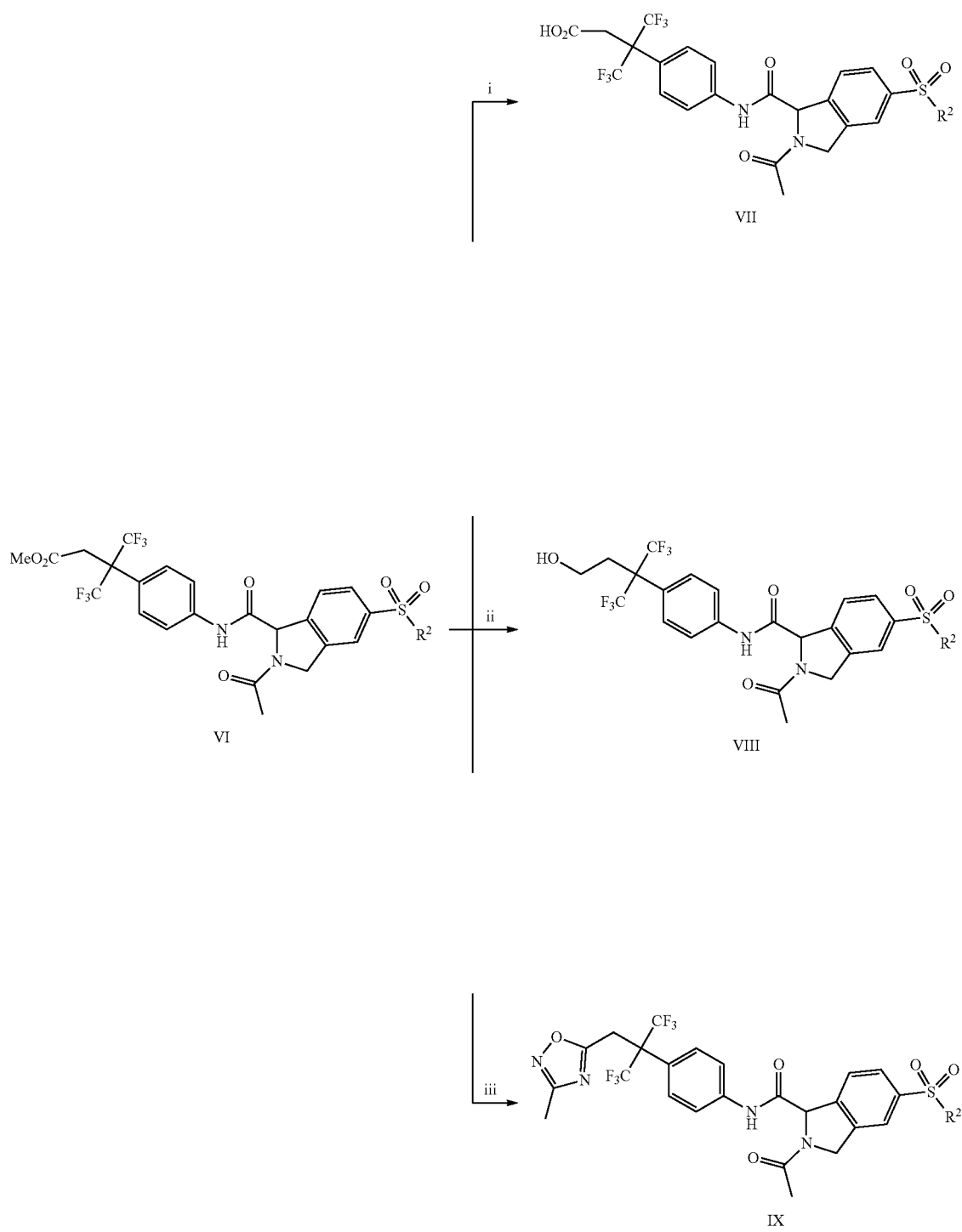
Exemplary conditions: i) NaOH, solvent, ii) NaBH$_4$, THF; iii) MeC=NOH(NH$_2$), NaH, THF.

Acids VII can then further react with amines R⁷R⁸NH or alcohols C$_{1-6}$alkyl-OH under standard amide or ester bond forming conditions to give amides X or ester derivatives XI as shown in Scheme 6.

Scheme 6

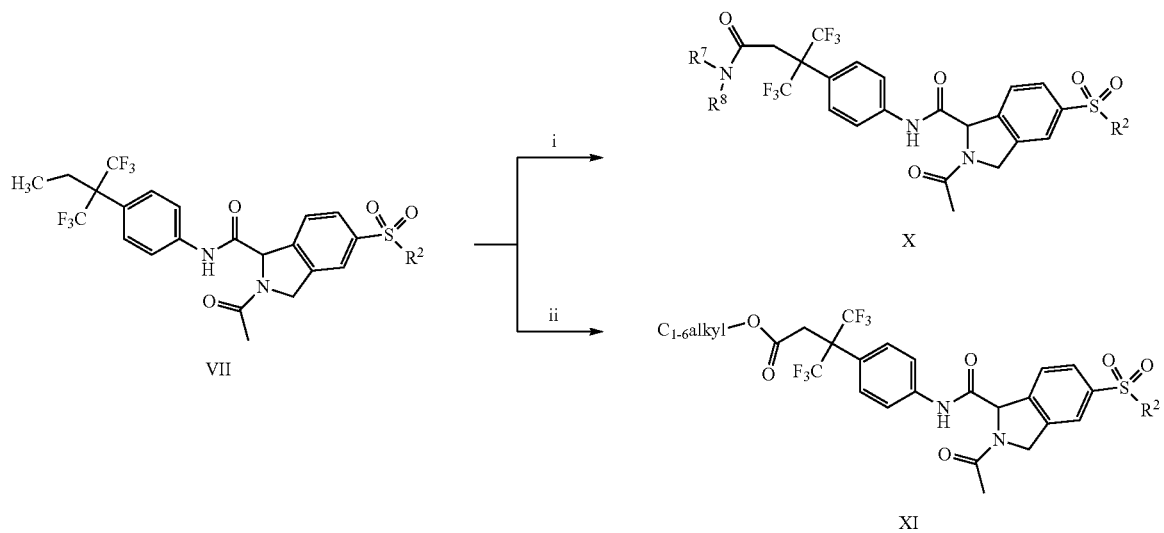

Exemplary conditions: i) T3P, R⁷R⁸NH, EtOAc; ii) T3P, C$_{1-6}$alkylOH, EtOAc.

Intermediate II is made from commercially available 2-(4-aminophenyl)-1,1,1,3,3,3-hexafluoro-propan-2-ol (XII) and intermediate IV (Scheme 7). Conditions for this transformation include, but are not limited to the use of reagents such as EDC and HOBt, HATU and T3P and are conducted in solvents such as DCM, ethyl actetate or DMF in the presence of bases such as triethylamine, DMAP, isopropyl ethylamine or 2,6-lutidine, similar to those described in Scheme 2.

Scheme 7

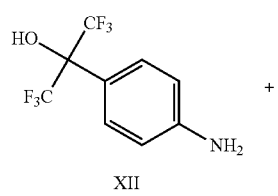

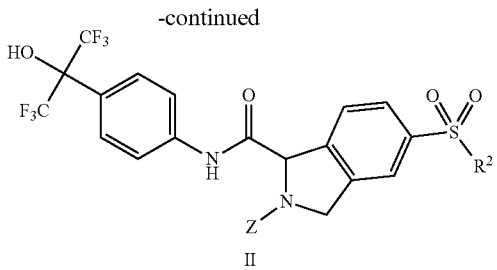

Exemplary conditions: i) EDC, DIPEA, DCM, rt, or T3P, EtOAc, NEt₃, rt.

Intermediates III were usually obtained from the Boc-protected precursors XIII, where R³ is as defined above, using standard acidic deprotection conditions (Scheme 8).

Scheme 8

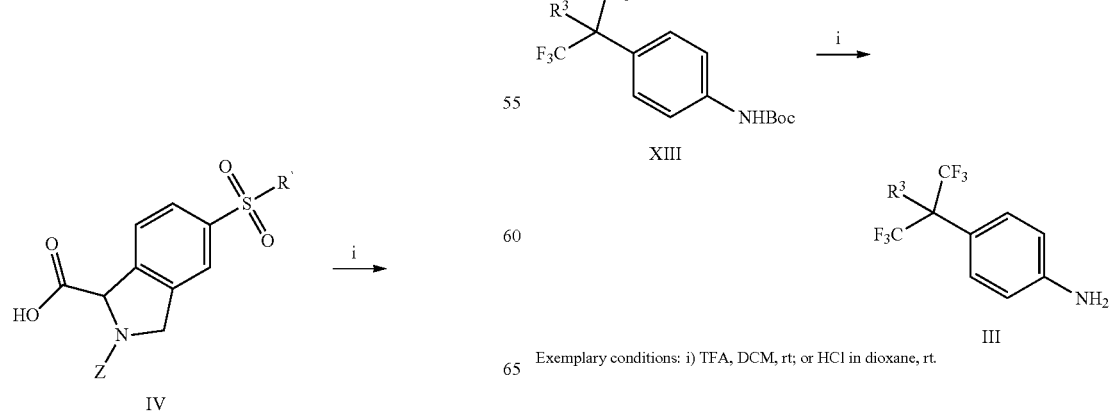

Exemplary conditions: i) TFA, DCM, rt; or HCl in dioxane, rt.

Schemes 9 and 10 show examples for the preparation of variety of building blocks XIII with different substituents $R^3$. In principle, chemistry similar to those in schemes 1, 5 and 6 is used. Compound XIV is reacted with methanesulfonic anhydride for 30 min in a suitable solvent such as DCM or ACN, and then reacted further with a suitable nucleophile (Scheme 9).

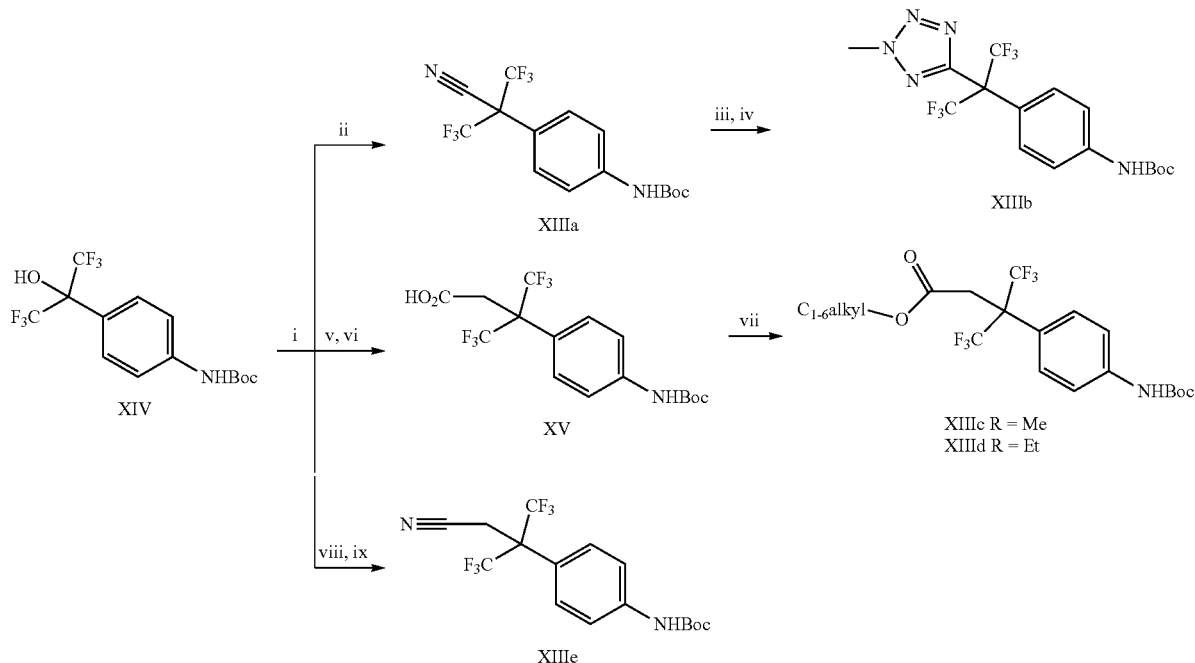

Exemplary conditions: i) Ms$_2$O, NEt$_3$, DCM or ACN, rt; ii) Et$_4$NCN, ACN iii) NaN$_3$, NH$_4$Cl, DMF, 100° C.; iv) K$_2$CO$_3$, MeI; v) CH$_2$(CO$_2$Me)$_2$, NaH, DMF; vi) NaOH, MeOH; vii) MeI or EtI, Na$_2$CO$_3$, DMF; viii) CH$_2$CN(CO$_2$Me), KO$^t$Bu, DMF; ix) NaCl, DMSO, 125° C.

The ester XIIIc obtained in Scheme 9, can be reduced to the alcohol, and the alcohol itself can be further converted to a halogen or an amine derivative. Acid XV can also be converted into an amide. All of these transformations can be accomplished using standard reaction conditions.

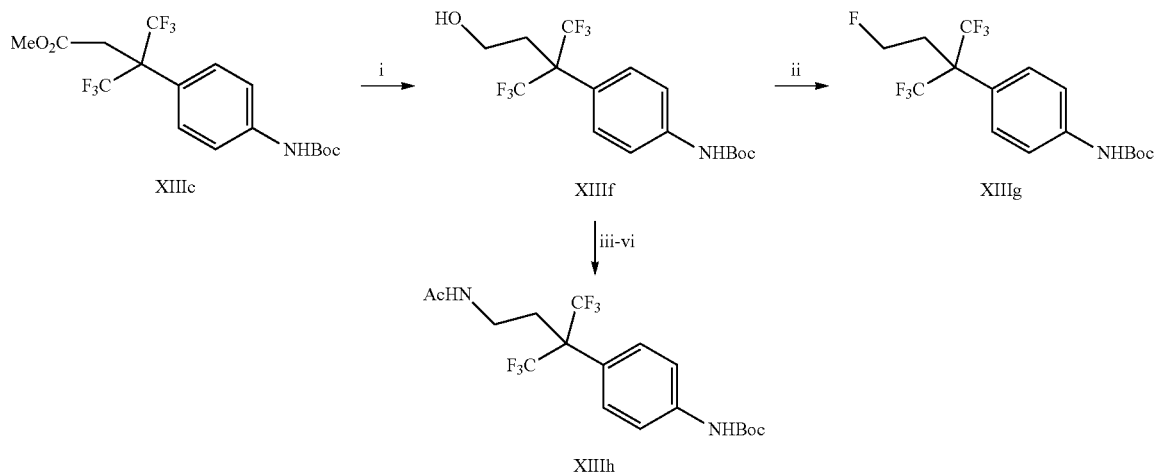

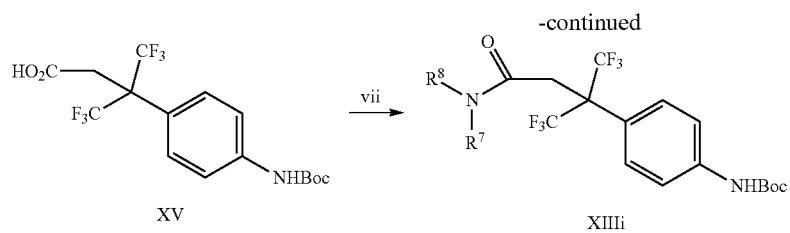

Exemplary conditions: i) LiAlH₄, THF; ii) DAST, DCM; iii) MsCl, NEt₃, DCM; iv) NaN₃, DMF; v) PPh₃, THF; vi) Py, Ac₂O; vii) R⁸R⁷NH, T3P, EtOAc.

Intermediates IV can be prepared by one of the general methods shown in the following Schemes. Introduction of the sulphur residue onto bromo lactam XVI can be conducted in several ways, by base-catalyzed or metal catalyzed substitution of the bromine with $R^2SH$, where $R^2$ is as defined above. This leads to thioethers XVII, which after protection of the lactam NH with a suitable protecting group, such as, but not limited to Boc, gives compounds XVIII, which can be subsequently oxidized to sulphones XIX (Scheme 11). The order of the protection and oxidation step may be changed.

Scheme 11

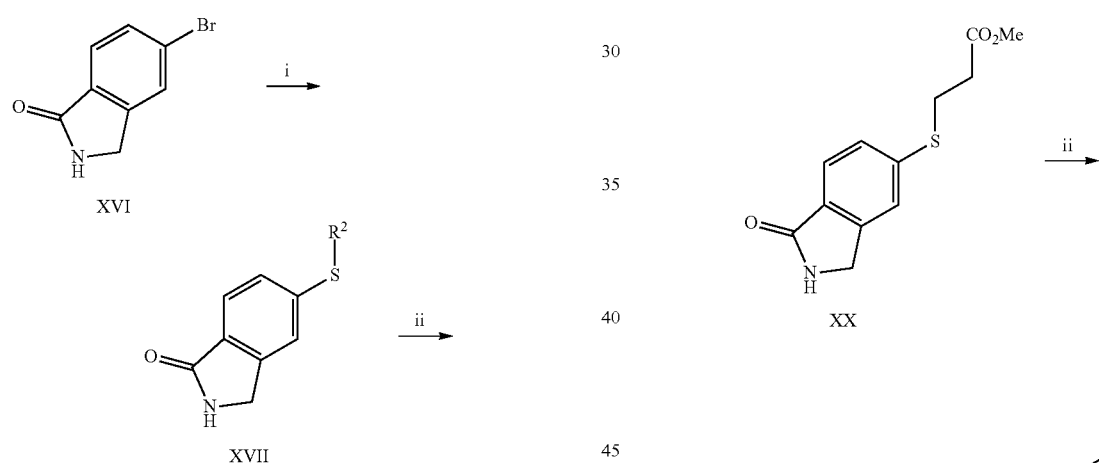

Exemplary conditions: i) R²SH, base, solvent, heat; or R²SNa, DMF, or Pd catalyst, ligand, R²SH, solvent, heat ii) Boc₂O, base, solvent; iii) mCPBA, DCM;

Another approach to thioethers XVII is shown in Scheme 12. A thioether is formed from the bromo lactam as shown in Scheme 11, but the substituent on the sulphur is a protecting group, for example, but not limited to, benzyl or a methyl-propanoate group.

Removal of the protecting group and alkylation of the resulting thiol then leads to the thioethers.

Scheme 12

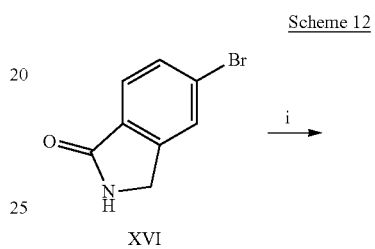

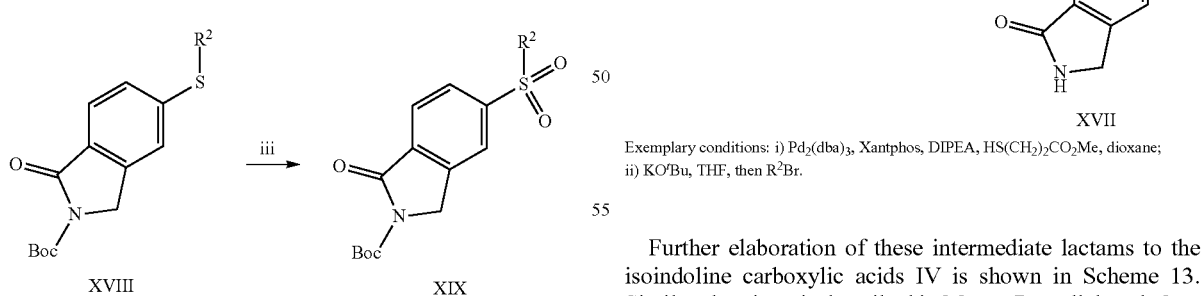

Exemplary conditions: i) Pd₂(dba)₃, Xantphos, DIPEA, HS(CH₂)₂CO₂Me, dioxane; ii) KOᵗBu, THF, then R²Br.

Further elaboration of these intermediate lactams to the isoindoline carboxylic acids IV is shown in Scheme 13. Similar chemistry is described in Moran-Ramallal et al. Org. Lett. 2012, 14, 1696-1699. Reduction of protected lactams XIX is followed by introduction of the cyano group, which is subsequently hydrolyzed to the carboxylic acid. The resulting isoindoline XXIV is then either protected at the nitrogen with a suitable protecting group such as, but not limited to Fmoc or Boc. Alternatively, the group $R^4C(O)$ can be introduced at this stage to give derivative IV or XXV, where Z is defined as above.

Scheme 13

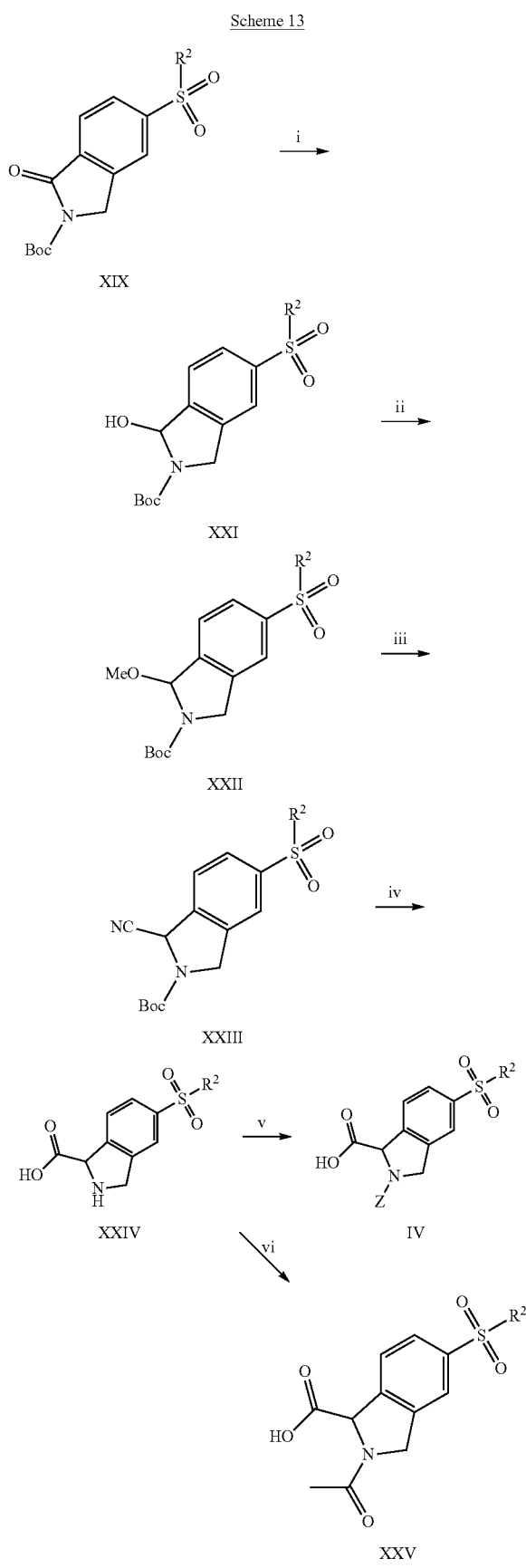

-continued

Exemplary conditions: i) DIBAL-H, THF, -78° C.; or DIBAL-H, DCM, 0° C.; or Li(BEt₃)H, DCM, 0° C. ii) PPTs, MeOH; iii) TMSCN, BF₃·OEt₂, DCM; iv) 6M HCl, heat; or NaOH, heat; v) Boc₂O, base, solvent; or Fmoc-Cl, base, solvent; vi) MeCOCl, base, solvent; or (MeCO)₂O, base solvent.

Detailed processes to the compounds of the specification are further described in the Examples below.

Compounds and salts described in this specification generally may be used in methods to treat various disorders in animals, particularly mammals. Mammals include, for example, humans.

The compounds of the specification, and pharmaceutically acceptable salts thereof, have activity as pharmaceuticals, in particular as modulators of RORγ and/or RORγt, and can be used in the treatment or prevention of an RORγ and/or RORγt mediated disease state. Disease states that may be treated with a compound of the specification, or a pharmaceutically acceptable salt thereof, include but are not limited to immune disorders such as psoriasis, ankylosing spondylitis, psoriatic arthritis, ulcerative colitis, Crohn's disease, multiple sclerosis, inflammatory bowel disease, rheumatoid arthritis, graft versus host disease, systemic lupus erythematosus, lupus nephritis and insulin dependent diabetes type I, and to respiratory disorders such as chronic obstructive pulmonary disease (COPD) and asthma, and to cancer.

The present specification further provides a compound of formula (I) as hereinbefore defined, or a pharmaceutically acceptable salt thereof, for use in therapy.

The present specification further provides, a compound, or a pharmaceutically acceptable salt thereof for the treatment or prevention of an RORγ and/or RORγt mediated disease state.

The present specification further provides a compound of formula (I) as hereinbefore defined, or a pharmaceutically acceptable salt thereof, for the treatment or prevention of chronic obstructive pulmonary disease (COPD), asthma, psoriasis, ankylosing spondylitis or psoriatic arthritis.

The present specification further provides a compound of formula (I) as hereinbefore defined, or a pharmaceutically acceptable salt thereof, for the treatment or prevention of psoriasis.

In another aspect, the specification provides the use of a compound of formula (I) as hereinbefore defined, or a pharmaceutically acceptable salt thereof, in the manufacture of a medicament for use in therapy.

In the context of the present specification, the term "therapy" also includes "prophylaxis" unless there are specific indications to the contrary. The terms "therapeutic" and "therapeutically" should be construed accordingly.

A further aspect provides a method of treating a disease state in a mammal suffering from, or at risk of, said disease, which comprises administering to a mammal in need of such treatment a therapeutically effective amount of a compound of formula (I) as hereinbefore defined, or a pharmaceutically acceptable salt thereof.

A further aspect provides a method of treating or preventing an RORγ and/or RORγt mediated disease state in a mammal suffering from, or at risk of, said disease, which comprises administering to a mammal in need of such treatment a therapeutically effective amount of a compound of formula (I) as hereinbefore defined, or a pharmaceutically acceptable salt thereof.

In another aspect, the specification provides the use of a compound of formula (I) as hereinbefore defined, or a pharmaceutically acceptable salt thereof, in the manufacture of a medicament for use in the treatment or prevention of an RORγ and/or RORγt mediated disease state.

The present specification also provides the use of a compound of formula (I) as hereinbefore defined, or a pharmaceutically acceptable salt thereof, in the manufacture of a medicament for use in the treatment or prevention of chronic obstructive pulmonary disease (COPD), asthma, psoriasis, ankylosing spondylitis or psoriatic arthritis.

The present specification further provides the use of a compound of formula (I) as hereinbefore defined, or a pharmaceutically acceptable salt thereof, in the manufacture of a medicament for use in the treatment or prevention of psoriasis, ankylosing spondylitis or psoriatic arthritis. In a further aspect, the use is in the manufacture of a medicament for use in the treatment or prevention of psoriasis.

The present specification further provides the use of a compound of formula (I) as hereinbefore defined, or a pharmaceutically acceptable salt thereof, in the manufacture of a medicament for use in the treatment or prevention of asthma or COPD.

The present specification further provides a method of treating chronic obstructive pulmonary disease (COPD), asthma, ankylosing spondylitis, psoriatic arthritis or psoriasis in a warm-blooded animal, such as man, which comprises administering to a mammal in need of such treatment a therapeutically effective amount of a compound of formula (I) as hereinbefore defined, or a pharmaceutically acceptable salt thereof. In a further aspect is a method of treating psoriasis.

When a compound or salt described in this specification is administered to treat a disorder, a "therapeutically effective amount" is an amount sufficient to reduce or completely alleviate symptoms or other detrimental effects of the disorder; cure the disorder; reverse, completely stop, or slow the progress of the disorder; or reduce the risk of the disorder getting worse.

In some embodiments in which a combination therapy is used, the amount of the compound or salt described in this specification and the amount of the other pharmaceutically active agent(s) are, when combined, therapeutically effective to treat a targeted disorder in the animal patient. In this context, the combined amounts are "therapeutically effective amounts" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound or salt and an approved or otherwise published dosage range(s) of the other pharmaceutically active compound(s).

In order to use a compound of the specification, or a pharmaceutically acceptable salt thereof, for the therapeutic treatment of a mammal, such as human, said ingredient is normally formulated in accordance with standard pharmaceutical practice as a pharmaceutical composition. Therefore in another aspect the present specification provides a pharmaceutical composition which comprises a compound of the formula (I), or a pharmaceutically acceptable salt thereof (active ingredient), and at least one pharmaceutically acceptable excipient.

The pharmaceutical composition is typically intended for use in the therapeutic and/or prophylactic treatment of a warm-blooded animal, such as man.

Therefore the present specification provides a pharmaceutical composition that comprises a compound of the specification (or a pharmaceutically acceptable salt thereof) and one or more pharmaceutically acceptable excipients.

By the term "pharmaceutically acceptable excipient" we mean a substance that serves as a vehicle or medium for the compound of the specification (or a pharmaceutically acceptable salt thereof), i.e. so as to prepare the active ingredient in a form suitable for administration. Generally the pharmaceutically acceptable excipients are pharmacologically inactive. Each excipient should be compatible with the other ingredients in the composition and should be acceptable for administration to a warm-blooded animal, such as man.

The excipient(s) selected for inclusion in a particular composition will depend on factors such as the mode of administration and the form of the composition provided. Suitable pharmaceutically acceptable excipients are well known to persons skilled in the art and are described, for example, in the Handbook of Pharmaceutical Excipients, Sixth edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colourants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

A pharmaceutical composition of the specification may comprise one or more further active ingredients, as appropriate, examples of combinations of a compound of the specification (or a pharmaceutically acceptable salt thereof) and one or more additional active ingredients are described herein.

A process for the preparation of the pharmaceutical composition may comprise the step of mixing a compound of the specification (or a pharmaceutically acceptable salt thereof) with one or more pharmaceutically acceptable excipients. The process may further comprise the step of mixing one or more further active ingredients with a compound of the specification (or a pharmaceutically acceptable salt thereof) and one or more pharmaceutically acceptable excipients. The processes are conducted using techniques and methods known to persons skilled in the art.

The pharmaceutical composition of the specification may be administered in a standard manner for the disease that it is desired to treat and/or prevent. For example, suitable modes of administration include oral, intravenous, rectal, parenteral, topical, ocular, nasal, buccal or pulmonary administration. For these purposes a compound of the specification (or a pharmaceutically acceptable salt thereof) may be formulated by means known in the art into the form of, for example, tablets, capsules, syrups, powders, granules, aqueous or oily solutions or suspensions, (lipid) emulsions, dispersible powders, suppositories, ointments, creams, drops, aerosols, dry powder formulations, and sterile injectable aqueous or oily solutions or suspensions.

The magnitude of prophylactic or therapeutic dose of a compound of the specification (or a pharmaceutically acceptable salt thereof) will vary depending upon a range of factors, including the activity of the specific compound (or pharmaceutically acceptable salt thereof) that is used, the age, body weight, diet, general health and sex of the patient, time of administration, the route of administration, the rate of excretion, the use of any other active ingredients, and the severity of the disease undergoing treatment.

Depending on the mode of administration, the pharmaceutical composition of the specification will comprise from 0.05 to 99% w/w (percent by weight), such as from 0.05 to 80% w/w, for example from 0.10 to 70% w/w, such as from 0.10 to 50% w/w, of a compound of the specification (or a pharmaceutically acceptable salt thereof), all percentages by weight being based on the total composition.

The present specification provides a pharmaceutical composition comprising a compound of the specification (or a pharmaceutically acceptable salt thereof) and one or more pharmaceutically acceptable excipients, which composition is formulated for oral administration.

A pharmaceutical composition of the specification that is suitable for oral administration may be provided in unit dosage form, for example in the form of a tablet or capsule. Such a unit dosage form may contain from 0.1 mg to 1 g, for example from 5 mg to 250 mg, of a compound of the specification (or a pharmaceutically acceptable salt thereof) as active ingredient.

For oral administration a compound of the specification (or a pharmaceutically acceptable salt thereof) may be admixed with one or more excipients, such as a carrier and/or a binder and/or a lubricant. Suitable carriers include, for example, lactose, saccharose, sorbitol, mannitol, a starch (for example, potato starch, corn starch or amylopectin) and a cellulose derivative. Suitable binders include, for example, gelatine or polyvinylpyrrolidone. Suitable lubricants include, for example, magnesium stearate, calcium stearate, polyethylene glycol, a wax, paraffin, and the like. The mixture may then be compressed into tablets using known techniques. If coated tablets are required, the cores, prepared as described above, may be coated with a suitable coating agent, for example with a concentrated sugar solution which may contain, for example, gum arabic, gelatine, talcum and/or titanium dioxide. Alternatively, the tablet may be coated with a suitable polymer dissolved in a readily volatile organic solvent.

For the preparation of soft gelatine capsules, a compound of the specification (or a pharmaceutically acceptable salt thereof) may be admixed with one or more excipients, such as a diluent. Suitable diluents include, for example, a vegetable oil or polyethylene glycol. Hard gelatine capsules may contain granules of the compound (or salt) using the above-mentioned excipients for tablets. Also liquid or semi-solid formulations of a compound of the specification (or a pharmaceutically acceptable salt thereof) may be filled into hard gelatine capsules.

Liquid preparations for oral application may be in the form of syrups or suspensions, for example, solutions containing a compound of the specification (or a pharmaceutically acceptable salt thereof), the balance being sugar and a mixture of ethanol, water, glycerol and propylene glycol. Optionally such liquid preparations may contain colourants, flavours, saccharine and/or carboxymethylcellulose as a thickening agent or other excipients known to those skilled in art.

The present specification further provides a pharmaceutical composition comprising a compound of the specification (or a pharmaceutically acceptable salt thereof) and one or more pharmaceutically acceptable excipients, which composition is formulated for topical administration. Topical administration may, for example, be in the form of creams, lotions, ointments or transdermal patches. Creams and ointments may comprise an aqueous or oily base to which suitable thickening or gelling agents are applied. Lotions may comprise an aqueous or oily base to which one or more emulsifying agents, stabilising agents, dispersing agents, suspending agents or thickening agents are applied.

The specification further relates to a combination therapy wherein a compound of the specification, or a pharmaceutically acceptable salt thereof, and a second active ingredient are administered concurrently, sequentially or in admixture, for the treatment of one or more of the conditions listed above. Such a combination may be used in combination with one or more further active ingredients.

In one aspect there is provided a combination (for example, for use as a medicament for the treatment of one of the diseases or conditions listed herein, such as chronic obstructive pulmonary disease (COPD) or asthma) comprising a compound of the specification, or a pharmaceutically acceptable salt thereof, and at least one active ingredient selected from:

a) a beta-adrenoceptor agonist;
b) a muscarinic receptor antagonist;
c) a joint muscarinic receptor antagonist and beta-adrenoceptor agonist; and
d) a glucocorticoid receptor agonist (steroidal or non-steroidal).

In another aspect there is provided a combination (for example, for use as a medicament for the treatment of one of the diseases or conditions listed herein, such as chronic obstructive pulmonary disease (COPD) or asthma) comprising a compound of the specification, or a pharmaceutically acceptable salt thereof, and a phosphodiesterase-4 (PDE4) inhibitor.

In a further aspect of the present specification there is provided a pharmaceutical composition (for example, for use as a medicament for the treatment of one of the diseases or conditions listed herein, such as chronic obstructive pulmonary disease (COPD) or asthma) comprising a compound of the specification, or a pharmaceutically acceptable salt thereof, and at least one active ingredient selected from:

a) a beta-adrenoceptor agonist;
b) a muscarinic receptor antagonist;
c) a joint muscarinic receptor antagonist and beta-adrenoceptor agonist; and
d) a glucocorticoid receptor agonist (steroidal or non-steroidal).

In another aspect there is provided a pharmaceutical composition (for example, for use as a medicament for the treatment of one of the diseases or conditions listed herein, such as chronic obstructive pulmonary disease (COPD) or asthma) comprising a compound of the specification, or a pharmaceutically acceptable salt thereof, and a phosphodiesterase-4 (PDE4) inhibitor.

The compounds described in this specification are further illustrated in the following Examples. These Examples are given by way of illustration only and are non-limiting.

Chemical names are preferably IUPAC names which were generated using ACD Labs 2014, or ChemDraw Ultra version 11.0.

Abbreviations

ACN acetonitrile
$Boc_2O$ di-tert-butyl dicarbonate
CDI 1,1'-carbonyldiimidazole
DCM dichloromethane
DAST diethylaminosulfur trifluoride
DBU 2,3,4,6,7,8,9,10-octahydropyrimido[1,2-a]azepine
DIBAL-H diisobutylaluminum hydride
DIPEA diisopropylethylamine DMAP 4-N,N-dimethylamino pyridine
DMF dimethylformamide
DMSO dimethylsulfoxide
dppf 1,1'-bis(diphenylphosphino)ferrocene
EDC N$^1$-((ethylimino)methylene)-N$^3$,N$^3$-dimethylpropane-1,3-diamine hydrochloride
ESI electrospray ionization
EtOH ethanol
EtOAc ethyl acetate
Fmoc-Cl 9-fluorenylmethyl chloroformate
h hour
HATU 1-[bis(dimethylamino)methylene]-1H-1,2,3-triazolo[4,5-b]pyridinium 3-oxid hexafluorophosphate
HOBt 1H-benzo[d][1,2,3]triazol-1-ol hydrate
HPLC high-performance liquid chromatography
IPA isopropyl alcohol
LC/MS liquid chromatography-mass spectroscopy
LHMDS lithium bis(trimethylsilyl)amide
mCPBA 3-chloroperoxybenzoic acid
MeOH methanol
min minutes
MsCl methanesulfonyl chloride
MTBE methyl tert-butyl ether
NBS N-bromosuccinimide
NCS N-chlorosuccinimide
NsCl 4-nitrobenzenesulfonyl chloride
PFA Perfluoroalkoxy
(PinB)$_2$ bis(pinacolato)diboron
PPTs pyridinium para-toluenesulphonate
Py pyridine
rt room temperature
RP-HPLC reverse phase HPLC
SFC supercritical fluid chromatography
T3P 2,4,6-tripropyl-1,3,5,2,4,6-trioxatriphosphinane 2,4,6-trioxide
TBAF tetra-n-butylammonium fluoride
TBDMSCl tert-butyldimethylsilyl chloride
TBDMSOTf tert-butyldimethylsilyl trifluoromethanesulfonate
TBTU 2-(1H-benzo[d][1,2,3]triazol-1-yl)-1,1,3,3-tetramethylisouronium tetrafluoroborate
TFA trifluoroacetic acid
TFAA trifluoroacetic anhydride
THF tetrahydrofuran
TMSCN trimethylsilyl cyanide
TsCl para-toluenesulphonyl chloride
TsOH para-toluenesulphonic acid General Methods NMR spectra were recorded on a Bruker Avance, Avance II or Avance III spectrometer at a proton frequency of 300, 400, 500 or 600 MHz. The central peaks of chloroform-δ (H 7.26 ppm), CD$_3$OD (H 3.30 ppm) or DMSO-d$_6$ (H 2.49 ppm) were used as internal references.

LC/MS experiments were performed using a Waters Acquity system combined with a Waters Xevo Q-ToF Mass or a Shimadzu 2010EV UPLC system in ESI mode. LC was run in two set ups: 1) BEH C18 column (1.7 μm 2.1×50 mm) in combination with a gradient (2-95% B in 5 min) of aqueous 46 mM ammonium carbonate/ammonia buffer at pH 10 (A) and ACN (B) at a flow rate of 1.0 mL/min or in combination with a gradient (5-95% B in 2 min) of water and TFA (0.05%) (A) and CH$_3$CN and TFA (0.05%) at a flow rate of 1.0 mL/min (B).

Preparative HPLC was performed with a Waters FractionLynx system with integrated MS detection and equipped with Prep C18 OBD 5 μm 19×150 mm columns from X-Bridge or Sunfire. Alternatively Gilson GX-281 with integrated UV detection was used, equipped with either Kromasil C8 10 μm, 20×250 ID or 50×250 ID mm. As eluent (acidic) gradients of water/ACN/acetic acid (95/5/0.1) or water/0.05% TFA (A) and ACN/0.05% TFA (B) or (basic) ACN or MeOH (A) and 0.03% ammonia in water or 0.03% NH$_4$HCO$_3$ (B) were applied.

Preparative SCF was performed with a Waters Prep100 SCF system with integrated MS detection, equipped with Waters Viridis 2-EP or Phenomenex Luna Hilic, 30×250 mm, 5 μm. As eluent gradients of CO$_2$ (100 g/min, 120 bar, 40° C.) (A) and MeOH/NH$_3$ (20 mM) or MeOH (5% formic acid) or MeOH (B) were applied.

Unless otherwise stated, starting materials were commercially available or previously described in the literature. All solvents and commercial reagents were of laboratory grade and were used as received unless otherwise stated.

Intermediate 1: 2-(4-Aminophenyl)-3,3,3-trifluoro-2-(trifluoromethyl)propanenitrile

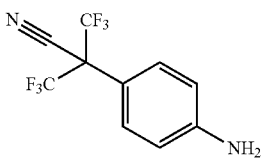 [SMILES: N#CC(c1ccc(N)cc1)(C(F)(F)F)C(F)(F)F]

Step 1: tert-Butyl (4-(1,1,1,3,3,3-hexafluoro-2-hydroxypropan-2-yl)phenyl)carbamate

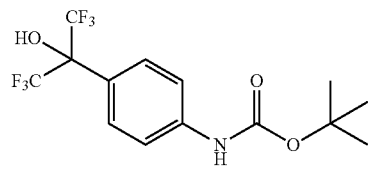 [SMILES: CC(C)(C)OC(=O)Nc1ccc(C(O)(C(F)(F)F)C(F)(F)F)cc1]

A solution of 0.38M aqueous sodium hydroxide (254 mL, 96.47 mmol) was added to a solution of 2-(4-aminophenyl)-1,1,1,3,3,3-hexafluoropropan-2-ol (25 g, 96.47 mmol) in dioxane (100 mL) at room temperature. Di-tert-butyl dicarbonate (29.5 g, 135.06 mmol) was added and the turbid reaction mixture was stirred overnight at room temperature. The reaction was transferred to a sep funnel and the product extracted into DCM (2×300 mL). The combined DCM extractions were washed with water (100 mL) and brine (50 mL) before passing through a phase separator. The organic solution was concentrated in vacuo to afford the title product as a pale orange oil which slowly solidified. The yield was assumed quantitative and the material was used crude in the next step.

LC/MS: m/z=358 [M−H]$^-$. 1H NMR (400 MHz, DMSO-d$_6$) δ 1.48 (s, 9H), 7.52-7.59 (m, 4H), 8.53 (s, 1H), 9.58 (s, 1H).

Step 2: tert-Butyl N-[4-[1-cyano-2,2,2-trifluoro-1-(trifluoromethyl)ethyl]phenyl]carbamate

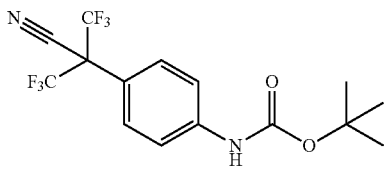 [SMILES: CC(C)(C)OC(=O)Nc1ccc(C(C#N)(C(F)(F)F)C(F)(F)F)cc1]

Using a Vapourtec R2C+/R4 flow chemistry platform, a pumped solution (flow rate 2.000 mL/min) of tert-butyl (4-(1,1,1,3,3,3-hexafluoro-2-hydroxypropan-2-yl)phenyl) carbamate (11.5 g, 32.01 mmol) and triethylamine (13.31 mL, 96.03 mmol) in anhydrous ACN (200 mL) was combined with a pumped solution (flow rate 2.000 mL/min) of methanesulfonic anhydride (16.73 g, 96.03 mmol) in anhydrous ACN (200 mL). The combined solution was reacted in 2×10 mL PFA tube reactors at 30° C. (residence time 5 min) before a pumped solution (flow rate of 2.000 mL/min) of tetraethylammonium cyanide (25.0 g, 160.05 mmol) in anhydrous ACN (200 mL) was introduced. The solution was reacted in 2×10 mL PFA tube reactors at 30° C. (residence time 3.33 min). The reaction solution was collected in a single fraction and concentrated under reduced pressure; the residue was dissolved in EtOAc (500 mL) and washed consecutively with water (3×200 mL) and brine (75 mL) before drying over MgSO$_4$. The solution was filtered and concentrated under reduced pressure. tert-Butyl N-[4-[1-cyano-2,2,2-trifluoro-1-(trifluoromethyl)ethyl]phenyl]carbamate (8.0 g, 64% yield) was isolated as a colourless syrup by automated flash column chromatography on a Biotage® KP-SIL 340 g column, using a gradient of 0% to 15% EtOAc in heptane as mobile phase.

LC/MS: m/z=367 [M−H]$^-$. $^1$H-NMR (400 MHz, CDCl$_3$) δ 1.54 (s, 9H), 6.67 (s, 1H), 7.54 (d, 2H), 7.63 (d, 2H). $^{19}$F-NMR (376 MHz, CDCl$_3$) δ −66.79.

Step 3: 2-(4-Aminophenyl)-3,3,3-trifluoro-2-(trifluoromethyl)propanenitrile

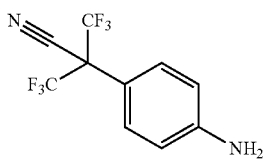 [SMILES: N#CC(c1ccc(N)cc1)(C(F)(F)F)C(F)(F)F]

tert-Butyl N-[4-[1-cyano-2,2,2-trifluoro-1-(trifluoromethyl)ethyl]phenyl]carbamate (5.8 g, 15.75 mmol) was dissolved in DCM (80 mL). To this TFA (25 mL, 324.49 mmol) was added and the reaction was stirred at rt for 1 h. The reaction was concentrated in vacuo and the residue dissolved in EtOAc and washed twice with saturated NaHCO$_3$. The layers were separated and the organic layer was dried using a phase sep cartridge and concentrated in vacuo. 2-(4-Aminophenyl)-3,3,3-trifluoro-2-(trifluoromethyl)propanenitrile (4.02 g, 95%) was obtained as an oil and used without further purification.

LC/MS: m/z=269 [M+H]$^+$. $^1$H NMR (500 MHz, DMSO-d$_6$) δ 5.86 (s, 2H), 6.67-6.76 (m, 2H), 7.32 (d, 2H).

Intermediate 2: 9H-Fluoren-9-ylmethyl 1-[[4-[1-cyano-2,2,2-trifluoro-1-(trifluoromethyl)ethyl]phenyl]carbamoyl]-5-methyl-sulfonyl-isoindoline-2-carboxylate

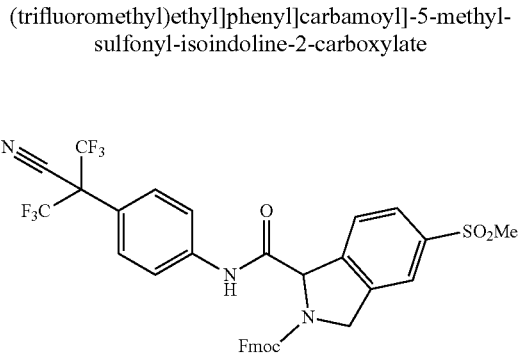

Step 1: 5-(Methylthio)isoindolin-1-one

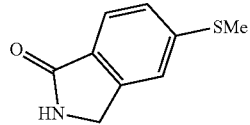 [SMILES: CSc1ccc2c(c1)CNC2=O]

5-Bromoisoindolin-1-one (15 g, 70.74 mmol) and sodium methyl mercaptide (12.40 g, 176.85 mmol) were mixed together in DMF (150 mL) and heated to 100° C. for 1 h. The reaction mixture was cooled to room temperature and poured into water (160 mL), and the aqueous phase was extracted with EtOAc (400 mL). The layers were then separated and the aqueous phase extracted with EtOAc (3×200 mL). The combined organic extracts were washed with brine (3×100 mL), dried using a phase separator cartridge and concentrated in vacuo. 5-(Methylthio)isoindolin-1-one (12.00 g, 95%) was obtained as a yellow solid. The material was used in the next step without further purification.

LC/MS: m/z=180 [M+H]$^+$. $^1$H NMR (500 MHz, DMSO-d$_6$) δ 2.54 (s, 3H), 4.33 (s, 2H), 7.33 (d, 1H), 7.44 (s, 1H), 7.56 (d, 1H), 8.43 (s, 1H).

Step 2: tert-Butyl 5-(methylthio)-1-oxoisoindoline-2-carboxylate

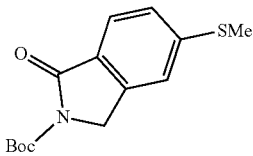 [SMILES: CSc1ccc2c(c1)CN(C(=O)OC(C)(C)C)C2=O]

5-(Methylthio)isoindolin-1-one (12.68 g, 70.74 mmol) was suspended in ACN (500 mL) and DMAP (12.10 g, 99.04 mmol) was added in one portion. Di-tert-butyl dicarbonate (21.61 g, 99.04 mmol) was then added and the reaction stirred for 20 min at room temperature. The ACN was removed in vacuo. The residue was dissolved in EtOAc and washed with 0.5M aq HCl (3×200 ml). The organic extract was dried using a phase separator cartridge and concentrated in vacuo. tert-Butyl 5-(methylthio)-1-oxoisoindoline-2-carboxylate (15.60 g, 79%) was obtained as a brown oil that solidified on standing. The material was used in the next step without further purification.

$^1$H NMR (500 MHz, DMSO-d$_6$) δ 1.51 (s, 9H), 2.55 (s, 3H), 4.74 (s, 2H), 7.37 (d, 1H), 7.49 (s, 1H), 7.64 (d, 1H).

Step 3: tert-Butyl 5-(methylsulfonyl)-1-oxoisoindoline-2-carboxylate

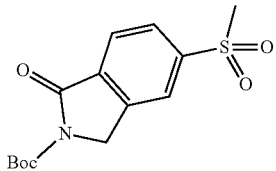

tert-Butyl 5-(methylthio)-1-oxoisoindoline-2-carboxylate (15.58 g, 55.77 mmol) was dissolved in DCM (500 mL) and to this mCPBA (≥77%) (30.0 g, 133.85 mmol) was added portion wise (an exotherm to ca. 38° C. was observed). The reaction was stirred at room temperature for 20 min. The reaction was washed twice with 1M aq NaOH. The organic layer was dried using a phase separator cartridge and concentrated in vacuo to afford tert-butyl 5-(methylsulfonyl)-1-oxoisoindoline-2-carboxylate (15.56 g, 90%) as a yellow solid. The material was used in the next step without further purification.

LC/MS: m/z=310 [M–H]$^-$. $^1$H NMR (500 MHz, DMSO-d$_6$) δ 1.53 (s, 9H), 3.31 (s, 3H), 4.88 (s, 2H), 8.00 (d, 1H), 8.08 (d, 1H), 8.25 (s, 1H).

Step 4: tert-Butyl 1-hydroxy-5-(methylsulfonyl) isoindoline-2-carboxylate

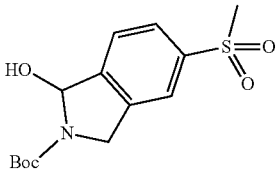 [SMILES: CC(C)(C)OC(=O)N1Cc2cc(S(C)(=O)=O)ccc2C1O]

tert-Butyl 5-(methylsulfonyl)-1-oxoisoindoline-2-carboxylate (15.56 g, 49.98 mmol) was dissolved in DCM (375 mL), cooled in an ice bath and kept under a nitrogen atmosphere. DIBAL-H (85 mL, 84.96 mmol, 1M solution in THF) was added gradually over 10 min. The reaction was stirred at this temperature for 15 min. A saturated aqueous solution of Rochelle's salt (100 ml) was added and the resultant mixture was stirred for 20 min whilst warming to room temperature. DCM (200 mL) was added and the layers separated. The aqueous layer was extracted with DCM. The combined organic extracts were dried using a phase separator cartridge and concentrated in vacuo. The product was obtained as a pink-brown gum/foam which was used crude in the next step.

LC/MS: m/z=312 [M–H]$^-$.

Step 5: tert-Butyl 1-methoxy-5-(methylsulfonyl) isoindoline-2-carboxylate

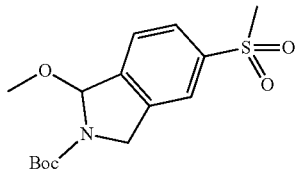 [SMILES: COC1c2ccc(S(C)(=O)=O)cc2CN1C(=O)OC(C)(C)C]

tert-Butyl 1-hydroxy-5-(methylsulfonyl)isoindoline-2-carboxylate (15.66 g, 49.98 mmol) was dissolved in MeOH (300 mL) and to this PPTs (1.26 g, 5 mmol) was added and the reaction stirred at room temperature. After 20 min LCMS indicated that no starting material remained and one product had formed. The reaction was quenched by addition of triethylamine (111 mL, 799.68 mmol) and concentrated in vacuo to afford a dark purple oil. This was used crude in the next step.

Step 6: tert-Butyl 1-cyano-5-(methylsulfonyl)isoindoline-2-carboxylate

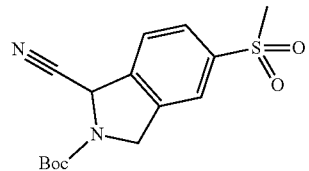 [SMILES: CC(C)(C)OC(=O)N1Cc2cc(S(C)(=O)=O)ccc2C1C#N]

tert-Butyl 1-methoxy-5-(methylsulfonyl)isoindoline-2-carboxylate (16.36 g, 49.98 mmol) was dissolved in DCM (375 mL). This was cooled to –78° C. before TMSCN (10.05 mL, 74.97 mmol) and BF$_3$·OEt$_2$ (9.50 mL, 74.97 mmol) was added. The reaction was stirred at –78° C. for 15 min. An aqueous saturated solution of NaHCO$_3$ and DCM was added and the reaction allowed to warm to room temperature. The two layers were separated and the aqueous phase extracted with DCM. The combined organic extracts were dried using a phase separator cartridge and concentrated in vacuo. The material was purified by flash chromatography eluting with 40-50% EtOAc in heptane. tert-Butyl 1-cyano-5-(methylsulfonyl)isoindoline-2-carboxylate (10.6 g, 65.8%) was obtained as a solid.

LC/MS: m/z=321 [M–H]$^-$. $^1$H NMR (500 MHz, DMSO-d$_6$, mixture of rotamers, 1:1) δ 1.50, 1.51 (s, 9H), 3.24, 3.25 (s, 3H), 4.74, 4.76 (s, 2H), 6.17, 6.19 (s, 1H), 7.83 (d, 1H), 7.96-8.05 (m, 2H).

Step 7: 5-(Methylsulfonyl)isoindoline-1-carboxylic acid, hydrochloride salt

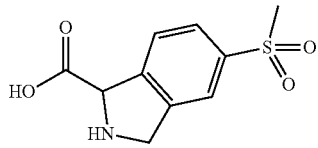 [SMILES: CS(=O)(=O)c1ccc2c(c1)CNC2C(=O)O]

6M aq HCl (110 mL, 660.00 mmol) was added to tert-butyl 1-cyano-5-(methylsulfonyl)isoindoline-2-carboxylate (10.6 g, 32.88 mmol) and the mixture was heated at 70° C. for 2.5 h. The reaction was cooled to room temperature and concentrated to dryness to afford a dark solid, which was used in the next step without further purification.

LC/MS: m/z=240 [M−H]⁻.

Step 8: 2-[(9H-Fluoren-9-ylmethoxy)carbonyl]-5-(methylsulfonyl)-2,3-dihydro-1H-isoindole-1-carboxylic acid

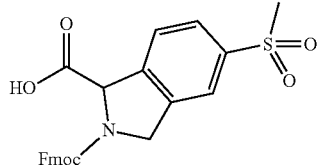

To 5-(methylsulfonyl)isoindoline-1-carboxylic acid, hydrochloride salt (9.13 g, 32.88 mmol) in dioxane (230 mL)/water (230 mL) was added potassium carbonate (22.72 g, 164.40 mmol) and 9-fluorenylmethyl chloroformate (7.66 g, 29.59 mmol). The reaction was stirred at room temperature overnight. The dioxane was removed in vacuo. The aqueous was then acidified with 1M aq HCl and extracted with EtOAc. These organic extracts were combined, dried using a phase separator and concentrated in vacuo. The material was used crude in the next step.

LC/MS: m/z=462 [M−H]⁻.

Step 9: 9H-Fluoren-9-ylmethyl 1-[[4-[1-cyano-2,2,2-trifluoro-1-(trifluoromethyl)ethyl]phenyl]carbamoyl]-5-methylsulfonyl-isoindoline-2-carboxylate

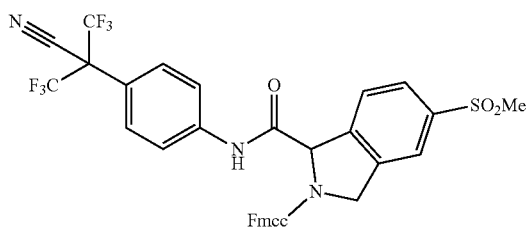

T3P (50% solution in EtOAc, 1.310 mL, 2.20 mmol) was added to a mixture of 2-[(9H-fluoren-9-ylmethoxy)carbonyl]-5-(methylsulfonyl)-2,3-dihydro-1H-isoindole-1-carboxylic acid (510 mg, 1.1 mmol), 2-(4-aminophenyl)-3,3,3-trifluoro-2-(trifluoromethyl)propanenitrile (Intermediate 1, 236 mg, 0.88 mmol) and triethylamine (0.307 mL, 2.20 mmol) in DCM (10 mL). This was stirred at room temperature for 30 min. The reaction mixture was washed with water and the layers separated using a phase separator cartridge. The DCM was removed in vacuo and the residue purified by flash chromatography eluting with 25-40% EtOAc in heptane to give the title compound (315 mg, 40.1%) as a solid.

LC/MS: m/z=714 [M+H]⁺. ¹H NMR (500 MHz, DMSO-d₆, mixture of rotamers, 1:1) δ 3.22, 3.23 (s, 3H), 4.13-4.42 (m, 3H), 4.86-5.05 (m, 2H), 5.73, 5.79 (s, 1H), 6.93-7.01 (m, 1H), 7.23, 7.30 (t, 1H), 7.37 (q, 1H), 7.44 (q, 1H), 7.56, 7.58 (d, 1H), 7.7-7.83 (m, 5H), 7.9-7.97 (m, 4H), 8.05, 8.08 (s, 1H), 11.02, 11.03 (s, 1H).

Intermediate 3: 2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide

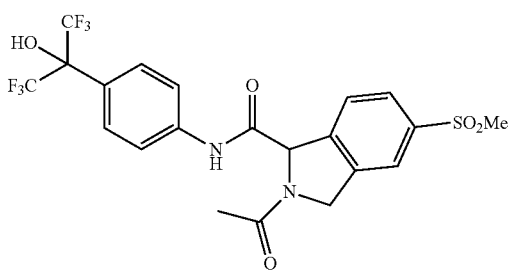 [SMILES: CC(=O)N1Cc2cc(S(C)(=O)=O)ccc2C1C(=O)Nc1ccc(C(O)(C(F)(F)F)C(F)(F)F)cc1]

Step 1: 2-(tert-Butoxycarbonyl)-5-(methylsulfonyl)isoindoline-1-carboxylic acid

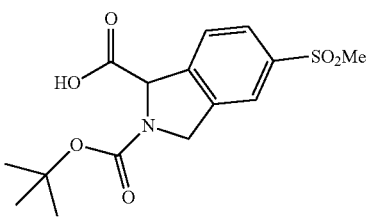 [SMILES: CC(C)(C)OC(=O)N1Cc2cc(S(C)(=O)=O)ccc2C1C(=O)O]

The hydrochloride salt of 5-(methylsulfonyl)isoindoline-1-carboxylic acid (7.78 g, 28 mmol) was dissolved in water (130 mL) and 1,4-dioxane (200 mL) and an aqueous solution of potassium carbonate (2M, 70.0 mL, 140.00 mmol) was added. Di-tert-butyl dicarbonate (6.11 g, 28 mmol) was added in one portion, and the solution was stirred at room temperature overnight. Dioxane was removed in vacuo and DCM (100 mL) was added. A black precipitate formed in the aqueous which was removed by filtration. The aqueous solution was washed a second time with DCM and the organic washes discarded. The aqueous solution was then chilled with stirring on an ice water bath before adding EtOAc (100 mL). The pH was gradually adjusted to 2 by the slow addition of chilled hydrochloric acid (3.8M). The biphasic mixture was stirred for a few min before the EtOAc phase was separated. The aqueous solution was washed with EtOAc (2×100 mL). The combined EtOAc extracts were washed with water (1×100 mL) and brine (50 mL). Drying over MgSO₄, filtration and concentration in vacuo afforded 2-(tert-butoxycarbonyl)-5-(methylsulfonyl)isoindoline-1-carboxylic acid (4.55 g, 47.5%) as solid. LC/MS: m/z=681 [2M−H]⁻. ¹H NMR (400 MHz, DMSO-d₆, mixture of rotamers, 1.6*:1) δ 1.41*, 1.46 (s, 9H), 3.21, 3.22* (s, 3H), 4.68-4.8 (m, 2H), 5.44 (s, 1H), 7.60*, 7.63 (d, 1H), 7.87-7.92 (m, 1H), 7.95, 7.98* (s, 1H).

Step 2: tert-Butyl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate

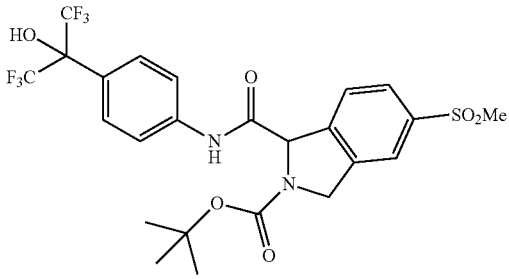 [SMILES: CC(C)(C)OC(=O)N1Cc2cc(S(C)(=O)=O)ccc2C1C(=O)Nc1ccc(C(O)(C(F)(F)F)C(F)(F)F)cc1]

2-(tert-Butoxycarbonyl)-5-(methylsulfonyl)isoindoline-1-carboxylic acid (4.40 g, 12.89 mmol) and 2-(4-aminophenyl)-1,1,1,3,3,3-hexafluoropropan-2-ol (3.34 g, 12.89 mmol) were combined in EtOAc (50 mL) to give a suspension, before the addition of triethylamine (5.39 mL, 38.67 mmol) gave a dark brown solution. The solution was chilled by stirring on an ice/water bath before the addition of T3P (50% in EtOAc, 15.35 mL, 25.78 mmol) through a dropping funnel. The addition was controlled to ensure that the temperature did not exceed 5° C. After one hour the reaction solution was washed with water (2×50 mL). The combined water washes were extracted with EtOAc (50 mL). The combined organic extracts were washed with 0.1M aq HCl (2×50 mL) and brine (25 mL) before being dried over MgSO$_4$. Filtration and concentration in vacuo gave a residue, which was purified by flash chromatography eluting with 0-60% EtOAc in n-heptane to give the title compound (4.95 g, 66%) as a solid.

LC/MS: m/z=581 [M–H]$^-$. $^1$H NMR (400 MHz, DMSO-d$_6$, mixture of rotamers, 1.8*:1) δ 1.35*, 1.47 (s, 9H), 3.20, 3.21* (s, 3H), 4.69-4.88 (m, 2H), 5.61*, 5.63 (s, 1H), 7.6-7.76 (m, 5H), 7.86-7.92 (m, 1H), 7.98, 8.01* (s, 1H), 8.63*, 8.65 (s, 1H), 10.75 (s, 1H).

Step 3: N-[4-(1,1,1,3,3,3-Hexafluoro-2-hydroxypropan-2-yl)phenyl]-5-(methylsulfonyl)-2,3-dihydro-1H-isoindole-1-carboxamide

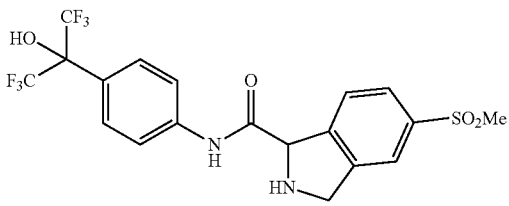 [SMILES: CS(=O)(=O)c1ccc2c(c1)CNC2C(=O)Nc1ccc(C(O)(C(F)(F)F)C(F)(F)F)cc1]

tert-Butyl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate (13.3 g, 22.83 mmol) was suspended in isopropyl acetate (50 mL). Hydrogen chloride in IPA (5N, 50 ml, 250 mmol) was added and the resulting mixture was stirred at rt overnight. The reaction was concentrated in vacuo and the residue was co-evaporated with EtOAc (2×50 ml) and EtOAc/n-Heptane (1:1 80 ml), and then dried under vacuum for 24 h. The hydrochloride salt of the title compound (10.73 g, 91%) was obtained as a solid and used without further purification.

A sample was purified by RP-HPLC (chromatographic conditions: gradient 5-95% ACN in 0.1M HCO$_2$H, pH3; Column: Waters Sunfire C18 ODB 5µ 19×150 mm).

HRMS: calculated for (C$_{19}$H$_{16}$F$_6$N$_2$O$_4$S+H)$^+$ 483.0813; found: (ESI [M+H]$^+$) 483.0811. $^1$H NMR (600 MHz, DMSO-d$_6$) δ 3.18 (s, 3H), 4.37 (d, 1H), 4.41 (d, 1H), 5.09 (s, 1H), 7.60 (d, 2H), 7.71 (d, 1H), 7.77-7.83 (m, 3H), 7.87 (s, 1H), 8.65 (s, 1H), 10.33 (s, 1H).

Step 4: 2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide

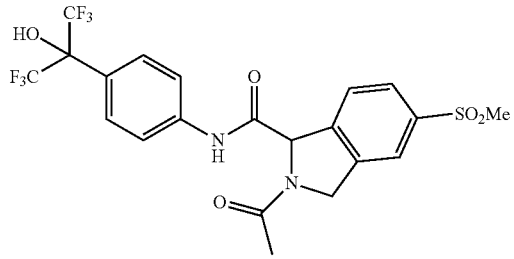 [SMILES: CC(=O)N1Cc2cc(S(C)(=O)=O)ccc2C1C(=O)Nc1ccc(C(O)(C(F)(F)F)C(F)(F)F)cc1]

N-[4-(1,1,1,3,3,3-Hexafluoro-2-hydroxypropan-2-yl)phenyl]-5-(methylsulfonyl)-2,3-dihydro-1H-isoindole-1-carboxamide (4.2 g, 8.71 mmol) was dissolved in DCM (150 mL) and to this triethylamine (2.427 mL, 17.41 mmol) and acetic acid (0.748 mL, 13.06 mmol) was added followed by T3P (50% in EtOAc, 10.37 mL, 17.41 mmol). The reaction was stirred at room temperature for 30 min. The reaction was partitioned between DCM and water, the layers were separated using a phase separator cartridge and the solvent was removed in vacuo.

The residue was purified on silica eluting with 50% to 100% EtOAc in heptane. Product fractions were combined, concentrated in vacuo to yield a gum. Trituration with diethyl ether provided a solid, which was isolated by filtration and washed with diethyl ether to afford 2-acetyl-N-[4-(1,1,1,3,3,3-hexafluoro-2-hydroxypropan-2-yl)phenyl]-5-(methylsulfonyl)-2,3-dihydro-1H-isoindole-1-carboxamide (3.32 g, 72.7%). HRMS: calculated for (C$_{21}$H$_{18}$F$_6$N$_2$O$_5$S+H)$^+$ 525.0919; found: (ESI [M+H]$^+$) 525.0927. $^1$H NMR (500 MHz, DMSO-d$_6$, mixture of rotamers, 4*:1) δ 1.99, 2.15* (s, 3H), 3.21, 3.22* (s, 3H), 4.76-4.94, 4.98-5.11* (m, 2H), 5.73*, 5.93 (s, 1H), 7.6-7.81 (m, 5H), 7.87-7.92 (m, 1H), 8.00*, 8.03 (s, 1H), 8.64*, 8.67 (s, 1H), 10.69*, 10.93 (s, 1H).

Intermediate 4: tert-Butyl 1-[[4-[1-cyano-2,2,2-trifluoro-1-(trifluoromethyl)ethyl]phenyl]carbamoyl]-5-methylsulfonyl-isoindoline-2-carboxylate

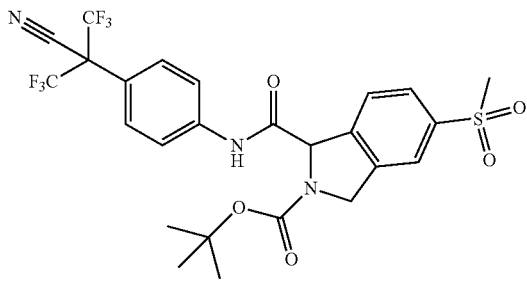 [SMILES: CC(C)(C)OC(=O)N1Cc2cc(S(C)(=O)=O)ccc2C1C(=O)Nc1ccc(C(C#N)(C(F)(F)F)C(F)(F)F)cc1]

2-(tert-Butoxycarbonyl)-5-(methylsulfonyl)isoindoline-1-carboxylic acid (product of Step 1 of the synthesis of Intermediate 3, 1.024 g, 3 mmol) was suspended in DCM (15 mL) and to this 2-(4-aminophenyl)-3,3,3-trifluoro-2-(trifluoromethyl)propanenitrile (Intermediate 1, 0.804 g, 3.00 mmol) and triethylamine (0.836 mL, 6.00 mmol) was added. To the resulting solution T3P (50% solution in EtOAc, 3.57 mL, 6.00 mmol) was then added. The reaction was stirred at room temperature for 1 h. The reaction was diluted with DCM and washed with aqueous HCl (0.5M). The layers were separated using a phase separator cartridge and concentrated in vacuo. The residue was purified by flash chromatography eluting with 30%-50% EtOAc in heptane to give the title compound (1.66 g, 94%) as a solid.

LC/MS: m/z=592 [M+H]$^+$. $^1$H NMR (400 MHz, DMSO-d$_6$, mixture of rotamers, 2*:1) δ 1.34*, 1.47 (s, 9H), 3.21, 3.22* (s, 3H), 4.7-4.9 (m, 2H), 5.62*, 5.64 (d, 1H), 7.59-7.8 (m, 3H), 7.84-7.95 (m, 3H), 7.99, 8.02* (s, 1H), 10.95 (s, 1H).

Intermediate 5: 9H-Fluoren-9-ylmethyl 1-[[4-[1-cyano-2,2,2-trifluoro-1-(trifluoromethyl)ethyl]phenyl]carbamoyl]-5-(cyclopropylmethylsulfonyl)isoindoline-2-carboxylate

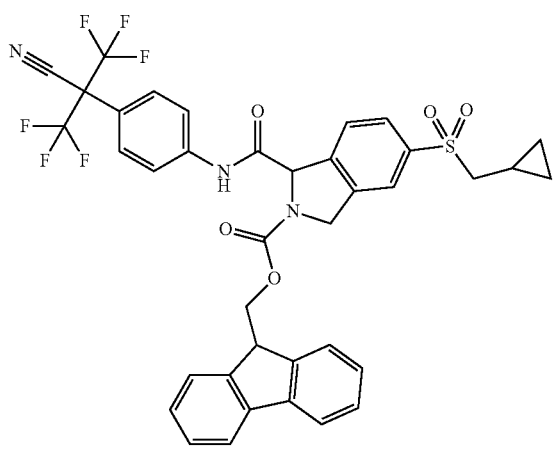 [SMILES: N#CC(c1ccc(NC(=O)C2c3ccc(S(=O)(=O)CC4CC4)cc3CN2C(=O)OCC2c3ccccc3-c3ccccc32)cc1)(C(F)(F)F)C(F)(F)F]

Step 1: Methyl 3-((1-oxoisoindolin-5-yl)thio)propanoate

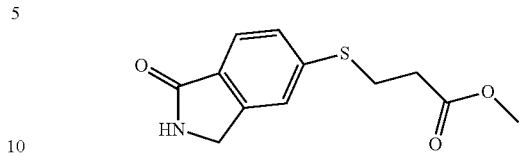

A solution of 5-bromoisoindolin-1-one (10 g, 47.16 mmol) in dioxane (450 mL) was degassed before Xantphos (2.73 g, 4.72 mmol), DIPEA (9.88 mL, 56.59 mmol), Pd$_2$(dba)$_3$ (2.159 g, 2.36 mmol) and methyl 3-mercaptopropanoate (32.6 mL, 330.12 mmol) was added. The reaction was heated to 80° C. for 1 h. The reaction was concentrated in vacuo. Approximately half of the material was purified by flash chromatography eluting with 0-5% methanol in EtOAc to afford 4.69 g of product. Only half the material was purified this way because the crude material solidified part way through loading onto the column. The solidified material was triturated with methanol and 4.48 g of product was collected by filtration as a colorless solid. The mother liquor was concentrated in vacuo and purified by flash chromatography eluting with 0-5% methanol in EtOAc to afford 1.1 g product. This was combined with the material from the first column to give 10.27 g (86%) of the title compound.

LC/MS: m/z=252 [M+H]$^+$. $^1$H NMR (500 MHz, DMSO-d$_6$) δ 2.69 (t, 2H), 3.26 (t, 2H), 3.60 (s, 3H), 4.34 (s, 2H), 7.38 (d, 1H), 7.52 (s, 1H), 7.58 (d, 1H), 8.48 (s, 1H).

Step 2: 5-((Cyclopropylmethyl)thio)isoindolin-1-one

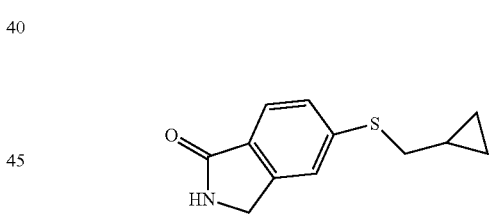

To a suspension of methyl 3-((1-oxoisoindolin-5-yl)thio) propanoate (5.79 g, 23.04 mmol) in THF (250 mL) was added potassium tert-butoxide (46.1 mL, 46.08 mmol, 1M solution in THF). The reaction was stirred for 5 min at room temperature, followed by addition of (bromomethyl)cyclopropane (6.22 g, 46.08 mmol). The reaction was stirred for 30 min at room temperature. The reaction was poured into water and the product extracted into EtOAc. The combined organic extracts were washed with brine, dried using a phase separator cartridge and concentrated in vacuo. The solid obtained was slurried in EtOAc, collected by filtration and then washed with diethyl ether to afford 5-((cyclopropylmethyl)thio)isoindolin-1-one (2.35 g, 46%).

LC/MS: m/z=220 [M+H]$^+$. $^1$H NMR (500 MHz, DMSO-d$_6$) δ 0.17-0.33 (m, 2H), 0.44-0.62 (m, 2H), 0.94-1.11 (m, 1H), 3.01 (d, 2H), 4.33 (s, 2H), 7.38 (d, 1H), 7.50 (s, 1H), 7.55 (d, 1H), 8.45 (s, 1H).

Step 3: tert-Butyl 5-((cyclopropylmethyl)thio)-1-oxoisoindoline-2-carboxylate

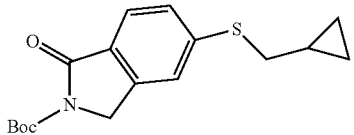 [SMILES: CC(C)(C)OC(=O)N1Cc2cc(SCC3CC3)ccc2C1=O]

5-((Cyclopropylmethyl)thio)isoindolin-1-one (4.13 g, 18.83 mmol) was suspended in ACN (150 mL) and DMAP (3.22 g, 26.37 mmol) was added in one portion. Di-tert-butyl dicarbonate (5.75 g, 26.37 mmol) was then added and the reaction stirred at room temperature for 20 min. The ACN was removed in vacuo. The residue was dissolved in EtOAc and washed with aqueous HCl (0.5M, 3×200 mL). The organic extract was dried using a phase separator cartridge and concentrated in vacuo. tert-Butyl 5-((cyclopropylmethyl)thio)-1-oxoisoindoline-2-carboxylate was obtained as a brown oil that solidified on standing. The material was used in the next step without further purification $^1$H NMR (500 MHz, DMSO-$d_6$) δ 0.23-0.34 (m, 2H), 0.5-0.6 (m, 2H), 1.00-1.13 (m, 1H), 1.51 (s, 9H), 3.04 (d, 2H), 4.73 (s, 2H), 7.41 (d, 1H), 7.55 (s, 1H), 7.64 (d, 1H).

Step 4: tert-Butyl 5-((cyclopropylmethyl)sulfonyl)-1-oxoisoindoline-2-carboxylate

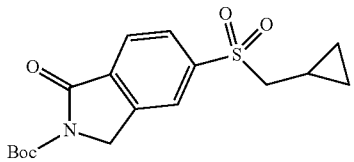 [SMILES: CC(C)(C)OC(=O)N1Cc2cc(S(=O)(=O)CC3CC3)ccc2C1=O]

tert-Butyl 5-((cyclopropylmethyl)thio)-1-oxoisoindoline-2-carboxylate (6.01 g, 18.83 mmol) was dissolved in DCM (200 mL) at rt and to this mCPBA (≥77%, 10.13 g, 45.19 mmol) was added (an exotherm of ca 36° C. was observed). The reaction was stirred at rt for 20 min. The reaction mixture was washed twice with 1M aqueous NaOH. The organic phase was dried using a phase separator cartridge and concentrated in vacuo to afford tert-butyl 5-((cyclopropylmethyl)sulfonyl)-1-oxoisoindoline-2-carboxylate (5.98 g, 90%) as a solid. The material was used in the next step without further purification.

LC/MS: m/z=350 [M−H]$^−$. $^1$H NMR (500 MHz, DMSO-$d_6$) δ 0.01-0.2 (m, 2H), 0.33-0.5 (m, 2H), 0.78-0.93 (m, 1H), 1.53 (s, 9H), 3.35 (d, 2H), 4.89 (s, 2H), 7.97-8.05 (m, 2H), 8.21 (s, 1H).

Step 5: tert-Butyl 5-((cyclopropylmethyl)sulfonyl)-1-hydroxyisoindoline-2-carboxylate

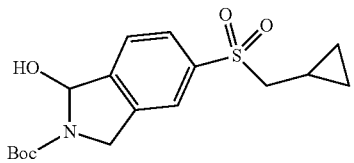 [SMILES: CC(C)(C)OC(=O)N1Cc2cc(S(=O)(=O)CC3CC3)ccc2C1O]

tert-Butyl 5-((cyclopropylmethyl)sulfonyl)-1-oxoisoindoline-2-carboxylate (5.48 g, 15.59 mmol) was dissolved in DCM (150 mL) and the mixture was cooled in an ice bath. DIBAL-H (26.5 mL, 26.51 mmol, 1M solution in THF) was added and the reaction stirred at this temperature for 15 min. Saturated aqueous Rochelle's salt (100 ml) was added and the resultant mixture was stirred for 20 min whilst warming to rt. DCM (150 mL) was added and the layers separated. The aqueous layer was extracted with DCM. The combined organic extracts were dried using a phase separator cartridge and concentrated in vacuo. The product was obtained as a pink gum/foam. The material was used as such in the next step.

LC/MS: m/z=352 [M−H]$^−$.

Step 6: tert-Butyl 5-((cyclopropylmethyl)sulfonyl)-1-methoxyisoindoline-2-carboxylate

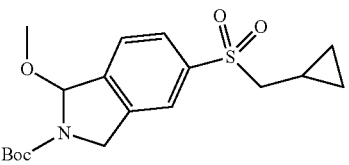 [SMILES: COC1c2ccc(S(=O)(=O)CC3CC3)cc2CN1C(=O)OC(C)(C)C]

tert-Butyl 5-((cyclopropylmethyl)sulfonyl)-1-hydroxyisoindoline-2-carboxylate (5.51 g, 15.59 mmol) was dissolved in MeOH (110 mL) and to this PPTs (0.392 g, 1.56 mmol) was added and the reaction stirred at rt. After 20 min LCMS indicated complete consumption of the starting material. The reaction was quenched by addition of triethylamine (34.8 mL, 249.44 mmol) and concentrated in vacuo to afford a dark purple oil. This was used without further purification in the next step.

Step 7: tert-butyl 1-cyano-5-((cyclopropylmethyl)sulfonyl)isoindoline-2-carboxylate

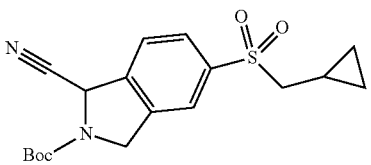 [SMILES: CC(C)(C)OC(=O)N1Cc2cc(S(=O)(=O)CC3CC3)ccc2C1C#N]

tert-Butyl 5-((cyclopropylmethyl)sulfonyl)-1-methoxyisoindoline-2-carboxylate (5.73 g, 15.59 mmol) was dissolved in DCM (110 mL). This resulting mixture was cooled to −78° C. before TMSCN (3.14 mL, 23.39 mmol) and BF$_3$.OEt$_2$ (2.96 mL, 23.39 mmol) was added. The reaction was stirred at −78° C. for 15 min. A saturated aqueous solution of NaHCO₃ and DCM was added and the reaction allowed to warm to rt. The two layers were separated and the aqueous extracted with DCM. The combined organic extracts were dried using a phase separator cartridge and concentrated in vacuo. The residue was purified on silica eluting with 25-50% EtOAc in heptane. tert-Butyl 1-cyano-5-((cyclopropylmethyl)sulfonyl)isoindoline-2-carboxylate (3.22 g, 57%) was obtained as a pale pink foam.

LC/MS: m/z=361 [M−H]⁻. ¹H NMR (500 MHz, DMSO-d₆) δ 0.06-0.16 (m, 2H), 0.33-0.53 (m, 2H), 0.7-0.95 (m, 1H), 1.49, 1.51 (s, 9H), 3.27-3.31 (m, 2H), 4.75, 4.77 (s, 2H), 6.18, 6.20 (s, 1H), 7.82, 7.84 (s, 1H), 7.94, 7.96 (s, 1H), 7.97, 7.99 (s, 1H).

Step 8: 5-((Cyclopropylmethyl)sulfonyl)isoindoline-1-carboxylic acid, hydrochloride salt

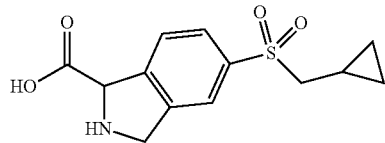 [SMILES: O=C(O)C1NCc2cc(S(=O)(=O)CC3CC3)ccc21]

6M aqueous HCl (35 ml, 210.00 mmol) was added to tert-butyl 1-cyano-5-((cyclopropylmethyl)sulfonyl)isoindoline-2-carboxylate (3.48 g, 9.60 mmol) and the mixture heated at 70° C. for 2.5 h. The reaction was cooled to rt and concentrated to dryness in vacuo. The dark solid obtained was used crude in the next step.

LC/MS: m/z=280 [M−H]⁻.

Step 9: 5-[(Cyclopropylmethyl)sulfonyl]-2-[(9H-fluoren-9-ylmethoxy)carbonyl]-2,3- dihydro-1H-isoindole-1-carboxylic acid

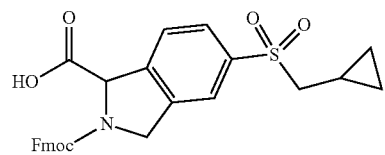

To 5-((cyclopropylmethyl)sulfonyl)isoindoline-1-carboxylic acid, hydrochloride salt (3.05 g, 9.6 mmol) in dioxane (70 mL)/water (70 mL) was added potassium carbonate (6.63 g, 48.00 mmol) and 9-fluorenylmethyl chloroformate (2.235 g, 8.64 mmol). The reaction was stirred at rt overnight. The dioxane was removed in vacuo. The aqueous was then acidified with 1M aqueous HCl and extracted with EtOAc. The organic extracts were combined, dried using a phase separator cartridge and concentrated in vacuo. The material was used as such in the next step.

LC/MS: m/z=504 [M+H]⁺.

Step 10: 9H-Fluoren-9-ylmethyl 1-[[4-[1-cyano-2,2,2-trifluoro-1-

(trifluoromethyl)ethyl]phenyl]carbamoyl]-5-(cyclopropylmethylsulfonyl)isoindoline-2-carboxylate

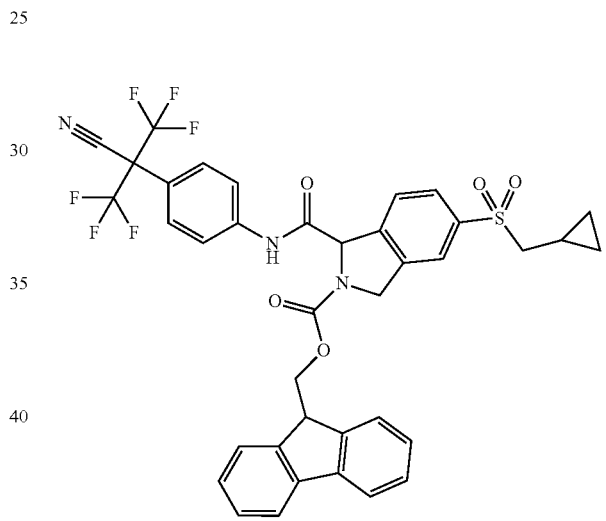

T3P (50% solution in EtOAc, 1.143 mL, 1.92 mmol) was added to a mixture of 5-[(cyclopropylmethyl)sulfonyl]-2-[(9H-fluoren-9-ylmethoxy)carbonyl]-2,3-dihydro-1H-isoindole-1-carboxylic acid (483 mg, 0.96 mmol), 2-(4-aminophenyl)-3,3,3-trifluoro-2-(trifluoromethyl)propanenitrile (Intermediate 1, 206 mg, 0.77 mmol) and triethylamine (0.268 mL, 1.92 mmol) in DCM (10 mL). This was stirred at rt for 30 min. The reaction mixture was washed with water and the layers separated using a phase separator cartridge. The DCM was removed in vacuo and the residue purified by flash chromatography eluting with 30-40% EtOAc in heptane to give the title compound (310 mg, 42.8%) as a solid.

LC/MS: m/z=754 [M+H]⁺. ¹H NMR (500 MHz, DMSO-d₆, mixture of rotamers, 1:1) δ 0.08-0.18 (m, 2H), 0.42-0.53 (m, 2H), 0.78-0.88 (m, 1H), 3.2-3.3 (m, 2H), 4.15-4.4 (m, 3H), 4.85-5.05, (m, 2H), 5.74, 5.79 (s, 1H), 6.94-7 (m, 1H), 7.23, 7.30 (t, 1H), 7.33-7.47 (m, 2H), 7.57, 7.58 (s, 1H), 7.66-7.82 (m, 5H), 7.87-7.96 (m, 4H), 8.02, 8.04 (s, 1H), 11.02, 11.03 (s, 1H).

Intermediate 6: tert-Butyl 1-[[4-[1-cyano-2,2,2-trifluoro-1-(trifluoromethyl)ethyl]phenyl]carbamoyl]-5-ethylsulfonyl-isoindoline-2-carboxylate

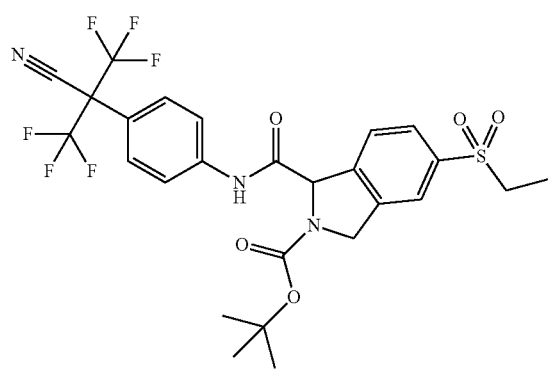 [SMILES: CCS(=O)(=O)c1ccc2c(c1)CN(C(=O)OC(C)(C)C)C2C(=O)Nc1ccc(C(C#N)(C(F)(F)F)C(F)(F)F)cc1]

Step 1: 5-(Ethylthio)isoindolin-1-one

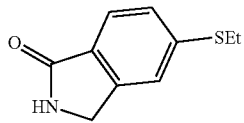

5-Bromoisoindolin-1-one (10 g, 47.16 mmol) and sodium ethanethiolate (9.92 g, 117.90 mmol) were mixed together in DMF (100 mL) and the reaction heated to 100° C. for 20 min. The reaction was cooled to rt, poured into water (100 mL) and the product extracted with EtOAc (3×200 mL). The combined organic extracts were washed with brine (4×50 mL). LCMS indicated product in the aqueous washings, and consequently they were combined and extracted with EtOAc (4×50 mL). The organic extracts were combined, dried using a phase separator cartridge and concentrated in vacuo. The solid obtained was dried under high vacuum overnight. 5-(Ethylthio)isoindolin-1-one (8.68 g, 95%) was obtained as a yellow solid. The material was used in the next step without further purification.

LC/MS: m/z=194 [M+H]$^+$. $^1$H NMR (500 MHz, DMSO-d$_6$) δ 1.27 (t, 3H), 3.06 (q, 2H), 4.33 (s, 2H), 7.36 (dd, 1H), 7.47-7.48 (m, 1H), 7.57 (d, 1H), 8.45 (s, 1H).

Step 2: tert-Butyl 5-(ethylthio)-1-oxoisoindoline-2-carboxylate

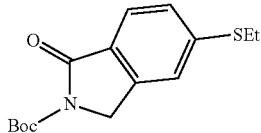

5-(Ethylthio)isoindolin-1-one (8.68 g, 44.91 mmol) was suspended in ACN (400 mL) and DMAP (7.68 g, 62.88 mmol) was added in one portion. After 10 min di-tert-butyl dicarbonate (13.72 g, 62.88 mmol) was added and the mixture was stirred at rt for 30 min. The reaction was concentrated in vacuo. The residue was dissolved in EtOAc and washed with 0.1M aqueous HCl (4×100 mL). The organic extract was dried using a phase separator cartridge and concentrated in vacuo to afford tert-butyl 5-(ethylthio)-1-oxoisoindoline-2-carboxylate (12.50 g, 95%) as an orange solid. The material was used in the next step without further purification. $^1$H NMR (500 MHz, DMSO-d$_6$) δ 1.29 (t, 3H), 1.51 (s, 9H), 3.09 (q, 2H), 4.74 (s, 2H), 7.39 (dd, 1H), 7.52-7.53 (m, 1H), 7.65 (d, 1H).

Step 3: tert-Butyl 5-(ethylsulfonyl)-1-oxoisoindoline-2-carboxylate

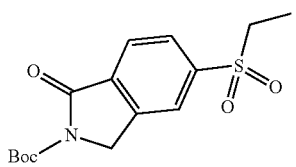 [SMILES: CCS(=O)(=O)c1ccc2c(c1)CN(C(=O)OC(C)(C)C)C2=O]

tert-Butyl 5-(ethylthio)-1-oxoisoindoline-2-carboxylate (13.18 g, 44.91 mmol) was dissolved in DCM (500 mL) at room temperature and to this mixture, mCPBA (≥77%, 24.16 g, 107.78 mmol) was added portion wise (an increase of the temperature to ca 35° C. was observed). The reaction was stirred at rt for 30 min. The reaction was washed twice with 1M aqueous NaOH and the DCM phase was dried using a phase separator cartridge and concentrated in vacuo. tert-Butyl 5-(ethylsulfonyl)-1-oxoisoindoline-2-carboxylate (14.00 g, 96%) was obtained as a yellow solid. The material was used in the next step without purification.

LC/MS: m/z=324 [M−H]$^−$. $^1$H NMR (500 MHz, DMSO-d$_6$) δ 1.12 (t, 3H), 1.53 (s, 9H), 3.38 (q, 2H), 4.89 (s, 2H), 7.99-8.04 (m, 2H), 8.21 (s, 1H).

Step 4: tert-Butyl 5-(ethylsulfonyl)-1-hydroxyisoindoline-2-carboxylate

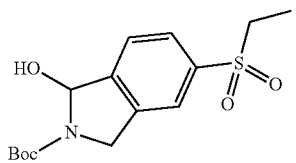 [SMILES: CCS(=O)(=O)c1ccc2c(c1)CN(C(=O)OC(C)(C)C)C2O]

tert-Butyl 5-(ethylsulfonyl)-1-oxoisoindoline-2-carboxylate (12 g, 36.88 mmol) was dissolved in DCM (300 mL) and the mixture was cooled in an ice bath. DIBAL-H (63 mL, 63.00 mmol, 1M solution in THF) was added and the reaction stirred at this temperature for 15 min. Saturated aqueous Rochelle's salt (300 mL) was added and the mixture stirred for 20 min. DCM (300 mL) was added and the layers separated. The aqueous phase was extracted with DCM. The combined organic extracts were dried using a phase separator cartridge and concentrated in vacuo. The material was used crude in the next step.

LC/MS: m/z=326 [M−H]$^−$.

Step 5: tert-Butyl 5-(ethylsulfonyl)-1-methoxyisoindoline-2-carboxylate

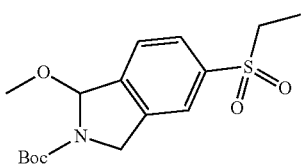 [SMILES: CCS(=O)(=O)c1ccc2c(c1)CN(C(=O)OC(C)(C)C)C2OC]

tert-Butyl 5-(ethylsulfonyl)-1-hydroxyisoindoline-2-carboxylate (12.07 g, 36.88 mmol) was dissolved in MeOH (210 mL) and to this PPTs (0.927 g, 3.69 mmol) was added and the reaction stirred at rt. After 20 min LCMS indicated that no starting material remained. The reaction was quenched by addition of triethylamine (81 mL, 581.14 mmol) and concentrated in vacuo to afford a dark purple oil. This was used without further purification in the next step.

Step 6: tert-Butyl 1-cyano-5-(ethylsulfonyl)isoindoline-2-carboxylate

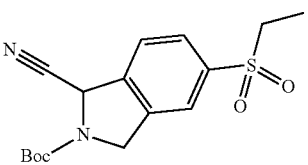 [SMILES: CCS(=O)(=O)c1ccc2c(c1)CN(C(=O)OC(C)(C)C)C2C#N]

tert-Butyl 5-(ethylsulfonyl)-1-methoxyisoindoline-2-carboxylate (12.59 g, 36.88 mmol) was dissolved in DCM (300 mL) and the solution cooled to −78° C. TMSCN (7.42 mL, 55.32 mmol) and then BF$_3$·OEt$_2$ (7.01 mL, 55.32 mmol) was added. The reaction was stirred at −78° C. for 15 min. Saturated aqueous NaHCO$_3$ solution (300 mL) and DCM (300 mL) were added and the reaction allowed to warm to rt. The two layers were separated and the aqueous extracted with DCM. The combined organic extracts were dried using a phase separator cartridge and concentrated in vacuo. The material was purified by flash chromatography eluting with 40% EtOAc in heptane. tert-Butyl 1-cyano-5-(ethylsulfonyl) isoindoline-2-carboxylate (7.58 g, 61.1%) was obtained as a solid.

LC/MS: m/z=335 [M−H]$^-$. $^1$H NMR (500 MHz, DMSO-d$_6$, mixture of rotamers, 1:1) δ 1.11 (t, 3H), 1.49, 1.51 (s, 9H), 3.29-3.36 (m, 2H), 4.75, 4.77 (s, 2H), 6.18, 6.20 (s, 1H), 7.83, 7.85 (s, 1H), 7.93, 7.95 (s, 1H), 7.96, 7.99 (s, 1H).

Step 7: 2-tert-Butoxycarbonyl-5-ethylsulfonyl-isoindoline-1-carboxylic acid

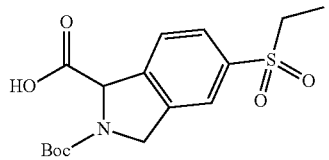 [SMILES: CCS(=O)(=O)c1ccc2c(c1)CN(C(=O)OC(C)(C)C)C2C(=O)O]

A 5 M aqueous solution of NaOH (1 ml, 5.00 mmol) was added to tert-butyl 1-cyano-5-(ethylsulfonyl)isoindoline-2-carboxylate (0.052 g, 0.156 mmol) and the reaction mixture was stirred at 60° C. for 3 h. The mixture was still a suspension so NaOH (1 mL, 5.00 mmol) was added and the mixture heated at 60° C. overnight. The reaction was acidified and the products extracted into EtOAc. The combined organic extracts were dried using a phase separator cartridge and concentrated in vacuo. The residue was used crude in the coupling reaction LC/MS: m/z=256 [M+H−BOC]$^+$.

Step 8: tert-Butyl 1-((4-(2-cyano-1,1,1,3,3,3-hexafluoropropan-2-yl)phenyl)carbamoyl)-5-(ethylsulfonyl)isoindoline-2-carboxylate (Intermediate 6)

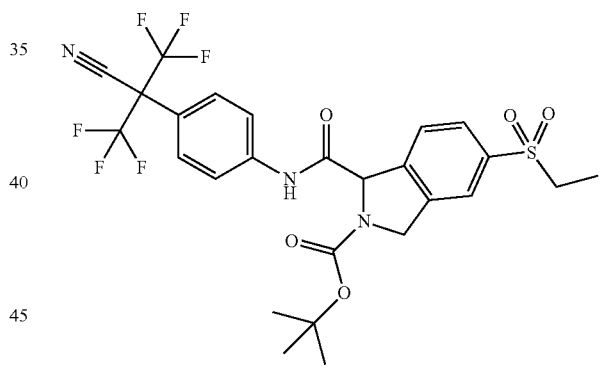

To a mixture of 2-(tert-butoxycarbonyl)-5-(ethylsulfonyl) isoindoline-1-carboxylic acid (product of step 7 of the synthesis of Intermediate 6, 0.141 g, 0.40 mmol), 2-(4-aminophenyl)-3,3,3-trifluoro-2-(trifluoromethyl)propanenitrile (Intermediate 1, 0.085 g, 0.32 mmol) and triethylamine (0.110 mL, 0.79 mmol) in DCM (4 mL) was added T3P (50% solution in EtOAc, 0.283 mL, 0.48 mmol). The reaction was stirred at rt for 30 min. The reaction was partitioned between DCM and water, the layers were separated using a phase separator cartridge and the solvent was removed in vacuo. The residue was dissolved in methanol and loaded onto an Isolute™ SCX cartridge (previously flushed with methanol). The product was eluted with methanol. The methanol was removed in vacuo and the residue was purified by flash chromatography eluting with 30% EtOAc in heptane. The title compound (0.060 g, 25%) was obtained as a solid, which was used without further purification.

LC/MS: m/z=606 [M+H]$^+$.

Intermediate 7: tert-Butyl 5-methylsulfonyl-1-[[4-[2,2,2-trifluoro-1-(2-methyltetrazol-5-yl)-1-(trifluoromethyl)ethyl]phenyl]carbamoyl]isoindoline-2-carboxylate

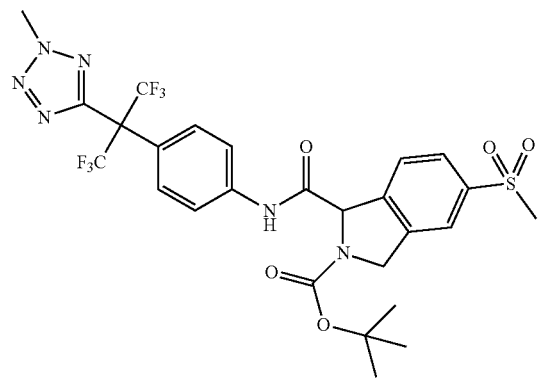 [SMILES: Cn1nnc(C(c2ccc(NC(=O)C3c4ccc(S(C)(=O)=O)cc4CN3C(=O)OC(C)(C)C)cc2)(C(F)(F)F)C(F)(F)F)n1]

Step 1: tert-Butyl N-[4-[2,2,2-trifluoro-1-(2H-tetrazol-5-yl)-1-(trifluoromethyl)ethyl]phenyl]carbamate

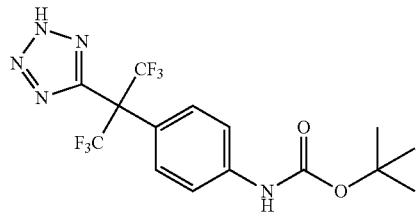 [SMILES: CC(C)(C)OC(=O)Nc1ccc(C(c2nn[nH]n2)(C(F)(F)F)C(F)(F)F)cc1]

Sodium azide (238 mg, 3.67 mmol) and ammonium chloride (196 mg, 3.67 mmol) was added to a solution of tert-butyl (4-(2-cyano-1,1,1,3,3,3-hexafluoropropan-2-yl)phenyl)carbamate (270 mg, 0.73 mmol) in anhydrous DMF (5 mL). This was heated to 100° C. for 20 min. The reaction mixture was partitioned between EtOAc and water and the pH of the aqueous adjusted to pH2 with 1M aqueous HCl. The layers were separated and the aqueous layer extracted twice more with EtOAc. The combined organic extracts were dried using a phase separator cartridge and concentrated in vacuo. A solution of the product in ca 1 ml of DMF (90% pure by LCMS) was obtained and this was used directly in the next step. The yield was assumed to be quantitative.

LC/MS: m/z=410 [M−H]⁻.

Step 2: tert-Butyl N-[4-[2,2,2-trifluoro-1-(2-methyltetrazol-5-yl)-1-(trifluoromethyl)ethyl]phenyl]carbamate DMF (5 mL) was added to tert-butyl (4-(1,1,1,3,3,3-hexafluoro-2-(2H-tetrazol-5-yl)propan-2-yl)phenyl)carbamate (product of step 1 of the synthesis of Intermediate 7, 300 mg, 0.73 mmol) in ca 1 ml DMF from the previous step. To this K₂CO₃ (111 mg, 0.80 mmol) and MeI (0.050 mL, 0.80 mmol) was added and the reaction stirred for 2 h. LCMS indicated SM remained consequently MeI (0.023 mL, 0.37 mmol) was added and the reaction was stirred overnight at rt. The reaction was partitioned between EtOAc and water. The aqueous was extracted twice with EtOAc and then the combined organics washed twice with brine. The organic extract was then dried using a phase separator cartridge and concentrated in vacuo. The residue was purified on silica eluting with 0-20% diethyl ether in heptane. tert-Butyl N-[4-[2,2,2-trifluoro-1-(2-methyltetrazol-5-yl)-1-(trifluoromethyl)ethyl]phenyl]carbamate (200 mg, 65%) was obtained.

LC/MS: m/z=424 [M−H]⁻. ¹H NMR (600 MHz, DMSO-d₆) δ 1.47 (s, 9H), 4.49 (s, 3H), 7.13 (d, 2H), 7.53 (d, 2H), 9.61 (s, 1H).

Step 3: 4-[2,2,2-Trifluoro-1-(2-methyltetrazol-5-yl)-1-(trifluoromethyl)ethyl]aniline tert-Butyl (4-(1,1,1,3,3,3-hexafluoro-2-(2-methyl-2H-tetrazol-5-yl)propan-2-yl)phenyl)carbamate (product of step 2 of the synthesis of Intermediate 7, 80 mg, 0.19 mmol) was dissolved in DCM (2 mL) and to this TFA (1 mL, 12.98 mmol) was added and the reaction was stirred at rt for 2 h. The reaction was concentrated in vacuo and the residue obtained was dissolved in methanol. This was loaded onto a 5 g SCX™ cartridge (previously flushed with methanol). The cartridge was flushed with methanol and then the product was eluted with 7M NH₃ in methanol. The methanolic ammonia was removed in vacuo to afford 4-(1,1,1,3,3,3-hexafluoro-2-(2-methyl-2H-tetrazol-5-yl)propan-2-yl)aniline (25.00 mg, 40.9%) as a solid.

LC/MS: m/z=324 [M−H]⁻. ¹H NMR (600 MHz, DMSO-d₆) δ 4.48 (s, 3H), 5.53 (s, 2H), 6.52-6.59 (m, 2H), 6.80 (d, 2H).

Step 4: tert-Butyl 5-methylsulfonyl-1-[[4-[2,2,2-trifluoro-1-(2-methyltetrazol-5-yl)-1-(trifluoromethyl)ethyl]phenyl]carbamoyl]isoindoline-2-carboxylate

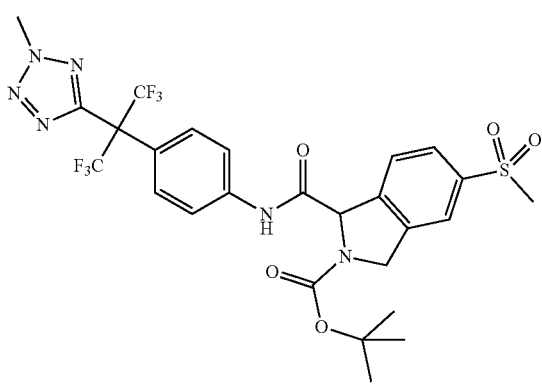 [SMILES: Cn1nnc(C(c2ccc(NC(=O)C3c4ccc(S(C)(=O)=O)cc4CN3C(=O)OC(C)(C)C)cc2)(C(F)(F)F)C(F)(F)F)n1]

2-(tert-Butoxycarbonyl)-5-(methylsulfonyl)isoindoline-1-carboxylic acid (product of Step 1 of the synthesis of Intermediate 3, 26.2 mg, 0.08 mmol) was suspended in DCM (1 mL) and to this was added 4-(1,1,1,3,3,3-hexafluoro-2-(2-methyl-2H-tetrazol-5-yl)propan-2-yl)aniline (product of step 3 of the synthesis of Intermediate 7, 25 mg, 0.08 mmol) and triethylamine (0.021 mL, 0.15 mmol). T3P (50% solution in EtOAc, 0.092 mL, 0.15 mmol) was then added. The reaction was stirred at rt for 30 min. The reaction was diluted with DCM and washed with 0.5M aqueous HCl. The layers were separated using a phase separator cartridge and concentrated in vacuo. The crude product was used without further purification.

LC/MS: m/z=647 [M−H]⁻.

Intermediate 8: tert-Butyl 1-[[4-[3-methoxy-3-oxo-1,1-bis(trifluoromethyl)propyl]phenyl]carbamoyl]-5-methylsulfonyl-isoindoline-2-carboxylate

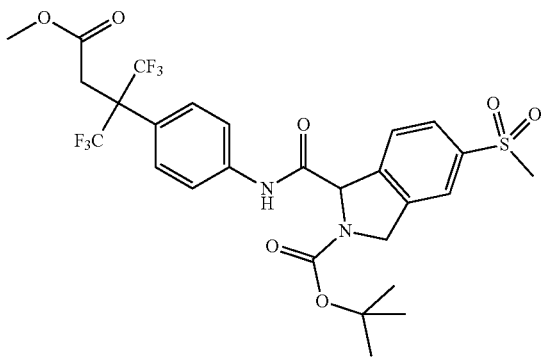 [SMILES: COC(=O)CC(c1ccc(NC(=O)C2c3ccc(S(C)(=O)=O)cc3CN2C(=O)OC(C)(C)C)cc1)(C(F)(F)F)C(F)(F)F]

Step 1: Dimethyl 2-[1-[4-(tert-butoxycarbonylamino)phenyl]-2,2,2-trifluoro-1-(trifluoromethyl)ethyl]propanedioate

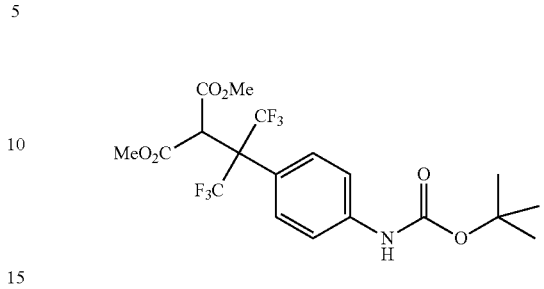

To a solution of tert-butyl (4-(1,1,1,3,3,3-hexafluoro-2-hydroxypropan-2-yl)phenyl)carbamate (product of Step 1 of the synthesis of Intermediate 1, 100 mg, 0.28 mmol) in DCM (2 mL), Et₃N (0.097 mL, 0.70 mmol) was added followed by methanesulfonic anhydride (72.7 mg, 0.42 mmol) and the reaction mixture was stirred at rt for 30 min. In another reaction vial dimethyl malonate (110 mg, 0.84 mmol) in DMF (0.4 mL) was treated with potassium 2-methylpropan-2-olate (94 mg, 0.84 mmol) at rt for 30 min (a solid was formed). After addition of DMF (0.6 mL) the material was added to the first reaction mixture and stirred at rt for 30 min. LCMS indicated that the desired product was formed. The reaction mixture was partitioned between EtOAc (100 mL) and water (10 mL). The layers were separated in a phase separator. The organic layer was washed with water (2×10 mL), dried over Na₂SO₄, filtered and the filtrate was concentrated in vacuo. The residue was purified by flash chromatography on silica (0-20% EtOAc in heptane). The fractions containing the desired product were collected and concentrated in vacuo to give the title compound (60 mg, 45%). LC/MS: m/z=472 [M−H]⁻. ¹H NMR (500 MHz, DMSO-d₆) δ 1.47 (s, 9H), 3.63 (s, 6H), 5.24 (s, 1H), 7.45-7.51 (m, 4H), 9.58 (s, 1H).

Alternatively, dimethyl 2-[1-[4-(tert-butoxycarbonylamino)phenyl]-2,2,2-trifluoro-1-(trifluoromethyl)ethyl]propanedioate could be prepared as described below.

A solution of 2-(4-((tert-butoxycarbonyl)amino)phenyl)-1,1,1,3,3,3-hexafluoropropan-2-yl methanesulfonate (24.35 g, 55.67 mmol) was prepared by slowly adding methanesulfonic anhydride (29.1 g, 167.01 mmol) to a chilled solution (ice/water bath) of triethylamine (23.15 mL, 167.01 mmol) and tert-butyl (4-(1,1,1,3,3,3-hexafluoro-2-hydroxypropan-2-yl)phenyl)carbamate (product of step 1 of the synthesis of Intermediate 1, 20 g, 55.67 mmol) in anhydrous ACN (180 mL) over 5 min. The solution was stirred for a further 10 min before the ice/water bath was removed and the dark orange solution was allowed to warm to rt.

Using a Vapourtec R2C+/R4 flow chemistry platform, a pumped solution (flow rate 0.667 mL/min) of DBU (41.6 mL, 278.35 mmol) in anhydrous ACN (200 mL) was combined with a pumped solution (flow rate 0.667 mL/min) of dimethyl malonate (31.8 mL, 278.35 mmol) in anhydrous ACN (200 mL). The combined solution was reacted in 2×10 mL PFA tube reactors at 25° C. (residence time 15 min) before the mesylate solution (flow rate of 0.667 mL/min) was introduced. The combined solution was reacted in 2×10 mL PFA tube reactors at 50° C. (residence time 10 min). The reaction solution was collected in a single fraction. Water (500 mL) was added and the bulk of the ACN was removed under reduced pressure. The solution was acidified by the addition of 3.8M aqueous HCl (25 mL) and the crude product was extracted into EtOAc (500 mL). The upper organic phase was separated and washed consecutively with aqueous HCl (0.1M, 250 mL), saturated aqueous NaHCO₃ (2×250 mL) and brine (75 mL), before drying over MgSO₄. The solution was filtered and concentrated under reduced pressure to afford Dimethyl-2-(2-(4-((tert-butoxycarbonyl)amino)phenyl)-1,1,1,3,3,3-hexafluoropropan-2-yl)malonate (13.95 g, 53%) as a colourless solid by automated flash column chromatography on a Biotage® KP-SIL 340 g column, using a gradient of 10% to 30% EtOAc in heptane as mobile phase.

LC/MS: m/z=472 [M–H]⁻. ¹H-NMR (400 MHz, CDCl₃) δ 1.52 (s, 9H), 3.70 (s, 6H), 4.73 (s, 1H), 6.55 (s, 1H), 7.35-7.56 (m, 4H). ¹⁹F-NMR (376 MHz, CDCl₃) δ −62.59.

Step 2: 3-[4-(tert-Butoxycarbonylamino)phenyl]-4,4,4-trifluoro-3-(trifluoromethyl)butanoic acid

To a solution of dimethyl 2-(2-(4-((tert-butoxycarbonyl)amino)phenyl)-1,1,1,3,3,3-hexafluoropropan-2-yl)malonate (product of step 1 of the synthesis of Intermediate 8, 171 mg, 0.36 mmol) in MeOH (3 mL), aqueous NaOH (0.9 mL, 1.81 mmol) was added and the reaction mixture was stirred at rt for 4 h. LCMS indicated that desired product was formed. The pH of the reaction mixture was adjusted to ca. 2 by addition of diluted HCl on an ice-water bath. The reaction mixture was extracted with EtOAc (1×100 mL). The organic layer was washed with water (1×10 mL), dried over Na₂SO₄, filtered and the filtrate was concentrated in vacuo to give crude title compound (145 mg, 98%), which was used without further purification in the next step.

LC/MS: m/z=401 [M–H]⁻. ¹H NMR (500 MHz, DMSO-d₆) δ 1.48 (s, 9H), 3.44 (s, 2H), 7.43-7.57 (m, 4H), 9.54 (s, 1H), 12.68 (br.s, 1H).

Step 3: Methyl 3-[4-(tert-butoxycarbonylamino)phenyl]-4,4,4-trifluoro-3-(trifluoromethyl)butanoate

To a solution of 3-(4-((tert-butoxycarbonyl)amino)phenyl)-4,4,4-trifluoro-3-(trifluoromethyl)butanoic acid (product of step 2 of the synthesis of Intermediate 8, 335 mg, 0.83 mmol) in DMF (6 mL), Na₂CO₃ (354 mg, 3.34 mmol) was added followed by iodomethane (0.156 mL, 2.50 mmol) and the reaction mixture was stirred at rt over night. The reaction mixture was partitioned between EtOAc (200 mL) and water (20 mL). The layers were separated in a phase separator. The organic layer was washed with water (2×25 mL), dried over Na₂SO₄, filtered and the filtrate was concentrated in vacuo to give the crude product (316 mg, 91%), which was used without further purification.

LC/MS: m/z=414 [M–H]⁻. ¹H NMR (500 MHz, DMSO-d₆); δ 1.48 (s, 9H); 3.55 (s, 3H); 3.56 (s, 2H); 7.39-7.65 (m, 4H); 9.56 (s, 1H).

Step 4: Methyl 3-(4-aminophenyl)-4,4,4-trifluoro-3-(trifluoromethyl)butanoate

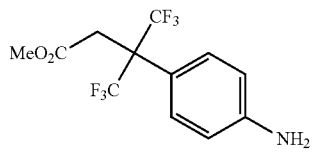

To a solution of methyl 3-(4-((tert-butoxycarbonyl)amino)phenyl)-4,4,4-trifluoro-3-(trifluoromethyl)butanoate (product of step 3 of the synthesis of Intermediate 8, 312 mg, 0.75 mmol) in DCM (6 mL), TFA (1.5 mL, 19.47 mmol) was added and the resulting solution was stirred at rt for 35 min. The volatiles were removed in vacuo. The residue was dissolved in EtOAc (200 mL), washed with aqueous saturated NaHCO₃ solution (2×20 mL). The organic layer was dried over Na₂SO₄, filtered and the filtrate was concentrated in vacuo to give the title compound as a crude (217 mg, 92%) which was used in the next step without further purification. ¹H NMR (500 MHz, DMSO-d₆); δ 3.45 (s, 2H); 3.55 (s, 3H); 5.50 (br.s, 2H); 6.59 (d, 2H); 7.24 (d, 2H).

Step 5: tert-Butyl 1-[[4-[3-methoxy-3-oxo-1,1-bis(trifluoromethyl)propyl]phenyl]carbamoyl]-5-methylsulfonyl-isoindoline-2-carboxylate

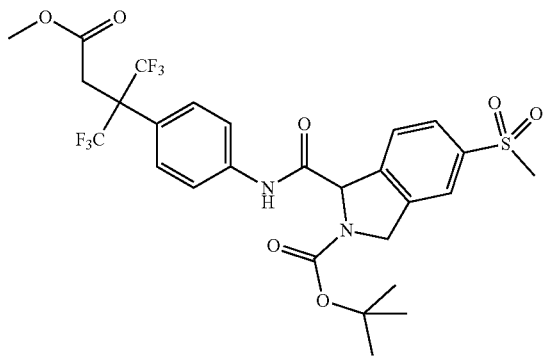 [SMILES: COC(=O)CC(c1ccc(NC(=O)C2c3ccc(S(C)(=O)=O)cc3CN2C(=O)OC(C)(C)C)cc1)(C(F)(F)F)C(F)(F)F]

To a mixture of methyl 3-(4-aminophenyl)-4,4,4-trifluoro-3-(trifluoromethyl)butanoate (214 mg, 0.68 mmol) and 2-(tert-butoxycarbonyl)-5-(methylsulfonyl)isoindoline-1-carboxylic acid (product of step 1 of the synthesis of Intermediate 3, 232 mg, 0.68 mmol) in EtOAc (4 mL), Et₃N (0.284 mL, 2.04 mmol) was added followed by T3P (50% in EtOAc) (0.808 mL, 1.36 mmol) in portions. After addition was completed the reaction mixture was stirred at rt for 40 min. The reaction mixture was partitioned between EtOAc (200 mL) and water (25 mL). The layers were separated using a phase separator. The organic layer was washed further with water (2×25 mL), dried over Na₂SO₄, filtered and the filtrate was concentrated in vacuo to give the title compound as a crude (364 mg, 84%) which was used directly in the next step without further purification.

LC/MS: m/z=637 [M–H]⁻.

Intermediate 9: tert-Butyl 1-[[4-[3-fluoro-1,1-bis(trifluoromethyl)propyl]phenyl]carbamoyl]-5-methylsulfonyl-isoindoline-2-carboxylate

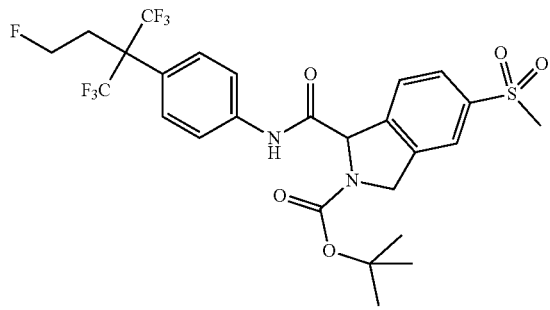 [SMILES: CC(C)(C)OC(=O)N1Cc2cc(S(C)(=O)=O)ccc2C1C(=O)Nc1ccc(C(CCF)(C(F)(F)F)C(F)(F)F)cc1]

Step 1: tert-Butyl N-[4-[3-hydroxy-1,1-bis(trifluoromethyl)propyl]phenyl]carbamate

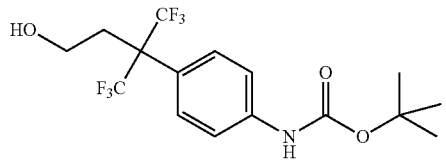 [SMILES: CC(C)(C)OC(=O)Nc1ccc(C(CCO)(C(F)(F)F)C(F)(F)F)cc1]

To a solution of LiAlH₄ (2.41 mL, 2.41 mmol) in THF, a solution of methyl 3-(4-((tert-butoxycarbonyl)amino)phenyl)-4,4,4-trifluoro-3-(trifluoromethyl)butanoate (product of step 3 of the synthesis of Intermediate 8, 0.5 g, 1.20 mmol) in THF (3 mL) was added dropwise. After the addition was completed, the reaction mixture was allowed to stir at rt for 2.5 h. The reaction mixture was cooled in an ice-water bath and methanol (1 mL) was carefully added dropwise, then ice-water bath was removed, the mixture was stirred at rt for 5 min and then partitioned between EtOAc (250 mL) and diluted aqueous HCl (35 mL). The layers were separated and the organic layer was washed with saturated aqueous NaHCO₃ solution (1×35 mL) and dried over Na₂SO₄. After filtration, the filtrate was concentrated in vacuo to give the crude product (360 mg, 77%), which was used without further purification.

LC/MS: m/z=386 [M–H]⁻. ¹H-NMR (500 MHz, DMSO-d₆); δ 1.48 (s, 9H); 2.50-2.54 (m, 2H); 3.36-3.40 (m, 2H); 4.87 (t, 1H); 7.48 (d, 2H); 7.57 (d, 2H); 9.58 (s, 1H).

Step 2: tert-Butyl N-[4-[3-fluoro-1,1-bis(trifluoromethyl)propyl]phenyl]carbamate

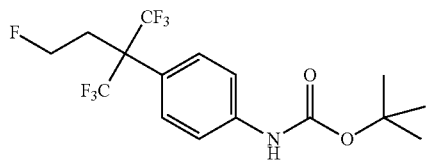 [SMILES: CC(C)(C)OC(=O)Nc1ccc(C(CCF)(C(F)(F)F)C(F)(F)F)cc1]

A solution of tert-butyl (4-(1,1,1-trifluoro-4-hydroxy-2-(trifluoromethyl)butan-2-yl)phenyl)carbamate (product of step 1 of the synthesis of Intermediate 9, 200 mg, 0.52 mmol) in DCM (4 mL) was cooled in an ice-water bath. To this a cold solution of DAST (0.273 mL, 2.07 mmol) in DCM was added. After addition was completed the ice-water bath was removed and the reaction mixture was stirred at rt over night. An additional portion of DAST (0.273 mL, 2.07 mmol) was added and the reaction mixture was stirred at rt for 3 h. Methanol (1 mL) was added and the reaction mixture was stirred at rt for 1 h. The mixture was partitioned between EtOAc (150 mL) and water (20 mL). The layers were separated in a phase separator. The organic layer was washed with saturated aqueous NaHCO₃ solution (1×25 mL), dried over Na₂SO₄, filtered and the filtrate was concentrated in vacuo to give the crude product (201 mg), which was used as such.

LC/MS: m/z=388 [M–H]⁻.

Step 3: 4-[3-Fluoro-1,1-bis(trifluoromethyl)propyl]aniline

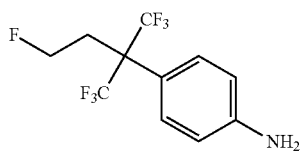 [SMILES: Nc1ccc(C(CCF)(C(F)(F)F)C(F)(F)F)cc1]

To a solution of tert-butyl (4-(1,1,1,4-tetrafluoro-2-(trifluoromethyl)butan-2-yl)phenyl)carbamate (product of step 2 of the synthesis of Intermediate 9, 201 mg, 0.52 mmol) in DCM (4 mL), TFA (1 mL, 12.98 mmol) was added and the resulting solution was stirred at room temperature for 45 min. The volatiles were removed in vacuo. The residue was dissolved in EtOAc (150 mL), washed with saturated aqueous NaHCO₃ solution (2×20 mL), dried over Na₂SO₄, filtered and the filtrate was concentrated in vacuo to give a crude product (140 mg), which was used without purification.

LC/MS: m/z=288 [M–H]⁻.

Step 4: tert-Butyl 1-[[4-[3-fluoro-1,1-bis(trifluoromethyl)propyl]phenyl]carbamoyl]-5-methylsulfonyl-isoindoline-2-carboxylate

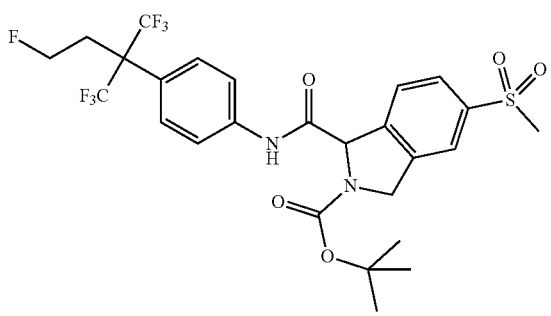 [SMILES: CC(C)(C)OC(=O)N1Cc2cc(S(C)(=O)=O)ccc2C1C(=O)Nc1ccc(C(CCF)(C(F)(F)F)C(F)(F)F)cc1]

To a mixture of 4-(1,1,1,4-tetrafluoro-2-(trifluoromethyl)butan-2-yl)aniline (product of step 3 of the synthesis of Intermediate 9,140 mg, 0.48 mmol) and 2-(tert-butoxycarbonyl)-5-(methylsulfonyl)isoindoline-1-carboxylic acid (product of step 1 of the synthesis of Intermediate 3, 165 mg, 0.48 mmol) in EtOAc (3 mL), T3P (50% in EtOAc) (0.576 mL, 0.97 mmol) was added in portions followed by Et$_3$N (0.202 mL, 1.45 mmol). After addition was completed the reaction mixture was stirred at rt for 40 min. The reaction mixture was partitioned between EtOAc (150 mL) and water (15 mL). The layers were separated in a phase separator. The organic layer was washed with water (2×20 mL), dried over Na$_2$SO$_4$, filtered and the filtrate was concentrated in vacuo to give a crude product (270 mg), which was used without further purification.

LC/MS: m/z=611 [M−H]$^−$.

Intermediate 10: tert-Butyl 1-[[4-[1-(cyanomethyl)-2,2,2-trifluoro-1-(trifluoromethyl)ethyl]phenyl]carbamoyl]-5-methylsulfonyl-isoindoline-2-carboxylate

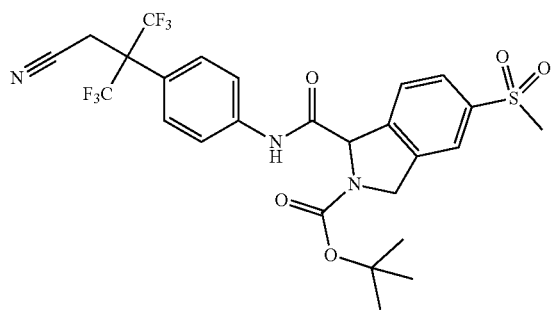 [SMILES: CC(C)(C)OC(=O)N1Cc2cc(S(C)(=O)=O)ccc2C1C(=O)Nc1ccc(C(CC#N)(C(F)(F)F)C(F)(F)F)cc1]

Step 1: Methyl 2-cyano-4,4,4-trifluoro-3-[4-(tert-butoxycarbonylamino)phenyl]-3-(trifluoromethyl)butanoate

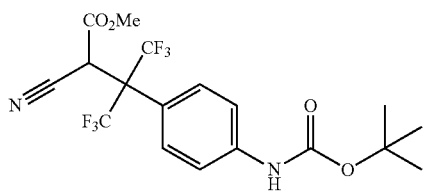 [SMILES: COC(=O)C(C#N)C(c1ccc(NC(=O)OC(C)(C)C)cc1)(C(F)(F)F)C(F)(F)F]

To a solution of tert-butyl (4-(1,1,1,3,3,3-hexafluoro-2-hydroxypropan-2-yl)phenyl)carbamate (product of step 1 of the synthesis of Intermediate 1, 150 mg, 0.42 mmol) in DCM (1 mL), Et$_3$N (0.116 mL, 0.84 mmol) was added followed by methanesulfonic anhydride (145 mg, 0.84 mmol) and the reaction mixture was stirred at rt for 45 min.

In a separate vial, to a suspension of potassium 2-methylpropan-2-olate (141 mg, 1.25 mmol) in DMF (1 mL), methyl 2-cyanoacetate (0.112 mL, 1.25 mmol) was added and the reaction mixture was stirred at rt for 40 min.

The reaction mixture of the first vial was added to the reaction mixture in the second vial in portions. After addition was completed the reaction mixture was stirred at rt for 40 min. The reaction mixture was partitioned between EtOAc (150 mL) and water (20 mL). The layers were separated in a phase separator. The organic layer was further washed with water (2×20 mL), dried over Na$_2$SO$_4$, filtered and the filtrate was concentrated in vacuo. The residue was purified by flash chromatography on silica (0-30% EtOAc in heptane). Fractions containing the desired product were collected and concentrated in vacuo to give the title compound (74 mg, 40%).

LC/MS: m/z=439 [M−H]$^−$. $^1$H NMR (600 MHz, DMSO-d$_6$) δ 1.48 (s, 9H); 3.72 (s, 3H); 6.20 (s, 1H); 7.54 (d, 2H); 7.59 (d, 2H); 9.67 (s, 1H).

Step 2: tert-Butyl N-[4-[1-(cyanomethyl)-2,2,2-trifluoro-1-(trifluoromethyl)ethyl]phenyl]carbamate

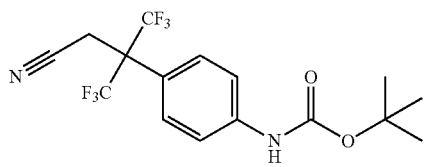 [SMILES: CC(C)(C)OC(=O)Nc1ccc(C(CC#N)(C(F)(F)F)C(F)(F)F)cc1]

To a solution of methyl 3-(4-((tert-butoxycarbonyl)amino)phenyl)-2-cyano-4,4,4-trifluoro-3-(trifluoromethyl)butanoate (product of step 1 of the synthesis of Intermediate 10, 65 mg, 0.15 mmol) in DMSO (1 mL), saturated aqueous NaCl solution (0.3 mL) was added and the reaction mixture was stirred at 125° C. for 3 h. The reaction mixture was cooled to rt, partitioned between EtOAc (150 mL) and water. The layers were separated in a phase separator. The organic layer was washed further with water (2×20 mL), dried over Na$_2$SO$_4$, filtered and the filtrate was concentrated in vacuo. The residue was purified by flash chromatography on silica (0-10% EtOAc in heptane). The fractions containing desired product were collected and concentrated in vacuo to give the title compound (25 mg, 44%).

LC/MS: m/z=381 [M−H]$^−$. $^1$H NMR (600 MHz, DMSO-d$_6$) δ 1.47 (s, 9H); 4.08 (s, 2H); 7.61 (s, 4H); 9.66 (s, 1H).

Step 3: 3-(4-Aminophenyl)-4,4,4-trifluoro-3-(trifluoromethyl)butanenitrile

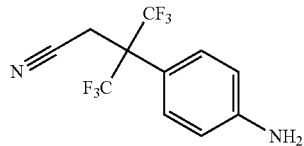 [SMILES: N#CCC(c1ccc(N)cc1)(C(F)(F)F)C(F)(F)F]

To a solution of tert-butyl (4-(2-(cyanomethyl)-1,1,1,3,3,3-hexafluoropropan-2-yl)phenyl)carbamate (product of step 2 of the synthesis of Intermediate 10, 23 mg, 0.06 mmol) in DCM (1 mL), TFA (0.3 mL, 3.89 mmol) was added and the resulting clear solution was stirred at rt for 45 min. The volatiles were removed in vacuo. The residue was dissolved in EtOAc (100 mL), washed with saturated aqueous NaHCO$_3$ solution (2×10 mL). The organic layer was dried over Na$_2$SO$_4$, filtered and the filtrate was concentrated in vacuo to give the crude product (15 mg, 88%). This material was used in the next step without further purification.

LC/MS: m/z=281 [M−H]$^−$.

Step 4: tert-Butyl 1-[[4-[1-(cyanomethyl)-2,2,2-trifluoro-1-(trifluoromethyl)ethyl]phenyl]carbamoyl]-5-methylsulfonyl-isoindoline-2-carboxylate

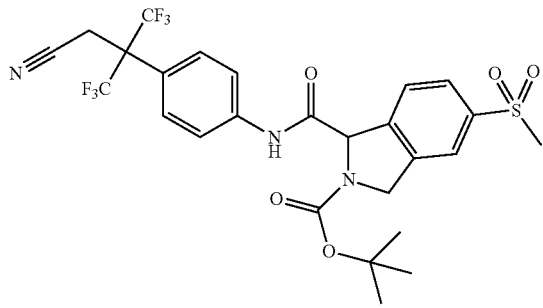 [SMILES: CC(C)(C)OC(=O)N1Cc2cc(S(C)(=O)=O)ccc2C1C(=O)Nc1ccc(C(CC#N)(C(F)(F)F)C(F)(F)F)cc1]

To a mixture of 3-(4-aminophenyl)-4,4,4-trifluoro-3-(trifluoromethyl)butanenitrile (15 mg, 0.05 mmol) and 2-(tert-butoxycarbonyl)-5-(methylsulfonyl)isoindoline-1-carboxylic acid (product of step 1 of the synthesis of Intermediate 3, 21.78 mg, 0.06 mmol) in EtOAc (1 mL), $Et_3N$ (0.022 mL, 0.16 mmol) was added followed by T3P (50% in EtOAc, 0.063 mL, 0.11 mmol) and the reaction mixture was stirred at rt for 1.5 h. The reaction mixture was diluted by addition of EtOAc (100 mL), washed with water (3×15 mL), dried over $Na_2SO_4$, filtered and the filtrate was concentrated in vacuo to give a crude product (32 mg, 99%). This material was used in the next step without further purification.
LC/MS: m/z=604 [M−H]⁻.

Intermediate 11: tert-Butyl 1-[[4-[3-ethoxy-3-oxo-1,1-bis(trifluoromethyl)propyl]phenyl]carbamoyl]-5-methylsulfonyl-isoindoline-2-carboxylate

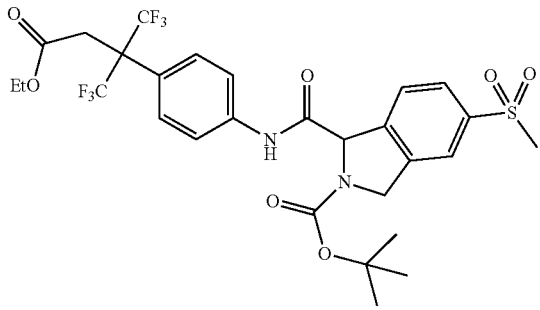 [SMILES: CCOC(=O)CC(c1ccc(NC(=O)C2c3ccc(S(C)(=O)=O)cc3CN2C(=O)OC(C)(C)C)cc1)(C(F)(F)F)C(F)(F)F]

Step 1: Ethyl 3-[4-(tert-butoxycarbonylamino)phenyl]-4,4,4-trifluoro-3-(trifluoromethyl)butanoate

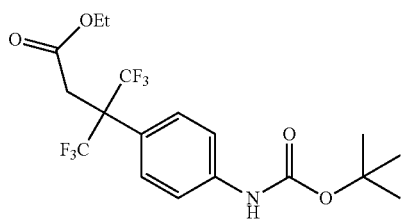 [SMILES: CCOC(=O)CC(c1ccc(NC(=O)OC(C)(C)C)cc1)(C(F)(F)F)C(F)(F)F]

To a solution of 3-(4-((tert-butoxycarbonyl)amino)phenyl)-4,4,4-trifluoro-3-(trifluoromethyl)butanoic acid (product of step 2 of the synthesis of Intermediate 8, 133 mg, 0.33 mmol) in DMF (3 mL), $Na_2CO_3$ (176 mg, 1.66 mmol) was added followed by iodoethane (0.107 mL, 1.33 mmol) and the reaction mixture was stirred at rt for 20 h. The reaction mixture was partitioned between EtOAc (150 mL) and water (25 mL). The layers were separated in a phase separator. The organic layer was washed further with water (2×20 mL), dried over $Na_2SO_4$, filtered and the filtrate was concentrated in vacuo to give a crude product (140 mg, 98%) which was used directly in the next step without further purification.
LC/MS: m/z=428 [M−H]⁻.

Step 2: Ethyl 3-(4-aminophenyl)-4,4,4-trifluoro-3-(trifluoromethyl)butanoate

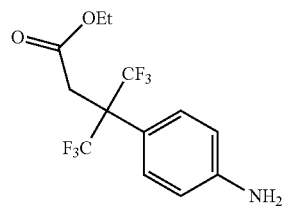 [SMILES: CCOC(=O)CC(c1ccc(N)cc1)(C(F)(F)F)C(F)(F)F]

To a solution of ethyl 3-(4-((tert-butoxycarbonyl)amino)phenyl)-4,4,4-trifluoro-3-(trifluoromethyl)butanoate (140 mg, 0.33 mmol) in DCM (2 mL), TFA (0.5 mL, 6.49 mmol) was added and the resulting solution was stirred at rt for 1 h. The volatiles were removed in vacuo. The residue was dissolved in EtOAc (150 mL), washed with saturated aqueous $NaHCO_3$ solution (2×10 mL), dried over $Na_2SO_4$, filtered and the filtrate was concentrated under reduced pressure to give the title compound as a crude product (102 mg, 95%). This material was used in the next step without further purification.

Step 3: tert-Butyl 1-[[4-[3-ethoxy-3-oxo-1,1-bis(trifluoromethyl)propyl]phenyl]carbamoyl]-5-methylsulfonyl-isoindoline-2-carboxylate

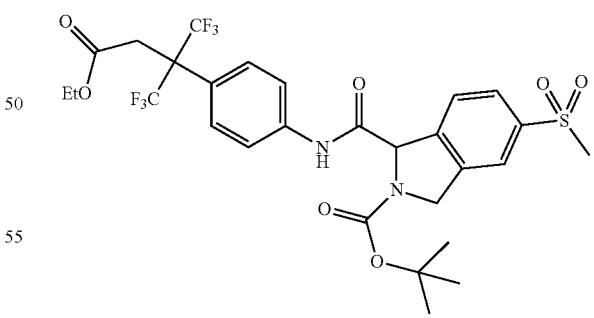

To a solution of ethyl 3-(4-aminophenyl)-4,4,4-trifluoro-3-(trifluoromethyl)butanoate (102 mg, 0.31 mmol) in EtOAc (2 mL), ethyl 3-(4-aminophenyl)-4,4,4-trifluoro-3-(trifluoromethyl)butanoate (102 mg, 0.31 mmol) was added. To this suspension $Et_3N$ (0.130 mL, 0.93 mmol) was added to result a clear solution. To this clear reaction mixture T3P (50% in EtOAc, 0.370 mL, 0.62 mmol) was added in portions. After addition was completed the reaction mixture was stirred at rt for 30 min. The reaction mixture was partitioned between EtOAc (150 mL) and water (20 mL). The layers were separated in a phase separator. The organic layer was washed further with water (3×20 mL), dried over Na₂SO₄, filtered and the filtrate was concentrated in vacuo to give a crude product (203 mg, 100%) which was used in the next step without further purification.

LC/MS: m/z=651 [M−H]⁻.

Intermediate 12: tert-Butyl 1-[[4-[3-(cyclopropylamino)-3-oxo-1,1-bis(trifluoromethyl)propyl]phenyl]carbamoyl]-5-methylsulfonyl-isoindoline-2-carboxylate

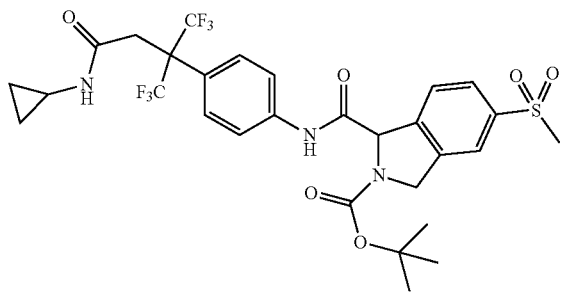 [SMILES: CC(C)(C)OC(=O)N1Cc2cc(S(C)(=O)=O)ccc2C1C(=O)Nc1ccc(C(CC(=O)NC2CC2)(C(F)(F)F)C(F)(F)F)cc1]

Step 1: tert-butyl N-[4-[3-(cyclopropylamino)-3-oxo-1,1-bis(trifluoromethyl)propyl]phenyl]carbamate

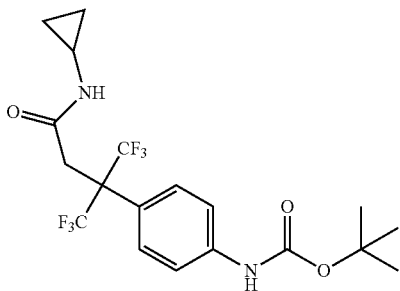 [SMILES: CC(C)(C)OC(=O)Nc1ccc(C(CC(=O)NC2CC2)(C(F)(F)F)C(F)(F)F)cc1]

To a solution of 3-(4-((tert-butoxycarbonyl)amino)phenyl)-4,4,4-trifluoro-3-(trifluoromethyl)butanoic acid (product of step 2 of the synthesis of Intermediate 8, 46 mg, 0.11 mmol) and cyclopropanamine (9.82 mg, 0.17 mmol) in EtOAc (1 mL), Et₃N (0.048 mL, 0.34 mmol) was added followed by T3P (50% in EtOAc) (0.136 mL, 0.23 mmol) and the reaction mixture was stirred at rt for 30 min. The reaction mixture was partitioned between EtOAc (100 mL) and water (10 mL). The layers were separated in a phase separator. The organic layer was washed further with water (1×10 mL). The organic layer was dried over Na₂SO₄, filtered and the filtrate was concentrated in vacuo to give a crude product (50 mg, 99%), which was used in the next step without further purification.

LC/MS: m/z=439 [M−H]⁻.

Step 2: 3-(4-Aminophenyl)-N-cyclopropyl-4,4,4-trifluoro-3-(trifluoromethyl)butanamide

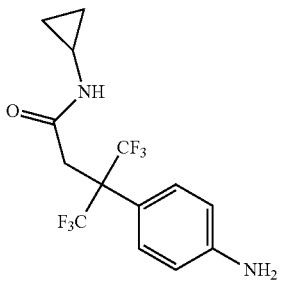 [SMILES: Nc1ccc(C(CC(=O)NC2CC2)(C(F)(F)F)C(F)(F)F)cc1]

To a solution of tert-butyl (4-(4-(cyclopropylamino)-1,1,1-trifluoro-4-oxo-2-(trifluoromethyl)butan-2-yl)phenyl)carbamate (product of step 1 of the synthesis of Intermediate 12, 50 mg, 0.11 mmol) in DCM (1 mL), TFA (0.3 mL, 3.89 mmol) was added and the resulting clear solution was allowed to stand at rt for 30 min. The volatiles were removed in vacuo. The residue was dissolved in EtOAc (100 mL), washed with saturated aqueous NaHCO₃ solution (2×10 mL). The organic layer was dried over Na₂SO₄, filtered and the filtrate was concentrated in vacuo to give a crude product (32 mg, 83%), which was used in the next step without further purification.

LC/MS: m/z=339 [M−H]⁻.

Step 3: tert-Butyl 1-[[4-[3-(cyclopropylamino)-3-oxo-1,1-bis(trifluoromethyl)propyl]phenyl]carbamoyl]-5-methylsulfonyl-isoindoline-2-carboxylate

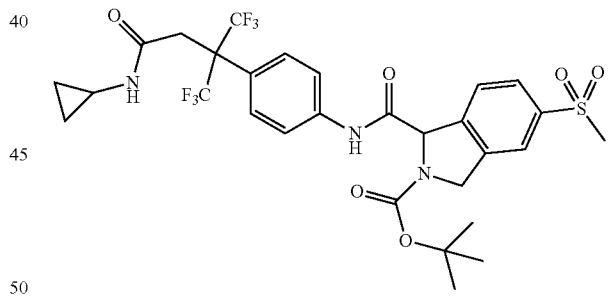

To a mixture of 3-(4-aminophenyl)-N-cyclopropyl-4,4,4-trifluoro-3-(trifluoromethyl)butanamide (32 mg, 0.09 mmol) and 2-(tert-butoxycarbonyl)-5-(methylsulfonyl)isoindoline-1-carboxylic acid (product of step 1 of the synthesis of Intermediate 3, 30 mg, 0.09 mmol) in EtOAc (1 mL), Et₃N (0.037 mL, 0.26 mmol) was added followed by T3P (50% in EtOAc, 0.105 mL, 0.18 mmol) and the reaction mixture was stirred at rt for 30 min. The reaction mixture was partitioned between EtOAc (100 mL) and water (10 mL). The layers were separated in a phase separator and the organic layer was washed further with water (1×10 mL), dried over Na₂SO₄, filtered and the filtrate was concentrated in vacuo to give a crude product (58 mg, 99%) which was used in the next step without further purification.

LC/MS: m/z=662 [M−H]⁻.

Intermediate 13: tert-Butyl 1-[[4-[3-acetamido-1,1-bis(trifluoromethyl)propyl]phenyl]carbamoyl]-5-methylsulfonyl-isoindoline-2-carboxylate

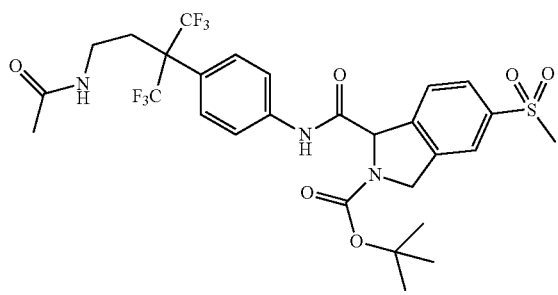 [SMILES: CC(=O)NCCC(c1ccc(NC(=O)C2c3ccc(S(C)(=O)=O)cc3CN2C(=O)OC(C)(C)C)cc1)(C(F)(F)F)C(F)(F)F]

Step 1: [3-[4-(tert-Butoxycarbonylamino)phenyl]-4,4,4-trifluoro-3-(trifluoromethyl)butyl] methanesulfonate

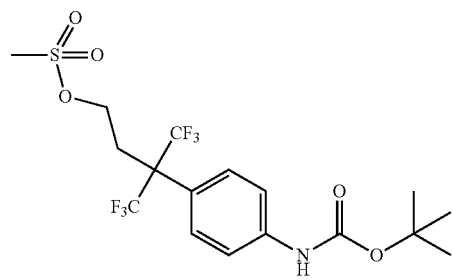 [SMILES: CC(C)(C)OC(=O)Nc1ccc(C(CCOS(C)(=O)=O)(C(F)(F)F)C(F)(F)F)cc1]

To a suspension of tert-butyl (4-(1,1,1-trifluoro-4-hydroxy-2-(trifluoromethyl)butan-2-yl)phenyl)carbamate (product of step 1 of the synthesis of Intermediate 9, 160 mg, 0.41 mmol) in DCM (3 mL) in an ice-water bath, Et$_3$N (0.173 mL, 1.24 mmol) was added followed by methanesulfonyl chloride (0.048 mL, 0.62 mmol). After addition was completed the reaction mixture was stirred at ca 3° C. for 45 min. To this reaction mixture methanol (0.2 mL) was added and the ice-water bath was removed. After 5 min at rt the reaction mixture was partitioned between EtOAc (150 mL) and water (15 mL). The layers were separated in a phase separator. The organic layer was washed with saturated aqueous NaHCO$_3$ solution (1×15 mL), dried over Na$_2$SO$_4$, filtered and the filtrate was concentrated in vacuo to give a crude product (192 mg, 100%) which was used in the next step without further purification.

LC/MS: m/z=464 [M−H]$^-$.

Step 2: tert-Butyl N-[4-[3-azido-1,1-bis(trifluoromethyl)propyl]phenyl]carbamate

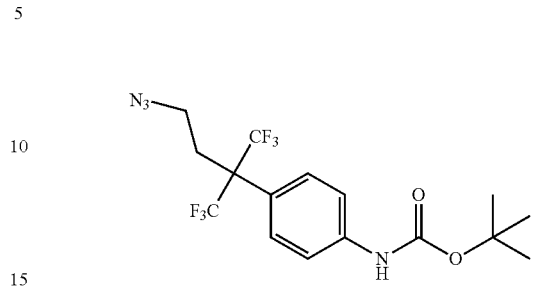

To a solution of 3-(4-((tert-butoxycarbonyl)amino)phenyl)-4,4,4-trifluoro-3-(trifluoromethyl)butyl methanesulfonate (product of step 1 of the synthesis of Intermediate 13, 192 mg, 0.41 mmol) in DMF (3 mL), sodium azide (0.073 mL, 2.06 mmol) was added and the reaction mixture was stirred at 65° C. After 2 h, an additional portion of sodium azide (0.073 mL, 2.06 mmol) was added and the reaction mixture was stirred at 65° C. for 36 h. The reaction mixture was cooled to rt, partitioned between EtOAc (150 mL) and water (20 mL). The layers were separated in a phase separator. The organic layer was washed further with water (3×15 mL), dried over Na$_2$SO$_4$, filtered and the filtrate was concentrated in vacuo to give a crude product (170 mg, 100%), which was used in the next step without further purification.

LC/MS: m/z=411 [M−H]$^-$.

Step 3: tert-Butyl N-[4-[3-amino-1,1-bis(trifluoromethyl)propyl]phenyl]carbamate

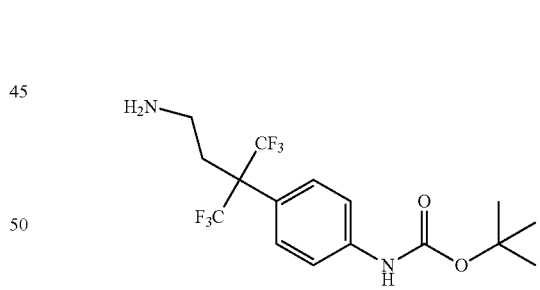

To a solution of tert-butyl (4-(4-azido-1,1,1-trifluoro-2-(trifluoromethyl)butan-2-yl)phenyl)carbamate (product of step 2 of the synthesis of Intermediate 13, 170 mg, 0.41 mmol) in THF (3 mL), water (0.375 mL) was added followed by triphenylphosphane (216 mg, 0.82 mmol) and the reaction mixture was stirred at 45° C. overnight. The volatiles were removed in vacuo and the residue was purified by flash chromatography on silica (0-50% EtOAc in heptane, then 5% methanol in DCM to remove all other products and finally 10% methanol in DCM). Fractions containing desired product were collected and concentrated in vacuo to give the title compound (62 mg, 39%).

LC/MS: m/z=385 [M−H]$^-$.

Step 4: tert-Butyl N-[4-[3-acetamido-1,1-bis(trifluoromethyl)propyl]phenyl]carbamate

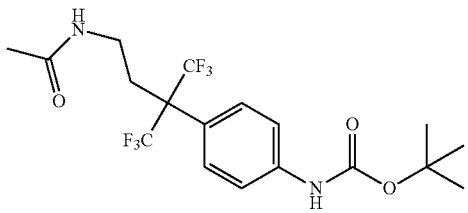 [SMILES: CC(=O)NCCC(c1ccc(NC(=O)OC(C)(C)C)cc1)(C(F)(F)F)C(F)(F)F]

To a solution of tert-butyl (4-(4-amino-1,1,1-trifluoro-2-(trifluoromethyl)butan-2-yl)phenyl)carbamate (product of step 3 of the synthesis of Intermediate 13, 60 mg, 0.16 mmol) in pyridine (1.5 mL), Ac$_2$O (0.073 mL, 0.78 mmol) was added and the reaction mixture was stirred at rt for 1 h. To this reaction mixture methanol (0.3 mL) was added and after 5 min the volatiles were removed in vacuo. The residue was dissolved in methanol (4 mL), concentrated in vacuo. This process was repeated for several times to give a crude product (67 mg, 100%), which was used in the next step without further purification.

LC/MS: m/z=427 [M−H]$^-$.

Step 5: N-[3-(4-Aminophenyl)-4,4,4-trifluoro-3-(trifluoromethyl)butyl]acetamide

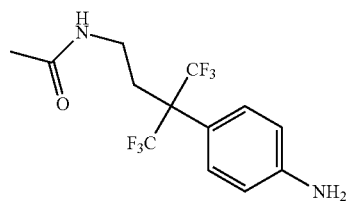 [SMILES: CC(=O)NCCC(c1ccc(N)cc1)(C(F)(F)F)C(F)(F)F]

To a solution of tert-butyl (4-(4-acetamido-1,1,1-trifluoro-2-(trifluoromethyl)butan-2-yl)phenyl)carbamate (product of step 4 of the synthesis of Intermediate 13, 67 mg, 0.16 mmol) in DCM (1.5 mL), TFA (0.5 mL, 6.49 mmol) was added and the resulting reaction mixture was stirred at rt for 45 min. The volatiles were removed in vacuo. The residue was dissolved in EtOAc (150 mL), washed with water (1×10 mL) and aqueous saturated NaHCO$_3$ solution (1×20 mL). The organic layer was dried over Na$_2$SO$_4$, filtered and the filtrate was concentrated in vacuo to give the title compound as a crude (50 mg, 97%) which was used in the next step without further purification.

LC/MS: m/z=327 [M−H]$^-$.

Step 6: tert-Butyl 1-[[4-[3-acetamido-1,1-bis(trifluoromethyl)propyl]phenyl]carbamoyl]-5-methylsulfonyl-isoindoline-2-carboxylate

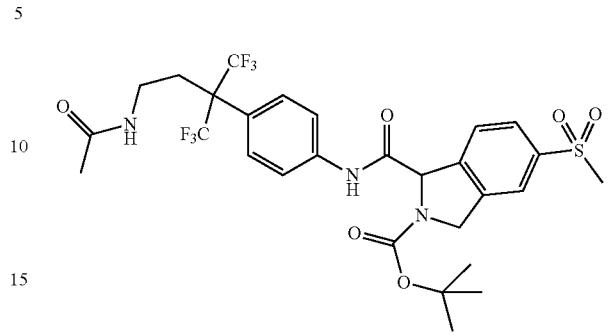

To a mixture of N-(3-(4-aminophenyl)-4,4,4-trifluoro-3-(trifluoromethyl)butyl)acetamide (50 mg, 0.15 mmol) and 2-(tert-butoxycarbonyl)-5-(methylsulfonyl)isoindoline-1-carboxylic acid (product of step 1 of the synthesis of Intermediate 3, 52.0 mg, 0.15 mmol) in EtOAc (1.2 mL), T3P (50% in EtOAc, 0.181 mL, 0.30 mmol) was added followed by Et$_3$N (0.064 mL, 0.46 mmol). After the addition was completed the reaction mixture was stirred at rt for 40 min. The reaction mixture was partitioned between EtOAc (150 mL) and water (15 mL). The layers were separated in a phase separator. The organic layer was further washed with water (2×15 mL), dried over Na$_2$SO$_4$, filtered and the filtrate was concentrated in vacuo to give the title compound as a crude (99 mg, 100%) which was used in the next step without further purification.

LC/MS: m/z=650 [M−H]$^-$.

Example 1: N-[4-(2-Cyano-1,1,1,3,3,3-hexafluoropropan-2-yl)phenyl]-5-(methylsulfonyl)-2,3-dihydro-1H-isoindole-1-carboxamide

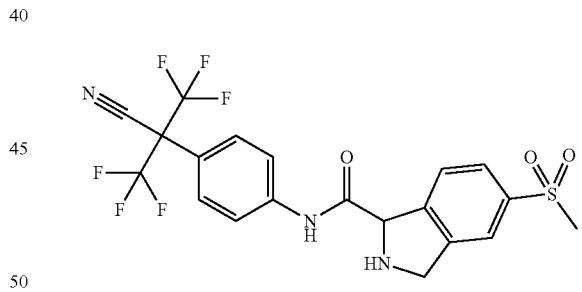

9H-Fluoren-9-ylmethyl 1-[[4-[1-cyano-2,2,2-trifluoro-1-(trifluoromethyl)ethyl]phenyl]carbamoyl]-5-methylsulfonyl-isoindoline-2-carboxylate (Intermediate 2, 315 mg, 0.44 mmol) was dissolved in ACN (10 mL) and to this diethylamine (3.69 mL, 35.31 mmol) was added. The reaction was stirred at rt for 1 h. The reaction was concentrated in vacuo and the residue was dissolved in methanol and loaded onto a 10 g Isolute™ SCX cartridge (previously flushed with methanol). The cartridge was washed with methanol and then the product was eluted with 2M NH$_3$ in methanol. The solvent was removed in vacuo to afford the product as a light green gum. This material was used crude in the next step. A small sample for biological screening was purified by trituration with methanol.

LC/MS: m/z=492 [M+H]$^+$. HRMS: calculated for (C$_{20}$H$_{15}$F$_6$N$_3$O$_3$S+H)$^+$ 492.0816; found (ESI [M+H]$^+$)

492.0830. $^1$H NMR (500 MHz, DMSO-d$_6$) δ 3.19 (s, 3H), 3.94 (br s, 1H), 4.31-4.46 (m, 2H), 5.11 (s, 1H), 7.68-7.74 (m, 3H), 7.82 (dd, 1H), 7.88 (s, 1H), 7.95-8.03 (m, 2H), 10.51 (s, 1H).

The hydrochloride salt of the title compound can be obtained from treatment of tert-butyl 1-[[4-[1-cyano-2,2,2-trifluoro-1-(trifluoromethyl)ethyl]phenyl]carbamoyl]-5-methylsulfonyl-isoindoline-2-carboxylate (Intermediate 4) with hydrochloric acid.

tert-Butyl 1-[[4-[1-cyano-2,2,2-trifluoro-1-(trifluoromethyl)ethyl]phenyl]carbamoyl]-5-methylsulfonyl-isoindoline-2-carboxylate (Intermediate 4, 1.66 g, 2.81 mmol) was dissolved in isopropyl acetate (5 mL) and to this 6M HCl in IPA (5.14 mL, 30.87 mmol) was added. The reaction was stirred at rt overnight. The reaction was concentrated in vacuo to afford the hydrochloride salt of the title compound (1.32 g, 89%) as a solid, which was used without further purification.

LC/MS: m/z=492 [M+H]$^+$. $^1$H NMR (500 MHz, DMSO-d$_6$) δ 3.24 (s, 3H), 4.73 (d, 1H), 4.80 (d, 1H), 5.88 (s, 1H), 7.81 (d, 2H), 7.91-8.02 (m, 4H), 8.07 (s, 1H), 11.85 (s, 1H).

Example 2: 2-Acetyl-N-[4-(2-cyano-1,1,1,3,3,3-hexafluoropropan-2-yl)phenyl]-5-

(methylsulfonyl)-2,3-dihydro-1H-isoindole-1-carboxamide

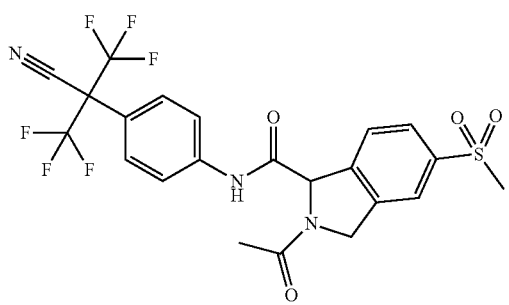 [SMILES: CC(=O)N1Cc2cc(S(C)(=O)=O)ccc2C1C(=O)Nc1ccc(C(C#N)(C(F)(F)F)C(F)(F)F)cc1]

N-[4-(2-Cyano-1,1,1,3,3,3-hexafluoropropan-2-yl)phenyl]-5-(methylsulfonyl)-2,3-dihydro-1H-isoindole-1-carboxamide (Example 1, 70 mg, 0.14 mmol) was dissolved in THF (6 mL) and to this acetic anhydride (0.094 mL, 1.00 mmol) was added. The reaction was stirred at rt for 1 h. The reaction was concentrated in vacuo and the crude purified by RP-HPLC (chromatographic conditions: gradient 5-95% ACN in 0.1M HCO$_2$H, pH3; column: Waters Sunfire C18 ODB 5μ 19×150 mm) to give the title compound (54 mg, 70.9%). HRMS: calculated for (C$_{22}$H$_{17}$F$_6$N$_3$O$_4$S+H)$^+$ 534.0922; found (ESI [M+H]$^+$) 534.0921. $^1$H NMR (600 MHz, DMSO-d$_6$, mixture of rotamers, 5*:1) δ 1.99, 2.15* (s, 3H), 3.21, 3.22* (s, 3H), 4.76-4.93, 4.99-5.1* (m, 2H), 5.73*, 5.95 (s, 1H), 7.70 (d, 1H), 7.73-7.79 (m, 2H), 7.86-7.93 (m, 3H), 8.00*, 8.03 (s, 1H), 10.92*, 11.14 (s, 1H).

Example 3: N-[4-(2-Cyano-1,1,1,3,3,3-hexafluoropropan-2-yl)phenyl]-2-[(1- methoxycyclopropyl)carbonyl]-5-(methylsulfonyl)-2,3-dihydro-1H-isoindole-1-carboxamide

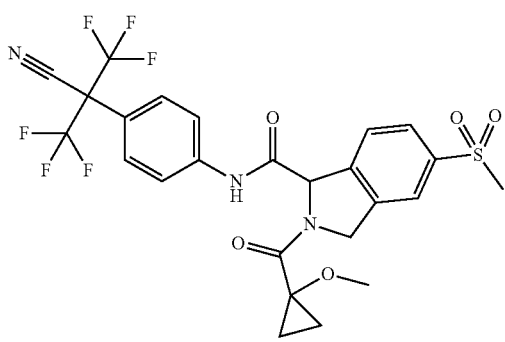 [SMILES: COC1(C(=O)N2Cc3cc(S(C)(=O)=O)ccc3C2C(=O)Nc2ccc(C(C#N)(C(F)(F)F)C(F)(F)F)cc2)CC1]

T3P (50% solution in EtOAc, 0.145 mL, 0.24 mmol) was added to a solution of N-[4-(2-cyano-1,1,1,3,3,3-hexafluoropropan-2-yl)phenyl]-5-(methylsulfonyl)-2,3-dihydro-1H-isoindole-1-carboxamide (Example 1, 60 mg, 0.12 mmol). 1-methoxycyclopropanecarboxylic acid (21.27 mg, 0.18 mmol) and triethylamine (0.034 mL, 0.24 mmol) in DCM (2 mL). The resulting mixture was stirred at rt for 1 h. The reaction mixture was partitioned between DCM and a saturated aqueous solution of sodium bicarbonate. The layers were separated using a phase separator cartridge and the organic layer was concentrated in vacuo. The residue was purified by RP-HPLC (chromatographic conditions: gradient 5-95% ACN in 0.1M HCO$_2$H, pH3; column: Waters Sunfire C18 ODB 5μ 30×150 mm) to afford the title compound (43.6 mg, 60.6%).

HRMS: calculated for (C$_{25}$H$_{21}$F$_6$N$_3$O$_5$S+H)$^+$ 590.1184; found (ESI [M+H]$^+$) 590.1211. $^1$H NMR (600 MHz, DMSO-d$_6$, mixture of rotamers, 2*:1) δ 0.81-1.2 (m, 4H), 3.18, 3.22* (s, 3H), 3.35 (s, 3H), 4.86-5.04, 5.18-5.29* (m, 2H), 5.90*, 6.22 (s, 1H), 7.72-7.83 (m, 3H), 7.87-7.93 (m, 3H), 8.03, 8.06* (s, 1H), 11.01, 11.09* (s, 1H).

Example 4: N$^1$-[4-(2-Cyano-1,1,1,3,3,3-hexafluoropropan-2-yl)phenyl]-N$^2$-methyl-5-

(methylsulfonyl)-1,3-dihydro-2H-isoindole-1,2-dicarboxamide

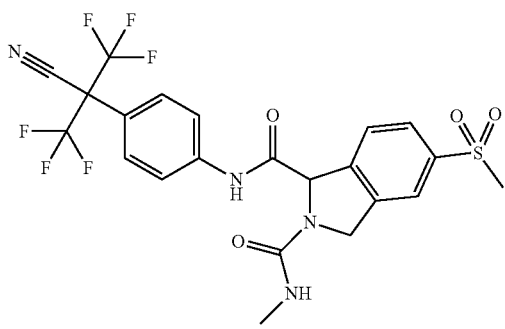 [SMILES: CNC(=O)N1Cc2cc(S(C)(=O)=O)ccc2C1C(=O)Nc1ccc(C(C#N)(C(F)(F)F)C(F)(F)F)cc1]

Methyl isocyanate (43.2 mg, 0.76 mmol) was added to a mixture of the HCl salt of N-[4-(2-cyano-1,1,1,3,3,3- hexafluoropropan-2-yl)phenyl]-5-(methylsulfonyl)-2,3-dihydro-1H-isoindole-1-carboxamide (Example 1, 200 mg, 0.38 mmol) and triethylamine (0.158 mL, 1.14 mmol) in a mixture of DCM (2 mL) and THF (2 mL). The reaction mixture was stirred at rt for 15 min. The mixture was concentrated in vacuo and the residue dissolved in EtOAc and washed with 1M aq HCl. The layers were separated and the organic layer was dried using a phase separator cartridge. The solvent was removed in vacuo and the residue was purified by preparative SFC (chromatographic conditions: MeOH/NH$_3$ 20 mM; column: Phenomenex Luna Hilic 5μ 30×250 mm) to afford the title compound (127 mg, 61%).

HRMS: calculated for $(C_{22}H_{18}F_6N_4O_4S+H)^+$ 549.1031; found (ESI [M+H]$^+$) 549.1030. 1H NMR (600 MHz, DMSO-d$_6$) δ 2.64 (d, 3H), 3.22 (s, 3H), 4.75 (d, 1H), 4.82 (dd, 1H), 5.66 (d, 1H), 6.62 (q, 1H), 7.67 (d, 1H), 7.73 (d, 2H), 7.85-7.92 (m, 3H), 7.97 (s, 1H), 10.82 (s, 1H).

Examples 5-11

Examples 5-11 (Table 1) were prepared using similar procedures to those described in examples 2 to 4.

Example 5: N-[4-(2-Cyano-1,1,1,3,3,3-hexafluoropropan-2-yl)phenyl]-2-(hydroxyacetyl)-5-(methylsulfonyl)-2,3-dihydro-1H-isoindole-1-carboxamide Example 6: N-[4-(2-Cyano-1,1,1,3,3,3-hexafluoropropan-2-yl)phenyl]-2-formyl-5-(methylsulfonyl)-2,3-dihydro-1H-isoindole-1-carboxamide Example 7: Methyl 1-{[4-(2-cyano-1,1,1,3,3,3-hexafluoropropan-2-yl)phenyl]carbamoyl}-5-(methylsulfonyl)-1,3-dihydro-2H-isoindole-2-carboxylate Example 8: N-[4-(2-Cyano-1,1,1,3,3,3-hexafluoropropan-2-yl)phenyl]-2-(methoxyacetyl)-5-(methylsulfonyl)-2,3-dihydro-1H-isoindole-1-carboxamide Example 9: 4-[1-{[4-(2-Cyano-1,1,1,3,3,3-hexafluoropropan-2-yl)phenyl]carbamoyl}-5-(methylsulfonyl)-1,3-dihydro-2H-isoindol-2-yl]-4-oxobutanoic acid Example 10: N-[4-(2-Cyano-1,1,1,3,3,3-hexafluoropropan-2-yl)phenyl]-2-glycyl-5-(methylsulfonyl)-2,3-dihydro-1H-isoindole-1-carboxamide Example 11: 2-(3-Aminopropanoyl)-N-[4-[1-cyano-2,2,2-trifluoro-1-(trifluoromethyl)ethyl]phenyl]-5-methylsulfonyl-isoindoline-1-carboxamide

TABLE 1

| Example No. | Structure | MS + NMR |
|---|---|---|
| 5 | 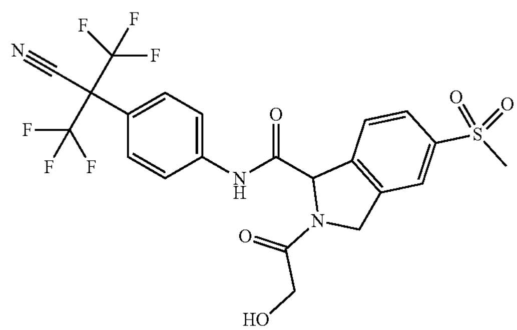 [SMILES: CS(=O)(=O)c1ccc2c(c1)CN(C(=O)CO)C2C(=O)Nc1ccc(C(C#N)(C(F)(F)F)C(F)(F)F)cc1] | HRMS: calculated for (C$_{22}$H$_{17}$F$_6$N$_3$O$_5$S + H)$^+$ 550.0871; found (ESI [M + H]$^+$) 550.0863. $^1$H NMR (600 MHz, DMSO-d$_6$, mixture of rotamers, 4*:1) δ 3.21, 3.22* (s, 3H), 3.92, 4.15, 4.24* (dd, 1H), 4.27* (dd, 1H), 4.83-4.96, 4.96-4.99* (m, 2H), 5.00*, 5.24 (t, 1H), 5.79*, 6.03 (s, 1H), 7.71-7.8 (m, 3H), 7.87 - 7.92 (m, 3H), 8.00*, 8.04 (s, 1H), 10.96*, 11.10 (s, 1H). |
| 6 | 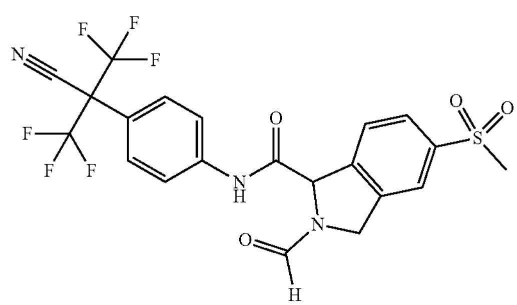 [SMILES: CS(=O)(=O)c1ccc2c(c1)CN(C=O)C2C(=O)Nc1ccc(C(C#N)(C(F)(F)F)C(F)(F)F)cc1] | HRMS: calculated for (C$_{21}$H$_{15}$F$_6$N$_3$O$_4$S + H)$^+$ 520.0765; found (ESI [M + H]$^+$) 520.0715. $^1$H NMR (600 MHz, DMSO-d$_6$, mixture of rotamers, 2*:1) δ 3.22, 3.23* (s, 3H), 4.78, 4.88, 5.08* (d, 1H), 5.14* (d, 1H), 5.78*, 6.01 (s, 1H), 7.71-7.78 (m, 3H), 7.83-7.94 (m, 3H), 8.04, 8.05* (s, 1H), 8.40, 8.49* (s, 1H), 10.97*, 11.06 (s, 1H). |
| 7 | 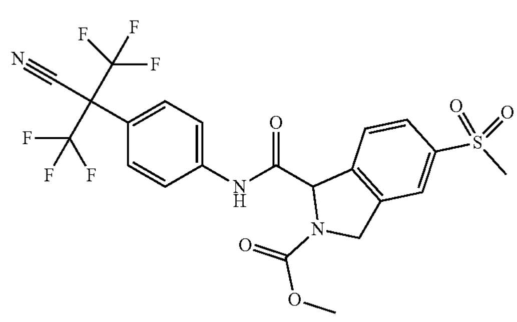 [SMILES: COC(=O)N1Cc2cc(S(C)(=O)=O)ccc2C1C(=O)Nc1ccc(C(C#N)(C(F)(F)F)C(F)(F)F)cc1] | HRMS: calculated for (C$_{22}$H$_{17}$F$_6$N$_3$O$_5$S + H)$^+$ 550.0871; found (ESI [M + H]$^+$) 550.0847. $^1$H NMR (600 MHz, DMSO-d$_6$, mixture of rotamers, 4*:3) δ 3.21 (s, 3H), 3.63, 3.71* (s, 3H), 4.81-4.92 (d, 2H), 5.69*, 5.71 (s, 1H), 7.71, 7.76 (d, 3H), 7.87-7.93 (m, 3H), 8.01*, 8.03 (s, 1H), 10.96, 10.99* (s, 1H). |

TABLE 1-continued

| Example No. | Structure | MS + NMR |
|---|---|---|
| 8 | 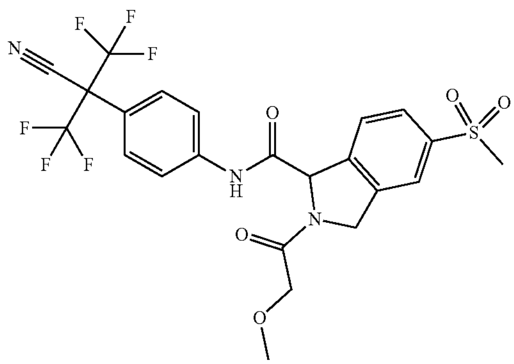 [SMILES: COCC(=O)N1Cc2cc(S(C)(=O)=O)ccc2C1C(=O)Nc1ccc(C(C#N)(C(F)(F)F)C(F)(F)F)cc1] | HRMS: calculated for (C₂₃H₁₉F₆N₃O₅S + H)⁺ 564.1028; found (ESI [M + H]⁺) 564.1011. ¹H NMR (600 MHz, DMSO-d₆, mixture of rotamers, 4*:1) δ 3.21, 3.22* (s, 3H), 3.26, 3.36* (s, 3H), 3.96-4.11, 4.19-4.31* (m, 2H), 4.82-5.07 (m, 2H), 5.80*, 6.01 (s, 1H), 7.69-7.81 (m, 3H), 7.85-7.94 (m, 3H), 8.01*, 8.04 (s, 1H), 10.98*, 11.05 (s, 1H). |
| 9 | 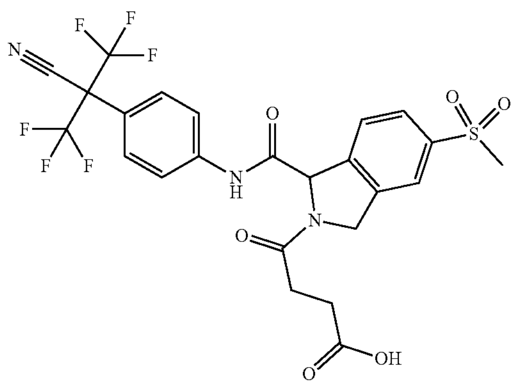 [SMILES: CS(=O)(=O)c1ccc2c(c1)CN(C(=O)CCC(=O)O)C2C(=O)Nc1ccc(C(C#N)(C(F)(F)F)C(F)(F)F)cc1] | HRMS: calculated for (C₂₄H₁₉F₆N₃O₆S + H)⁺ 592.0977; found (ESI [M + H]⁺) 592.0972. ¹H NMR (600 MHz, DMSO-d₆, mixture of rotamers, 5*:1) δ 2.44-2.7 (m, 2H), 2.63-2.7 (m, 1H), 2.72-2.79 (m, 1H), 3.22, 3.23* (s, 3H), 4.72-4.95, 5.02-5.13*(m, 2H), 5.74*, 6.01 (s, 1H), 7.68-7.8 (m, 3H), 7.86-7.94 (m, 3H), 8.02*, 8.04 (s, 1H), 10.88*, 11.13 (s, 1H), 12.13 (br s, 1H). |
| 10 | 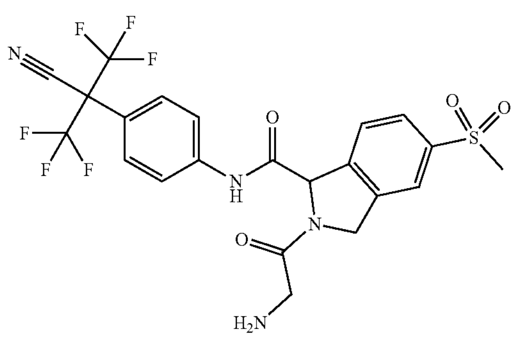 [SMILES: CS(=O)(=O)c1ccc2c(c1)CN(C(=O)CN)C2C(=O)Nc1ccc(C(C#N)(C(F)(F)F)C(F)(F)F)cc1] | HRMS: calculated for (C₂₂H₁₈F₆N₄O₄S + H)⁺ 549.1031; found (ESI [M + H]⁺) 549.1021. ¹H NMR (600 MHz, DMSO-d₆, mixture of rotamers, 5*:1) δ 3.21, 3.22* (s, 3H), 3.47-3.57 (m, 2H), 4.80-4.96, 4.94-5.02* (m, 2H), 5.79*, 5.97 (s, 1H), 7.69-7.81 (m, 3H), 7.87-7.94 (m, 3H), 8.01*, 8.05 (s, 1H), 10.98 (s, 1H). |
| 11 | 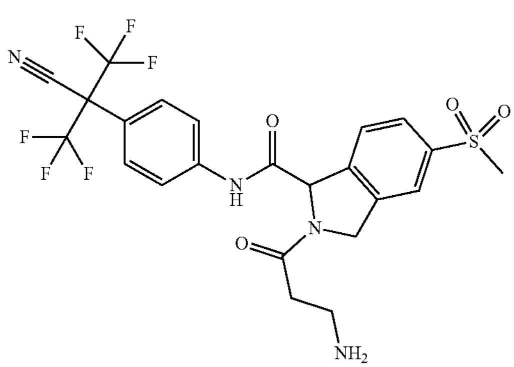 [SMILES: CS(=O)(=O)c1ccc2c(c1)CN(C(=O)CCN)C2C(=O)Nc1ccc(C(C#N)(C(F)(F)F)C(F)(F)F)cc1] | HRMS: calculated for (C₂₃H₂₀F₆N₄O₄S + H)⁺ 563.1188; found (ESI [M + H]⁺) 563.1213. ¹H NMR (600 MHz, DMSO-d₆, mixture of rotamers, 4*:1) δ 2.56-2.61 (m, 2H), 2.83, 2.85* (t, 2H), 3.21, 3.23* (s, 3H), 4.77-4.96, 5.02-5.1* (m, 2H), 5.77*, 6.06 (s, 1H), 7.70-7.81 (m, 3H), 7.88-7.95 (m, 3H), 8.01*, 8.03 (s, 1H). |

Example 12: N-[4-(2-Cyano-1,1,1,3,3,3-hexafluoropropan-2-yl)phenyl]-5-[(cyclopropylmethyl)sulfonyl]-2,3-dihydro-1H-isoindole-1-carboxamide

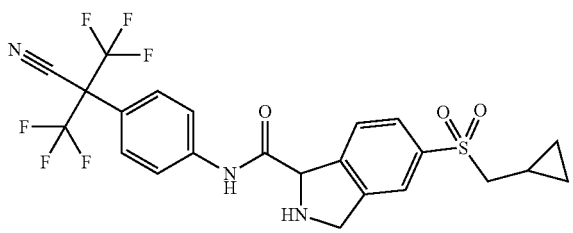 [SMILES: N#CC(c1ccc(NC(=O)C2NCc3cc(S(=O)(=O)CC4CC4)ccc32)cc1)(C(F)(F)F)C(F)(F)F]

9H-Fluoren-9-ylmethyl 1-[[4-[1-cyano-2,2,2-trifluoro-1-(trifluoromethyl)ethyl]phenyl]carbamoyl]-5-(cyclopropylmethylsulfonyl)isoindoline-2-carboxylate (Intermediate 5, 310 mg, 0.41 mmol) was dissolved in ACN (10 mL) and to this diethylamine (3.44 mL, 32.90 mmol) was added. The reaction was stirred at rt for 1 h. The reaction was concentrated in vacuo and the residue was dissolved in methanol and loaded onto a 10 g Isolute™ SCX cartridge (previously flushed with methanol). The cartridge was washed with methanol and then the product was eluted with 2M NH$_3$ in methanol. The solvent was removed in vacuo to afford the title compound as a gum (230 mg, 105%), which was used without further purification. A small sample was purified for biological screening by RP-HPLC (chromatographic conditions: gradient 5-95% ACN in 0.2% NH$_3$, pH10; column: Waters Xbridge C18 5μ ODB 19×150 mm). LC/MS: m/z=532 [M+H]$^+$.

HRMS: calculated for (C$_{23}$H$_{19}$F$_6$N$_3$O$_3$S+H)$^+$ 532.1129; found (ESI [M+H]$^+$) 532.1119. $^1$H NMR (600 MHz, DMSO-d$_6$) δ 0.09-0.15 (m, 2H), 0.40-0.47 (m, 2H), 0.76-0.84 (m, 1H), 3.24 (dd, 2H), 4.05 (br s, 1H), 4.34-4.46 (m, 2H), 5.13 (s, 1H), 7.71 (dd, 3H), 7.79 (d, 1H), 7.85 (s, 1H), 7.97-8.01 (m, 2H), 10.53 (s, 1H).

Example 13: 2-Acetyl-N-[4-(2-cyano-1,1,1,3,3,3-hexafluoropropan-2-yl)phenyl]-5-[(cyclopropylmethyl)sulfonyl]-2,3-dihydro-1H-isoindole-1-carboxamide

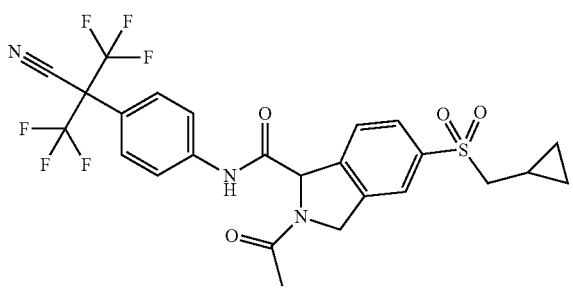 [SMILES: CC(=O)N1Cc2cc(S(=O)(=O)CC3CC3)ccc2C1C(=O)Nc1ccc(C(C#N)(C(F)(F)F)C(F)(F)F)cc1]

N-[4-(2-Cyano-1,1,1,3,3,3-hexafluoropropan-2-yl)phenyl]-5-[(cyclopropylmethyl)sulfonyl]-2,3-dihydro-1H-isoindole-1-carboxamide (Example 12, 80 mg, 0.15 mmol) was dissolved in THF (6 mL) and to this acetic anhydride (0.014 mL, 0.15 mmol) was added. The reaction was stirred at rt for 1 h, and then concentrated in vacuo. The residue was purified by RP-HPLC (chromatographic conditions: gradient 5-95% ACN in 0.1M HCO$_2$H, pH3; column: Waters Sunfire C18 ODB 5μ 19×150 mm) to afford the title compound (62.4 mg, 72.3%).

LC/MS: m/z=574 [M+H]$^+$. HRMS: calculated for (C$_{25}$H$_{21}$F$_6$N$_3$O$_4$S+H)$^+$ 574.1235; found (ESI [M+H]$^+$) 574.1229. $^1$H NMR (600 MHz, DMSO-d$_6$, Mixture of rotamers, 5*:1) δ 0.06-0.16 (m, 2H), 0.38-0.5 (m, 2H), 0.73-0.88 (m, 1H), 1.99, 2.15* (s, 3H), 3.22-3.31 (m, 2H), 4.74-4.92, 5-5.11* (m, 2H), 5.74*, 5.95 (d, 1H), 7.70 (d, 1H), 7.73-7.79 (m, 2H), 7.85-7.94 (m, 3H), 7.97*, 8.00 (s, 1H), 10.91*, 11.13 (s, 1H).

Example 14: 2-Acetyl-N-[4-(2-cyano-1,1,1,3,3,3-hexafluoropropan-2-yl)phenyl]-5-(ethylsulfonyl)-2,3-dihydro-1H-isoindole-1-carboxamide

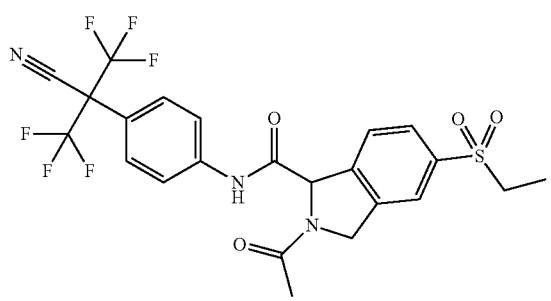 [SMILES: CCS(=O)(=O)c1ccc2c(c1)CN(C(C)=O)C2C(=O)Nc1ccc(C(C#N)(C(F)(F)F)C(F)(F)F)cc1]

Step 1: N-[4-[1-cyano-2,2,2-trifluoro-1-(trifluoromethyl)ethyl]phenyl]-5-ethylsulfonyl-isoindoline-1-carboxamide

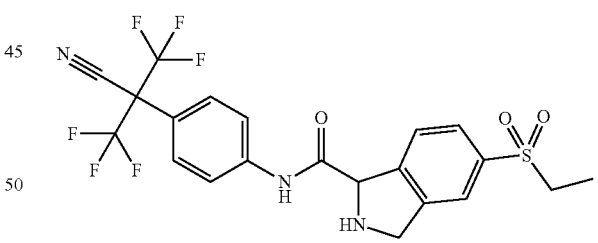

tert-Butyl 1-((4-(2-cyano-1,1,1,3,3,3-hexafluoropropan-2-yl)phenyl)carbamoyl)-5-(ethylsulfonyl)isoindoline-2-carboxylate (Intermediate 6, 60 mg, 0.10 mmol) was dissolved in DCM (2 mL) and to this TFA (1 mL, 12.98 mmol) was added. The reaction mixture was stirred at rt for 1 h. The reaction mixture was concentrated in vacuo and the residue dissolved in methanol. This was loaded onto a 1 g Isolute™ SCX cartridge (previously flushed with methanol). The cartridge was flushed with methanol before the product was eluted using 2M NH$_3$ in methanol. N-[4-[1-cyano-2,2,2-trifluoro-1-(trifluoromethyl)ethyl]phenyl]-5-ethylsulfonyl-isoindoline-1-carboxamide (35.0 mg, 70%) was obtained as a gum which was used directly in the next step.

LC/MS: m/z=506 [M+H]+.

Step 2: 2-Acetyl-N-[4-(2-cyano-1,1,1,3,3,3-hexafluoropropan-2-yl)phenyl]-5-

(ethylsulfonyl)-2,3-dihydro-1H-isoindole-1-carboxamide

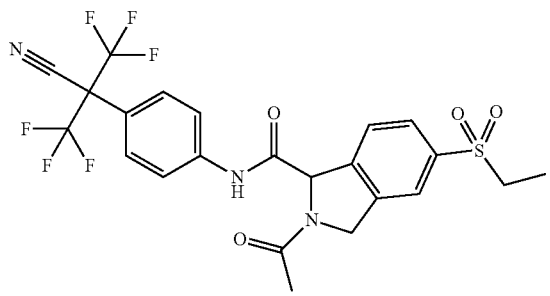 [SMILES: CCS(=O)(=O)c1ccc2c(c1)CN(C(C)=O)C2C(=O)Nc1ccc(C(C#N)(C(F)(F)F)C(F)(F)F)cc1]

N-[4-[1-cyano-2,2,2-trifluoro-1-(trifluoromethyl)ethyl]phenyl]-5-ethylsulfonyl-isoinindoline-1-carboxamide (35 mg, 0.07 mmol) was dissolved in DCM (2 mL) and to this triethylamine (0.019 mL, 0.14 mmol) and then acetyl chloride (9.85 µl, 0.14 mmol) was added. The mixture was stirred at rt for 30 min. The reaction was concentrated in vacuo. The residue was purified by RP-HPLC (chromatographic conditions: gradient 5-95% ACN in 0.1M HCO$_2$H, pH3; column: Waters Sunfire C18 ODB 5µ 19×150 mm) to afford the title compound (21.10 mg, 56%). LC/MS: m/z=548 [M+H]+.

HRMS: calculated for (C$_{23}$H$_{19}$F$_6$N$_3$O$_4$S+H)+ 548.1078; found (ESI [M+H]+) 548.1075. $^1$H NMR (600 MHz, DMSO-d$_6$, mixture of rotamers, 5*:1) δ 1.09, 1.1* (t, 3H), 1.99, 2.15* (s, 3H), 3.25-3.32 (m, 2H), 4.72-4.92, 5-5.11* (m, 2H), 5.73*, 5.95 (s, 1H), 7.69-7.79 (m, 3H), 7.85-7.93 (m, 3H), 7.96*, 7.99 (s, 1H), 10.93*, 11.15 (s, 1H).

Example 15: 2-Acetyl-N-{4-[1,1,1,3,3,3-hexafluoro-2-(pyrrolidin-1-yl)propan-2- yl]phenyl}-5-(methylsulfonyl)-2,3-dihydro-1H-isoindole-1-carboxamide

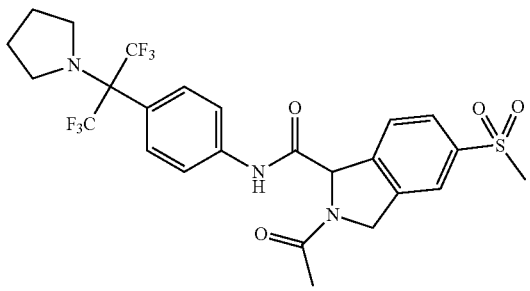 [SMILES: CC(=O)N1Cc2cc(S(C)(=O)=O)ccc2C1C(=O)Nc1ccc(C(N2CCCC2)(C(F)(F)F)C(F)(F)F)cc1]

2-Acetyl-N-(4-(1,1,1,3,3,3-hexafluoro-2-hydroxypropan-2-yl)phenyl)-5-(methylsulfonyl)isoindoline-1-carboxamide (Intermediate 3, 73.4 mg, 0.14 mmol) was suspended in ACN (2 mL). Triethylamine (0.058 mL, 0.42 mmol) was added and a solution obtained. A solution of methanesulfonic anhydride (73.2 mg, 0.42 mmol) in ACN (2 mL) was added and the resulting mixture was stirred at rt for 0.5 h. Pyrrolidine (49.8 mg, 0.70 mmol) dissolved in ACN (1 mL) was then added and the resulting mixture was stirred at 50° C. for 1 h. The mixture was concentrated in vacuo. The residue was partitioned between EtOAc and 0.5M aqueous HCl. The layers were separated and the organic layer was dried using a phase separator cartridge and concentrated in vacuo. The crude was purified by preparative SFC-MS (chromatographic conditions: MeOH/NH$_3$ 20 mM; column: Waters BEH 5 µm 30×250 mm) to give the title compound (23.9 mg, 29.6%). HRMS: calculated for (C$_{25}$H$_{25}$F$_6$N$_3$O$_4$S+H)+ 578.1548; found (ESI [M+H]+) 578.1555. $^1$H NMR (600 MHz, DMSO-d$_6$, mixture of rotamers, 4*:1) δ 1.72-1.81 (m, 4H), 1.99, 2.15* (s, 3H), 2.86 (br s, 4H), 3.21, 3.22* (s, 3H), 4.74-4.92, 4.99-5.09* (m, 2H), 5.72*, 5.92 (s, 1H), 7.55*, 7.57 (d, 2H), 7.67-7.79 (m, 3H), 7.90 (dd, 1H), 7.99*, 8.02 (s, 1H), 10.70*, 10.94 (s, 1H).

Example 16: 2-Acetyl-N-{4-[1,1,1,3,3,3-hexafluoro-2-(propylamino)propan-2-yl]phenyl}-

5-(methylsulfonyl)-2,3-dihydro-1H-isoindole-1-carboxamide

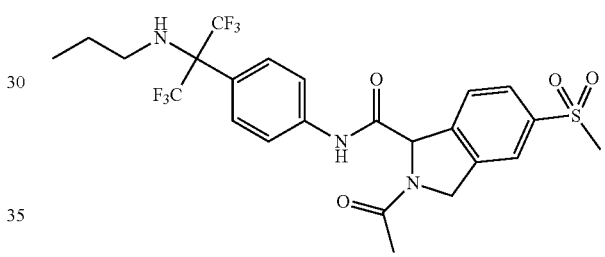

2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide (Intermediate 3, 0.080 g, 0.15 mmol) was suspended in ACN (2 ml). Triethylamine (0.063 ml, 0.46 mmol) was added and a solution obtained. A solution of methanesulfonic anhydride (0.080 g, 0.46 mmol) in ACN (2 ml) was added and the resulting mixture was stirred at rt for 0.5 h. Propan-1-amine (0.045 g, 0.76 mmol) in ACN (1 ml) was then added and the resulting mixture was stirred at 50° C. for 0.5 h. The mixture was concentrated in vacuo and the residue partitioned between EtOAc and 0.5M aqueous HCl. The layers were separated and the organic layer was dried using a phase separator cartridge and concentrated in vacuo. The crude was purified by preparative SFC-MS (chromatographic conditions: MeOH/NH$_3$ 20 mM; column: Phenomenex Luna Hilic 5µ 30×250 mm) to give the title compound (44 mg, 50.4%). HRMS: calculated for (C$_{24}$H$_{25}$F$_6$N$_3$O$_4$S+H)+ 566.1548; found (ESI [M+H]+) 566.1531. $^1$H NMR (600 MHz, DMSO-d$_6$, mixture of rotamers, 4*:1) δ 0.83 (t, 3H), 1.43-1.59 (m, 2H), 1.99, 2.15* (s, 3H), 2.30-2.37 (m, 2H), 3.21, 3.22* (s, 3H), 3.59-3.69 (m, 1H), 4.73-4.94, 4.99-5.08* (m, 2H), 5.73*, 5.93 (s, 1H), 7.60*, 7.62 (d, 2H), 7.68-7.79 (m, 3H), 7.90 (d, 1H), 8.00*, 8.03 (s, 1H), 10.69*, 10.92 (s, 1H).

Examples 17-27

Examples 17-27 (Table 2) were prepared using similar procedures to those described in examples 15 and 16.

Example 17: 2-Acetyl-N-(4-{1,1,1,3,3,3-hexafluoro-2-[(2-methoxyethyl)amino]propan-2-yl}phenyl)-5-(methylsulfonyl)-2,3-dihydro-1H-isoindole-1-carboxamide Example 18: 2-Acetyl-N-[4-(1,1,1,3,3,3-hexafluoro-2-{[(1-methoxycyclopropyl)methyl]amino}propan-2-yl)phenyl]-5-(methylsulfonyl)-2,3-dihydro-1H-isoindole-1-carboxamide Example 19: 2-Acetyl-N-{4-[1,1,1,3,3,3-hexafluoro-2-(oxetan-3-ylamino)propan-2-yl]phenyl}-5-(methylsulfonyl)-2,3-dihydro-1H-isoindole-1-carboxamide Example 20: 2-Acetyl-N-{4-[1,1,1,3,3,3-hexafluoro-2-(tetrahydro-2H-pyran-4-ylamino)propan-2-yl]phenyl}-5-(methylsulfonyl)-2,3-dihydro-1H-isoindole-1-carboxamide Example 21: 2-Acetyl-N-(4-{1,1,1,3,3,3-hexafluoro-2-[(2-hydroxyethyl)amino]propan-2-yl}phenyl)-5-(methylsulfonyl)-2,3-dihydro-1H-isoindole-1-carboxamide Example 22: 2-Acetyl-N-[4-(1,1,1,3,3,3-hexafluoro-2-{[3-(methylsulfonyl)propyl]amino}propan-2-yl)phenyl]-5-(methylsulfonyl)-2,3-dihydro-1H-isoindole-1-carboxamide Example 23: 2-Acetyl-N-{4-[1,1,1,3,3,3-hexafluoro-2-(morpholin-4-yl)propan-2-yl]phenyl}-5-(methylsulfonyl)-2,3-dihydro-1H-isoindole-1-carboxamide Example 24: 2-Acetyl-N-{4-[1,1,1,3,3,3-hexafluoro-2-(methylamino)propan-2-yl]phenyl}-5-(methylsulfonyl)-2,3-dihydro-1H-isoindole-1-carboxamide Example 25: 2-Acetyl-N-{4-[2-(dimethylamino)-1,1,1,3,3,3-hexafluoropropan-2-yl]phenyl}-5-(methylsulfonyl)-2,3-dihydro-1H-isoindole-1-carboxamide Example 26: 2-Acetyl-N-[4-(1,1,1,3,3,3-hexafluoro-2-{[2-(methylsulfonyl)ethyl]amino}propan-2-yl)phenyl]-5-(methylsulfonyl)-2,3-dihydro-1H-isoindole-1-carboxamide Example 27: 2-Acetyl-N-[4-(1,1,1,3,3,3-hexafluoro-2-{[2-(propan-2-yloxy)ethyl]amino}propan-2-yl)phenyl]-5-(methylsulfonyl)-2,3-dihydro-1H-isoindole-1-carboxamide

TABLE 2

| Example No. | Structure | MS + NMR |
|---|---|---|
| 17 | 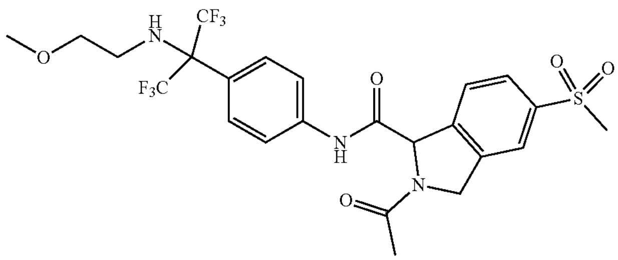 [SMILES: COCCNC(c1ccc(NC(=O)C2c3ccc(S(C)(=O)=O)cc3CN2C(C)=O)cc1)(C(F)(F)F)C(F)(F)F] | HRMS: calculated for $(C_{24}H_{25}F_6N_3O_5S + H)^+$ 582.1497; found (ESI $[M + H]^+$) 582.1500. $^1$H NMR (600 MHz, DMSO-$d_6$, mixture of rotamers, 4*:1) δ 1.99, 2.15* (s, 3H), 2.55-2.59 (m, 2H), 3.21, 3.22* (s, 3H), 3.25 (s, 3H), 3.44 (t, 2H), 3.52-3.90 (m, 1H), 4.76-4.92, 4.99-5.09* (m, 2H), 5.72*, 5.92 (s, 1H), 7.62*, 7.65 (d, 2H), 7.68-7.79 (m, 3H), 7.90 (d, 1H), 7.99*, 8.02 (s, 1H), 10.71*, 10.94 (s, 1H). |
| 18 | 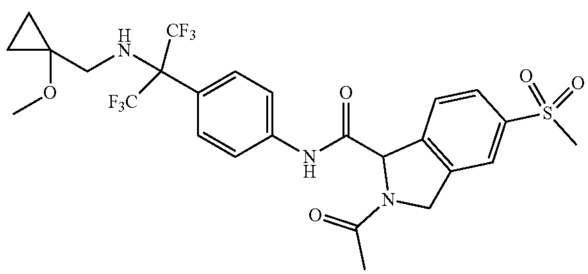 [SMILES: COC1(CNC(c2ccc(NC(=O)C3c4ccc(S(C)(=O)=O)cc4CN3C(C)=O)cc2)(C(F)(F)F)C(F)(F)F)CC1] | HRMS: calculated for $(C_{26}H_{27}F_6N_3O_4S + H)^+$ 608.1653; found (ESI $[M + H]^+$) 608.1669. |
| 19 | 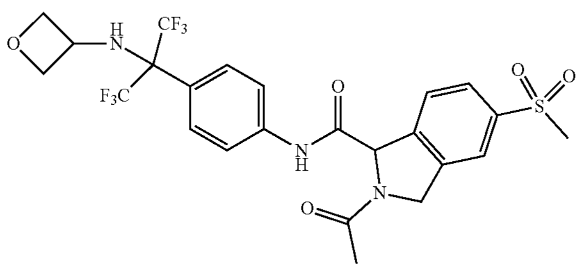 [SMILES: CC(=O)N1Cc2cc(S(C)(=O)=O)ccc2C1C(=O)Nc1ccc(C(NC2COC2)(C(F)(F)F)C(F)(F)F)cc1] | HRMS: calculated for $(C_{24}H_{23}F_6N_3O_5S + H)^+$ 580.1341; found (ESI $[M + H]^+$) 580.1332. $^1$H NMR (600 MHz, DMSO-$d_6$, mixture of rotamers, 4*:1) δ 1.99, 2.15* (s, 3H), 3.21, 3.22* (s, 3H), 3.79-3.89 (m, 1H), 4.46-4.51 (m 2H), 4.55 (t, 2H), 4.85 (d, 1H), 4.76-4.91, 4.99-5.01* (m, 2H), 5.73*, 5.93 (s, 1H), 7.50*, 7.52 (d, 2H), 7.67-7.79 (m, 3H), 7.90 (d, 1H), 8.00*, 8.03 (s, 1H), 10.72*, 10.96 (s, 1H). |
| 20 | 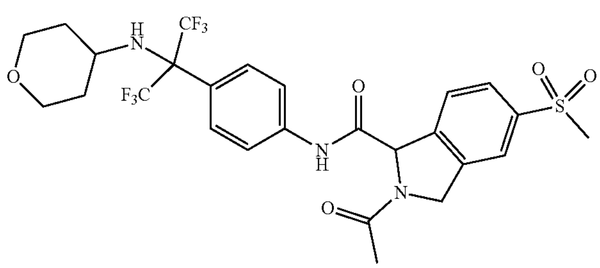 [SMILES: CC(=O)N1Cc2cc(S(C)(=O)=O)ccc2C1C(=O)Nc1ccc(C(NC2CCOCC2)(C(F)(F)F)C(F)(F)F)cc1] | HRMS: calculated for $(C_{26}H_{27}F_6N_3O_5S + H)^+$ 608.1653; found (ESI [M + H]+) 608.1681. $^1$H NMR (600 MHz, DMSO-$d_6$, mixture of rotamers, 4*:1) δ 1.45-1.56 (m, 2H), 1.68 (br d, 2H), 1.99, 2.15* (s, 3H), 2.52 (m, 1H) (under DMSO located by COSY), 3.03-3.11 (m, 2H), 3.21, 3.22* (s, 3H), 3.52 (d, 1H), 3.71-3.77 (m, 2H), 4.75-4.94, 5-5.09* (m, 2H), 5.72*, 5.92 (s, 1H), 7.63*, 7.65 (d, 2H), 7.68-7.79 (m, 3H), 7.91 (dd, 1H), 8.00*, 8.02 (s, 1H), 10.70*, 10.94 (s, 1H). |

TABLE 2-continued

| Example No. | Structure | MS + NMR |
| --- | --- | --- |
| 21 | 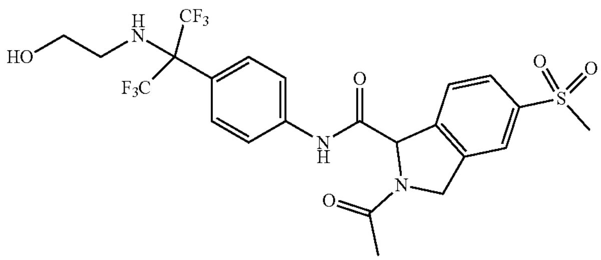 [SMILES: CC(=O)N1Cc2cc(S(C)(=O)=O)ccc2C1C(=O)Nc1ccc(C(NCCO)(C(F)(F)F)C(F)(F)F)cc1] | HRMS: calculated for (C$_{23}$H$_{23}$F$_6$N$_3$O$_5$S + H)$^+$ 568.1341; found (ESI [M + H]$^+$) 568.1348. $^1$H NMR (600 MHz, DMSO-d$_6$, mixture of rotamers, 4*:1) δ 1.99, 2.15* (s, 3H), 2.45-2.51 (m, 2H) (under DMSO located by COSY), 3.21, 3.22* (s, 3H), 3.50 (t, 3H), 4.76-4.92, 4.99-5.09* (m, 2H), 5.73*, 5.93 (s, 1H), 7.6-7.79 (m, 5H), 7.90 (d, 1H), 8.00*, 8.02 (s, 1H), 10.69*, 10.92 (s, 1H). |
| 22 | 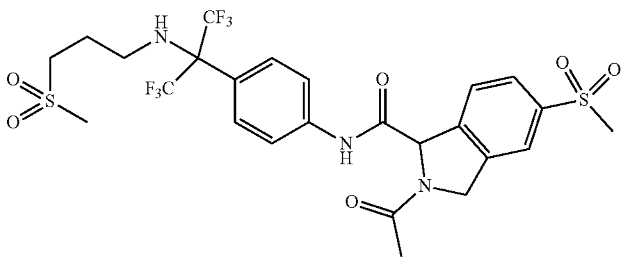 [SMILES: CC(=O)N1Cc2cc(S(C)(=O)=O)ccc2C1C(=O)Nc1ccc(C(NCCCS(C)(=O)=O)(C(F)(F)F)C(F)(F)F)cc1] | HRMS: calculated for (C$_{25}$H$_{27}$F$_6$N$_3$O$_6$S$_2$ + H)$^+$ 644.1324; found (ESI [M + H]$^+$) 644.1346. $^1$H NMR (500 MHz, CDCl$_3$) δ 2.00-2.10 (m, 2H), 2.33 (s, 3H), 2.66-2.74 (m, 2H), 2.94 (s, 3H), 3.08 (s, 3H), 3.10-3.15 (m, 2H), 5.00 (q, 2H), 6.02 (s, 1H), 7.52-7.63 (m, 4H), 7.68 (d, 1H), 7.92 (s, 1H), 7.97 (d, 1H), 9.74 (s, 1H). |
| 23 | 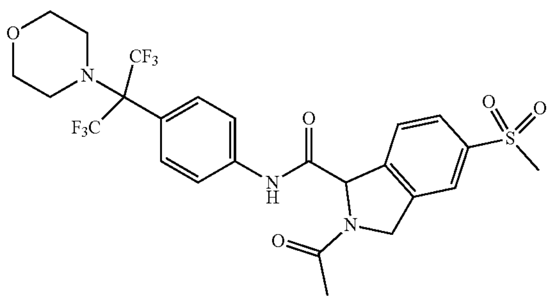 [SMILES: CC(=O)N1Cc2cc(S(C)(=O)=O)ccc2C1C(=O)Nc1ccc(C(N2CCOCC2)(C(F)(F)F)C(F)(F)F)cc1] | HRMS: calculated for (C$_{25}$H$_{25}$F$_6$N$_3$O$_5$S + H)$^+$ 594.1497; found (ESI [M + H]$^+$) 594.1495. $^1$H NMR (600 MHz, DMSO-d$_6$, mixture of rotamers, 4*:1) δ 1.98, 2.14* (s, 3H), 2.75 (br s, 4H), 3.21, 3.22* (s, 3H), 3.62-3.68 (br m, 4H), 4.75-4.91, 4.98-5.09* (m, 2H), 5.72*, 5.93 (d, 1H), 7.64-7.79 (m, 5H), 7.90 (dd, 1H), 8.00*, 8.02 (s, 1H), 10.73*, 10.97 (s, 1H). |
| 24 | 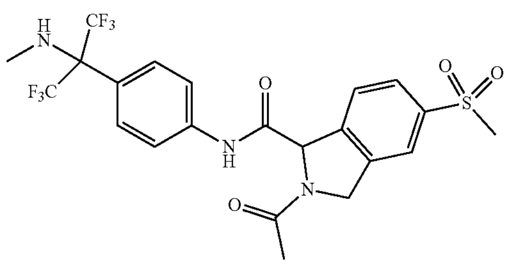 [SMILES: CNC(c1ccc(NC(=O)C2c3ccc(S(C)(=O)=O)cc3CN2C(C)=O)cc1)(C(F)(F)F)C(F)(F)F] | HRMS: calculated for (C$_{22}$H$_{21}$F$_6$N$_3$O$_4$S + H)$^+$ 538.1235; found (ESI [M + H]$^+$) 538.1227. $^1$H NMR (600 MHz, DMSO-d$_6$, mixture of rotamers, 4*:1) δ 1.99, 2.15* (s, 3H), 2.22 (d, 3H), 3.21, 3.22* (s, 3H), 3.79-3.89 (m, 1H), 4.71-4.93, 4.97-5.1* (m, 2H), 5.73*, 5.93 (s, 1H), 7.58*, 7.61 (d, 2H), 7.68-7.79 (m, 3H), 7.90 (d, 1H), 8.00*, 8.03 (s, 1H), 10.70*, 10.93 (s, 1H). |
| 25 | 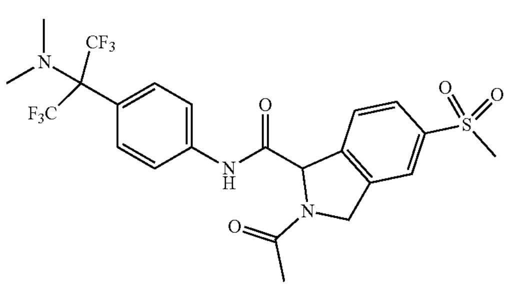 [SMILES: CC(=O)N1Cc2cc(S(C)(=O)=O)ccc2C1C(=O)Nc1ccc(C(N(C)C)(C(F)(F)F)C(F)(F)F)cc1] | HRMS: calculated for (C$_{23}$H$_{23}$F$_6$N$_3$O$_4$S + H)$^+$ 552.1392; found (ESI [M + H]$^+$) 552.1396. $^1$H NMR (600 MHz, DMSO-d$_6$, mixture of rotamers, 4*:1) δ 1.99, 2.15* (s, 3H), 2.54 (s, 6H), 3.21, 3.22* (s, 3H), 4.71-4.96*, 4.98-5.11 (m, 2H), 5.72*, 5.93 (s, 1H), 7.58*, 7.60 (d, 2H), 7.67-7.8 (m, 3H), 7.90 (dd, 1H), 8.00*, 8.02 (s, 1H), 10.70, 10.93* (s, 1H). |

TABLE 2-continued

| Example No. | Structure | MS + NMR |
|---|---|---|
| 26 | 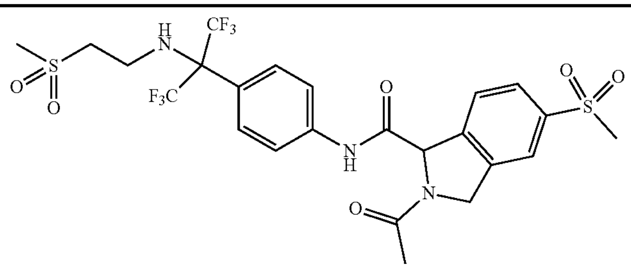 | HRMS: calculated for $(C_{24}H_{25}F_6N_3O_6S_2 + H)^+$ 630.1167; found (ESI [M + H]$^+$) 630.1198. $^1$H NMR (600 MHz, DMSO-d$_6$, mixture of rotamers, 4*:1) δ 1.99, 2.15* (s, 3H), 2.77-2.85 (m, 2H), 3.02 (s, 3H), 3.21, 3.22* (s, 3H), 3.42 (t, 2H), 4.02-4.12 (m, 1H), 4.76-4.94, 4.99-5.11* (m, 2H), 5.72*, 5.93 (s, 1H), 7.63*, 7.65 (d, 2H), 7.69-7.8 (m, 3H), 7.90 (d, 1H), 8.00*, 8.02 (s, 1H), 10.71*, 10.95 (s, 1H). |
| 27 | 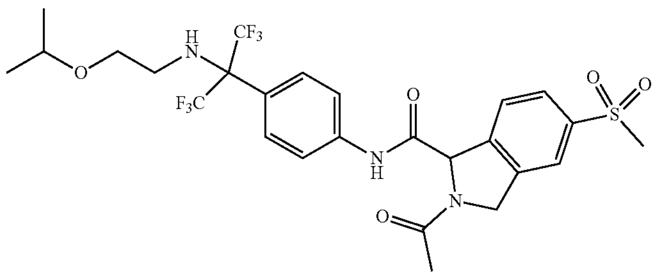 [SMILES: CC(=O)N1Cc2cc(S(C)(=O)=O)ccc2C1C(=O)Nc1ccc(C(NCCOC(C)C)(C(F)(F)F)C(F)(F)F)cc1] | HRMS: calculated for $(C_{26}H_{29}F_6N_3O_5S + H)^+$ 610.1810; found (ESI [M + H]$^+$) 610.1843. $^1$H NMR (600 MHz, DMSO-d$_6$, mixture of rotamers, 4*:1) δ 1.08 (d, 6H), 1.99, 2.15* (s, 3H), 2.51-2.53 (m, 2H) (under DMSO located by COSY), 3.21, 3.22* (s, 3H), 3.47 (t, 2H), 3.52-3.57 (m, 2H), 4.76-4.91, 4.99-5.08* (m, 2H), 5.72*, 5.93 (s, 1H), 7.65*, 7.67 (d, 2H), 7.69-7.79 (m, 3H), 7.90 (dd, 1H), 8.00*, 8.02 (s, 1H), 10.70*, 10.93 (s, 1H). |

Example 28: 2-Acetyl-N-[4-(1,1,1,3,3,3-hexafluoro-2-methoxypropan-2-yl)phenyl]-5-(methylsulfonyl)-2,3-dihydro-1H-isoindole-1-carboxamide Example 29: 2-Acetyl-N-{4-[1,1,1,3,3,3-hexafluoro-2-(1H-1,2,3-triazol-1-yl)propan-2-yl]phenyl}-5-(methylsulfonyl)-2,3-dihydro-1H-isoindole-1-carboxamide

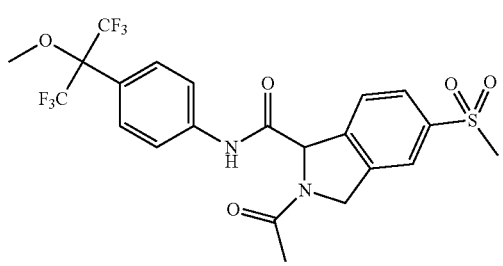

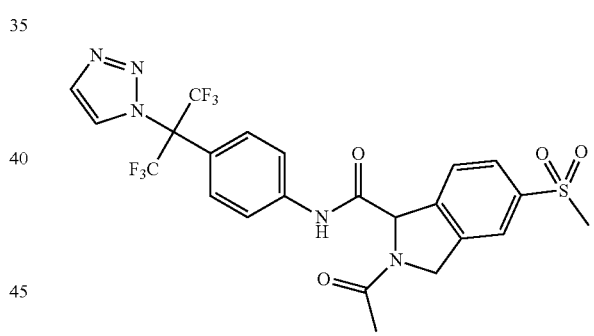

2-Acetyl-N-(4-(1,1,1,3,3,3-hexafluoro-2-hydroxypropan-2-yl)phenyl)-5-(methylsulfonyl)isoindoline-1-carboxamide (Intermediate 3.70 mg, 0.13 mmol), K$_2$CO$_3$ (22.14 mg, 0.16 mmol) and methyl iodide (10.02 μl, 0.16 mmol) were mixed together in DMF (1 mL) and heated at 80° C. for 7 h. The reaction was allowed to cool to rt and diluted with EtOAc. This was washed twice with water and twice with brine. The organic layer was dried using a phase separator cartridge, concentrated in vacuo and purified by preparative SFC-MS (chromatographic conditions: MeOH/NH$_3$ 20 mM, EP; column: Waters Acquity UPC2 BEH 2-EP 3.5 μm 3×100 mm) to give the title compound (42.5 mg, 59.1%) HRMS: calculated for $(C_{22}H_{20}F_6N_2O_5S+H)^+$ 539.1075; found (ESI [M+H]$^+$) 539.1088. $^1$H NMR (600 MHz, DMSO-d$_6$, mixture of rotamers, 4*:1) δ 1.99, 2.15* (s, 3H), 3.21, 3.22* (s, 3H), 3.42 (br s, 3H), 4.75-4.95, 4.99-5.10* (m, 2H), 5.73*, 5.94 (s, 1H), 7.52*, 7.55 (d, 2H), 7.70 (d, 1H), 7.76-7.81*, 7.82-7.84 (m, 2H), 7.91 (dd, 1H), 8.00*, 8.03 (s, 1H), 10.78*, 11.01 (s, 1H).

2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide (Intermediate 3, 0.080 g, 0.15 mmol) was dissolved in ACN (2 ml) and triethylamine (0.063 ml, 0.46 mmol). Methanesulfonic anhydride (0.080 g, 0.46 mmol) in ACN (2 ml) was added and the resulting mixture was stirred at rt for 0.5 h. 1H-1,2,3-triazole (0.053 g, 0.76 mmol) in ACN (1 ml) was added and the resulting mixture was stirred at 50° C. for 0.5 h. The mixture was concentrated in vacuo and the residue partitioned between EtOAc and 0.5M aqueous HCl. The layers were separated and the organic layer was dried using a phase separator cartridge and then concentrated in vacuo. A sample for biological screening was purified using SFC1-MS (chromatographic conditions: MeOH/NH$_3$ 20 mM; column: Waters BEH 2-EP 5 μm 30×250 mm) to afford the title compound (4.30 mg, 4.90%). HRMS: calculated for $(C_{23}H_{19}F_6N_5O_4S+H)^+$ 576.1140; found (ESI [M+H]$^+$) 576.1146. $^1$H NMR (600 MHz, DMSO-d$_6$, mixture of rotamers, 4*:1) δ 1.98, 2.15* (s, 3H), 3.21, 3.22* (s, 3H), 4.74-4.94, 4.99-5.08* (m, 2H), 5.73*, 5.94 (s, 1H), 7.33*, 7.34 (d, 2H), 7.68*, 7.77 (d, 1H), 7.75-7.84 (m, 2H), 7.91 (dd, 1H), 8.00*, 8.03 (s, 1H), 8.04*, 8.05 (d, 1H), 8.35*, 8.36 (d, 1H), 10.84*, 11.07 (s, 1H).

Example 30: 2-Acetyl-N-{4-[1,1,1,3,3,3-hexafluoro-2-(2-methyl-2H-tetrazol-5-yl)propan- 2-yl]phenyl}-5-(methylsulfonyl)-2,3-dihydro-1H-isoindole-1-carboxamide

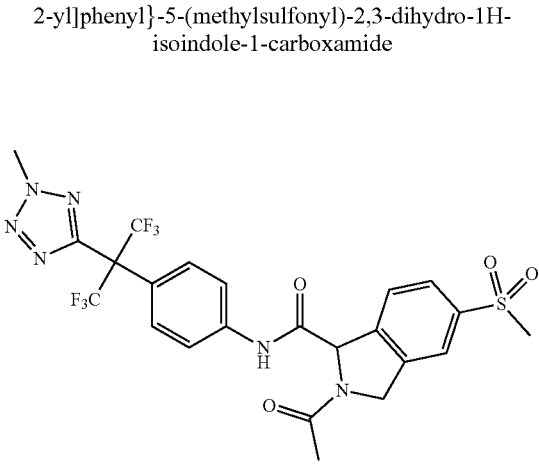

Step 1: 5-Methylsulfonyl-N-[4-[2,2,2-trifluoro-1-(2-methyltetrazol-5-yl)-1-

(trifluoromethyl)ethyl]phenyl]isoindoline-1-carboxamide

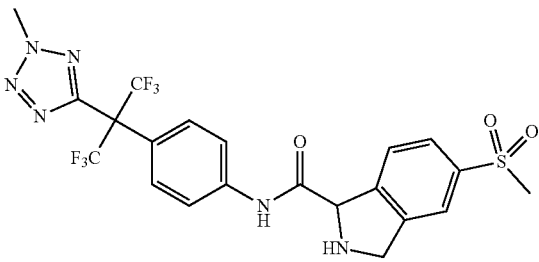 [SMILES: Cn1nnc(C(c2ccc(NC(=O)C3NCc4cc(S(C)(=O)=O)ccc43)cc2)(C(F)(F)F)C(F)(F)F)n1]

5M HCL in IPA (0.5 mL, 2.50 mmol) was added to tert-butyl 1-((4-(1,1,1,3,3,3-hexafluoro-2-(2-methyl-2H-tetrazol-5-yl)propan-2-yl)phenyl)carbamoyl)-5-(methylsulfonyl)isoindoline-2-carboxylate (Intermediate 7, 51.9 mg, 0.08 mmol) in isopropyl acetate (0.5 mL). The reaction was stirred at rt overnight. The reaction was concentrated in vacuo and the residue was co-evaporated with EtOAc/heptane (1:1). The HCl salt of the product was obtained as a grey solid. The yield was assumed quantitative and the material was used directly in the next step.

LC/MS: m/z=549 [M+H]+.

Step 2: 2-Acetyl-N-{4-[1,1,1,3,3,3-hexafluoro-2-(2-methyl-2H-tetrazol-5-yl)propan-2- yl]phenyl}-5-(methylsulfonyl)-2,3-dihydro-1H-isoindole-1-carboxamide

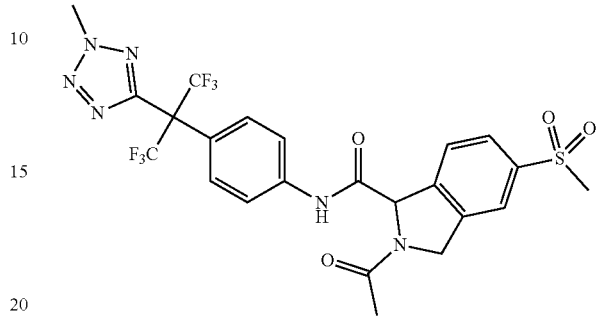

The HCL salt of N-(4-(1,1,1,3,3,3-hexafluoro-2-(2-methyl-2H-tetrazol-5-yl)propan-2-yl)phenyl)-5-(methylsulfonyl)isoindoline-1-carboxamide (product of step 1 of the synthesis of Example 30, 46.8 mg, 0.08 mmol) was suspended in DCM (2 mL) and to this triethylamine (0.033 mL, 0.24 mmol), acetic acid (9.16 µl, 0.16 mmol) and T3P (50% solution in EtOAc, 50.9 mg, 0.16 mmol) was added. The reaction was stirred at rt for 30 min. The reaction was diluted with DCM and washed with 0.5M aqueous HCl and then with saturated aqueous NaHCO$_3$. The layers were separated using a phase separator cartridge and the DCM removed in vacuo. The residue was purified by flash chromatography eluting with 20-100% EtOAc in heptane to afford the title compound (20 mg, 42.3%).

HRMS: calculated for (C$_{23}$H$_{20}$F$_6$N$_6$O$_4$S+H)+ 591.1249; found (ESI [M+H]+) 591.1249. $^1$H NMR (600 MHz, DMSO-d$_6$, mixture of rotamers, 4*:1) δ 1.98, 2.14* (s, 3H), 3.20, 3.21* (s, 3H), 4.47, 4.48* (s, 3H), 4.75-4.93, 4.98-5.08* (m, 2H), 5.71*, 5.93 (s, 1H), 7.22*, 7.25 (d, 2H), 7.62-7.78 (m, 3H), 7.89 (dd, 1H), 7.99*, 8.02 (s, 1H), 10.77*, 11.00 (s, 1H).

Example 31: Methyl 4,4,4-trifluoro-3-[4-[(5-methylsulfonylisoindoline-1- carbonyl)amino]phenyl]-3-(trifluoromethyl)butanoate

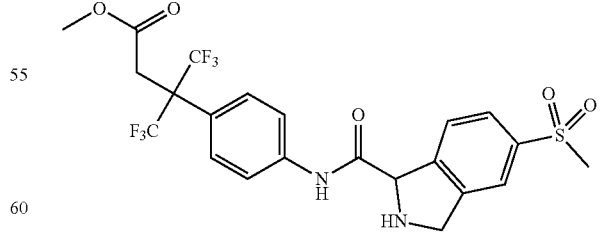

To a solution of tert-butyl 5-(methylsulfonyl)-1-((4-(1,1,1-trifluoro-4-methoxy-4-oxo-2-(trifluoromethyl)butan-2-yl)phenyl)carbamoyl)isoindoline-2-carboxylate (Intermediate 8, 364 mg, 0.57 mmol) in DCM (4 mL), TFA (1.5 mL, 19.47 mmol) was added and the resulting solution was stirred at rt for 45 min. The volatiles were removed in vacuo. The residue was dissolved in EtOAc (200 mL), washed with saturated aqueous NaHCO₃ solution (2×15 mL), dried over Na₂SO₄, filtered and the filtrate was concentrated in vacuo to give the title compound as a crude (260 mg, 85%) most of which was used in the next step without further purification. The compound can further be purified using RP-HPLC (chromatographic conditions: gradient 5-95% ACN in 0.2% NH₃, pH10; column: Waters Xbridge C18 5μ ODB 19×150 mm).

HRMS: calculated for $(C_{22}H_{20}F_6N_2O_5S+H)^+$ 539.1075; found (ESI [M+H]⁺) 539.1101. ¹H NMR (600 MHz, DMSO-d₆); δ 3.18 (s, 3H); 3.53 (s, 3H); 3.58 (s, 2H); 4.42 (q, 2H); 5.13 (s, 1H); 7.58 (d, 2H); 7.73 (d, 1H); 7.75-7.77 (m, 2H); 7.82 (d, 1H); 7.88 (s, 1H); 10.39 (s, 1H).

Example 32: Methyl 3-[4-({[2-acetyl-5-(methyl-sulfonyl)-2,3-dihydro-1H-isoindol-1-yl]carbonyl}amino)phenyl]-4,4,4-trifluoro-3-(trifluoromethyl)butanoate

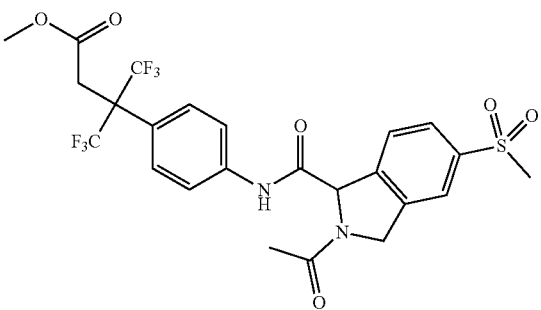 [SMILES: COC(=O)CC(c1ccc(NC(=O)C2c3ccc(S(C)(=O)=O)cc3CN2C(C)=O)cc1)(C(F)(F)F)C(F)(F)F]

To a solution of methyl 4,4,4-trifluoro-3-(4-(5-(methylsulfonyl)isoindoline-1-carboxamido)phenyl)-3-(trifluoromethyl)butanoate (Example 31, 200 mg, 0.37 mmol) in pyridine (2 mL), Ac₂O (0.105 mL, 1.11 mmol) was added and the reaction mixture was stirred at rt over night. The volatiles were removed in vacuo. The residue was dissolved in methanol (3 mL), concentrated in vacuo. This process was repeated for several times to give the title compound (216 mg, 100%) as a crude. Only a small portion was purified by SFC1-MS (chromatographic conditions: MeOH/NH₃ 20 mM, BEH; column: Waters BEH 5 μm 30×250 mm) the rest was used in subsequent steps without further purification.

HRMS: calculated for $(C_{24}H_{22}F_6N_2O_6S+H)^+$ 581.1181; found (ESI [M+H]⁺) 581.1218. ¹H NMR (600 MHz, DMSO-d₆, mixture of rotamers, 4*:1) δ 1.99, 2.15* (s, 3H); 3.21, 3.22* (s, 3H); 3.53, 3.54* (s, 3H); 3.58*, 3.59 (s, 2H); 4.79-5.07 (m, 2H); 5.72*, 5.92 (s, 1H); 7.55-7.65 (m, 2H); 7.65-7.79 (m, 3H), 7.90 (d, 1H), 7.96-8.04 (m, 1H), 10.72*, 10.95 (s, 1H).

Example 33: 2-Acetyl-5-(methylsulfonyl)-N-{4-[1,1,1-trifluoro-4-hydroxy-2-(trifluoromethyl)butan-2-yl]phenyl}-2,3-dihydro-1H-isoindole-1-carboxamide

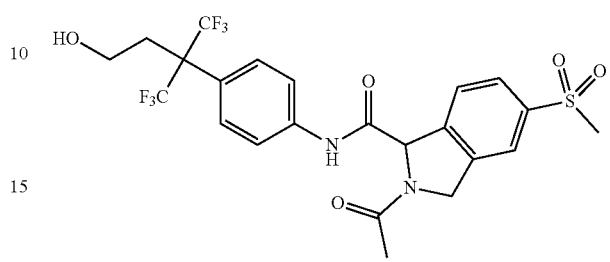

To a suspension of sodium tetrahydroborate (0.038 mL, 1.07 mmol) in THF (0.5 mL), a solution of methyl 3-(4-(2-acetyl-5-(methylsulfonyl)isoindoline-1-carboxamido)phenyl)-4,4,4-trifluoro-3-(trifluoromethyl)butanoate (Example 32, 156 mg, 0.27 mmol) in THF (1.5 mL) was added in portions. After addition was completed the reaction mixture was stirred at rt. After 2 h an additional portion of sodium tetrahydroborate (0.038 mL, 1.07 mmol) was added and the reaction mixture was stirred at rt over night. An additional portion of sodium tetrahydroborate (0.038 mL, 1.07 mmol) was added followed by dropwise addition of methanol (1 mL) and the reaction mixture was stirred at rt for 72 h. The reaction mixture was acidified to pH 2 by addition to diluted aqueous HCl in an ice water bath and extracted with EtOAc (150 mL). The organic layer was washed with water (2×25 mL), dried over Na₂SO₄, filtered and the filtrate was concentrated in vacuo. The residue was dissolved in DMSO (2 mL), filtered and purified using RP-HPLC (chromatographic conditions: gradient 5-95% ACN in 0.1M HCO₂H, pH 3; column: Waters Sunfire C18 ODB 5μ 30×150 mm) to give 19.5 mg (13%) of the title compound.

HRMS: calculated for $(C_{23}H_{22}F_6N_2O_5S+H)^+$ 553.1232; found (ESI [M+H]⁺) 553.1241. ¹H NMR (600 MHz, DMSO-d₆, mixture of rotamers, 4*:1) δ 1.99, 2.15* (s, 3H); 2.53-2.56 (m, 2H); 3.21, 3.22* (s, 3H); 3.33-3.40 (m, 2H); 4.77-5.07 (m, 3H); 5.72*, 5.93 (s, 1H); 7.54-7.60 (m, 2H); 7.68-7.79 (m, 3H); 7.90 (d, 1H); 7.98-8.05 (m, 1H); 10.73*, 10.96 (s, 1H).

Example 34: 2-Acetyl-N-(4-{1,1,1,3,3,3-hexafluoro-2-[(3-methyl-1,2,4-oxadiazol-5-yl)methyl]propan-2-yl}phenyl)-5-(methylsulfonyl)-2,3-dihydro-1H-isoindole-1-carboxamide

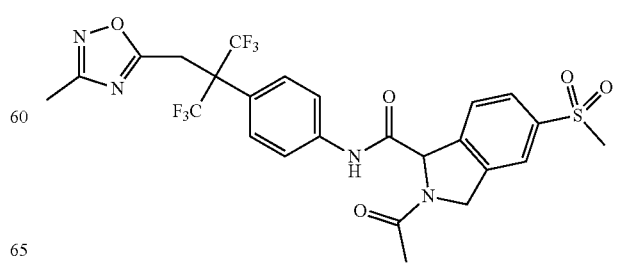

(Z)—N'-hydroxyacetimidamide (30.6 mg, 0.41 mmol) was dissolved in THF (0.4 mL) at rt. NaH (16.54 mg, 0.41 mmol) was added and the reaction mixture was stirred at rt for 1 h. To this reaction mixture a solution of methyl 3-(4-(2-acetyl-5-(methylsulfonyl)isoindoline-1-carboxamido)phenyl)-4,4,4-trifluoro-3-(trifluoromethyl)butanoate (Example 32, 60 mg, 0.10 mmol) in THF (0.6 mL) was added. After addition was completed the reaction mixture was stirred at 70° C. for 30 min. The reaction mixture was cooled to rt, quenched with methanol, diluted by addition of EtOAc (150 mL), washed successively with diluted aqueous HCl (2×15 mL) and water (2×15 mL). After drying over $Na_2SO_4$ and filtration, the filtrate was concentrated in vacuo. The residue was dissolved in DMSO (2 mL), filtered and purified using SFC1-MS (chromatographic conditions: MeOH/$NH_3$ 20 mM; column: Waters BEH 2-EP 5 μm 30×250 mm). An amount of 2.7 mg (4%) of the title compound was isolated.

LC/MS: m/z=603 [M−H]−.

HRMS: calculated for $(C_{25}H_{22}F_6N_4O_5S+H)^+$ 605.1293; found (ESI [M+H]+) 605.1295.

Example 35: 2-Acetyl-5-(methylsulfonyl)-N-{4-[1,1,1,4-tetrafluoro-2-(trifluoromethyl)butan-2-yl]phenyl}-2,3-dihydro-1H-isoindole-1-carboxamide

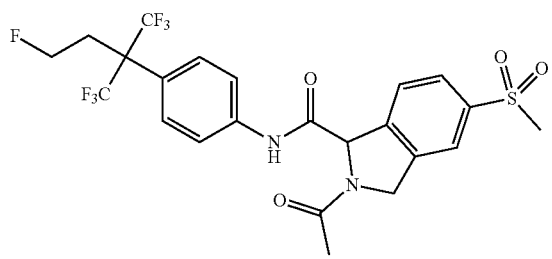 [SMILES: CC(=O)N1Cc2cc(S(C)(=O)=O)ccc2C1C(=O)Nc1ccc(C(CCF)(C(F)(F)F)C(F)(F)F)cc1]

Step 1: N-[4-[3-fluoro-1,1-bis(trifluoromethyl)propyl]phenyl]-5-methylsulfonyl-isoindoline-1-carboxamide

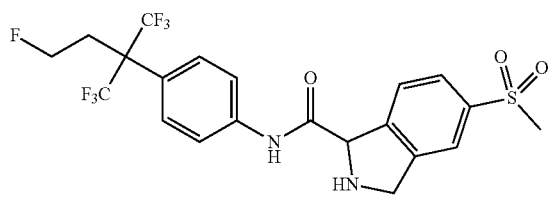 [SMILES: CS(=O)(=O)c1ccc2c(c1)CNC2C(=O)Nc1ccc(C(CCF)(C(F)(F)F)C(F)(F)F)cc1]

To a solution of tert-butyl 5-(methylsulfonyl)-1-((4-(1,1,1,4-tetrafluoro-2-(trifluoromethyl)butan-2-yl)phenyl)carbamoyl)isoindoline-2-carboxylate (Intermediate 9, 270 mg, 0.44 mmol) in DCM (3 mL), TFA (1 mL, 12.98 mmol) was added and the reaction mixture was stirred at rt for 45 min. The volatiles were removed in vacuo. The residue was dissolved in EtOAc (150 mL), washed with saturated aqueous $NaHCO_3$ solution (2×15 mL), dried over $Na_2SO_4$, filtered and the filtrate was concentrated in vacuo to give a crude product (220 mg) which was used in the next step without any purification.

LC/MS: m/z=513 [M+H]+.

Step 2: 2-Acetyl-5-(methylsulfonyl)-N-{4-[1,1,1,4-tetrafluoro-2-(trifluoromethyl)butan-2-yl]phenyl}-2,3-dihydro-1H-isoindole-1-carboxamide

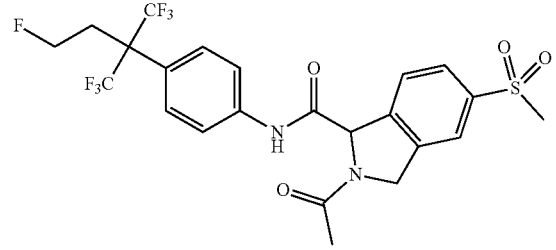 [SMILES: CC(=O)N1Cc2cc(S(C)(=O)=O)ccc2C1C(=O)Nc1ccc(C(CCF)(C(F)(F)F)C(F)(F)F)cc1]

To a solution of 5-(methylsulfonyl)-N-(4-(1,1,1,4-tetrafluoro-2-(trifluoromethyl)butan-2-yl)phenyl)isoindoline-1-carboxamide (product of step 1 of the synthesis of Example 35, 220 mg, 0.43 mmol) in pyridine (3 mL), $Ac_2O$ (0.122 mL, 1.29 mmol) was added and the reaction mixture was stirred at rt for 1 h. After addition of methanol (0.5 mL) the volatiles were removed in vacuo. The residue was dissolved in EtOAc (150 mL), washed with water (3×15 mL), dried over $Na_2SO_4$, filtered and the filtrate was concentrated in vacuo. The residue was dissolved in DMSO (2 mL), filtered and purified using RP-HPLC (chromatographic conditions: gradient 5-95% ACN in 0.2% $NH_3$, pH10; column: Waters Xbridge C18 5μ ODB 30×150 mm) to give 37 mg (16%) of the title compound. HRMS: calculated for $(C_{23}H_{21}F_7N_2O_4S+H)^+$ 555.1188; found (ESI [M+H]+) 555.1201. $^1$H NMR (600 MHz, DMSO-$d_6$, mixture of rotamers, 4*:1) 1.99, 2.15* (s, 3H); 2.72-2.95 (m, 2H); 3.21, 3.22* (s, 3H); 3.95-4.04, 4.42-4.55* (m, 2H); 4.78-5.07 (m, 2H); 5.72*, 5.93 (s, 1H); 7.54-7.79 (m, 5H); 7.90 (d, 1H); 8.00*, 8.03 (s, 1H); 10.74*, 10.98 (s, 1H).

Example 36: 2-Acetyl-N-{4-[2-(cyanomethyl)-1,1,1,3,3,3-hexafluoropropan-2-yl]phenyl}-5-(methylsulfonyl)-2,3-dihydro-1H-isoindole-1-carboxamide

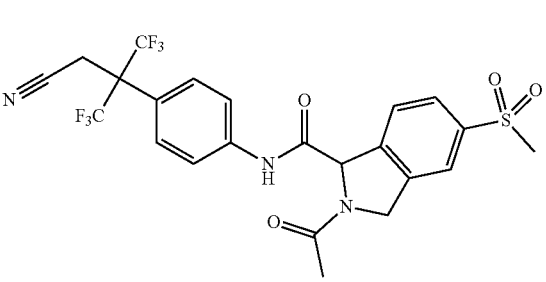 [SMILES: CC(=O)N1Cc2cc(S(C)(=O)=O)ccc2C1C(=O)Nc1ccc(C(CC#N)(C(F)(F)F)C(F)(F)F)cc1]

Step 1: N-[4-[1-(Cyanomethyl)-2,2,2-trifluoro-1-(trifluoromethyl)ethyl]phenyl]-5-methylsulfonyl-isoindoline-1-carboxamide

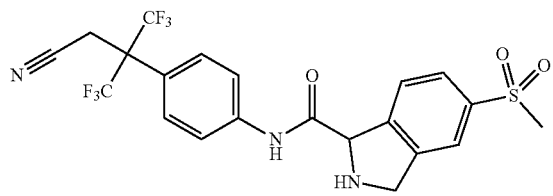 [SMILES: CS(=O)(=O)c1ccc2c(c1)CNC2C(=O)Nc1ccc(C(CC#N)(C(F)(F)F)C(F)(F)F)cc1]

To a solution of tert-butyl 1-((4-(2-(cyanomethyl)-1,1,1,3,3,3-hexafluoropropan-2-yl)phenyl)carbamoyl)-5-(methylsulfonyl)isoindoline-2-carboxylate (Intermediate 10, 32 mg, 0.05 mmol) in DCM (0.6 mL), TFA (0.2 mL, 2.60 mmol) was added and the reaction mixture was stirred at rt for 1 h. The volatiles were removed in vacuo to give the title compound as a crude (33 mg, 100%) which was used in the next step without further purification.
LC/MS: m/z=506 [M+H]$^+$.

Step 2: 2-Acetyl-N-{4-[2-(cyanomethyl)-1,1,1,3,3,3-hexafluoropropan-2-yl]phenyl}-5-(methylsulfonyl)-2,3-dihydro-1H-isoindole-1-carboxamide

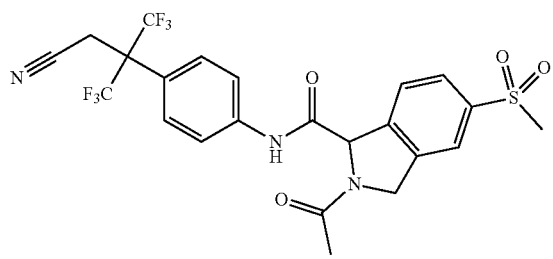 [SMILES: CC(=O)N1Cc2cc(S(C)(=O)=O)ccc2C1C(=O)Nc1ccc(C(CC#N)(C(F)(F)F)C(F)(F)F)cc1]

To a solution of N-(4-(2-(cyanomethyl)-1,1,1,3,3,3-hexafluoropropan-2-yl)phenyl)-5-(methylsulfonyl)isoindoline-1-carboxamide 2,2,2-trifluoroacetate (product of step 1 of the synthesis of Example 36, 33 mg, 0.05 mmol) in pyridine (0.5 mL), acetic anhydride (0.015 mL, 0.16 mmol) was added and the reaction mixture was stirred at rt for 2 h. The volatiles were removed in vacuo. The residue was dissolved in methanol (2 mL) and concentrated in vacuo. This process was repeated several times to give the title compound as a crude which was dissolved in DMSO (1.5 mL), filtered and purified using SFC1-MS (chromatographic conditions: MeOH/NH$_3$ 20 mM; column: Waters BEH 2-EP 5 μm 30×250 mm) to give 18.9 mg (65%) of the title compound.
HRMS: calculated for (C$_{23}$H$_{19}$F$_6$N$_3$O$_4$S+H)$^+$ 548.1078; found (ESI [M+H]$^+$) 548.1068. $^1$H NMR (600 MHz, DMSO-d$_6$, mixture of rotamers, 4*:1) δ 1.99, 2.15* (s, 3H); 3.21, 3.22* (s, 3H); 4.11*, 4.12 (s, 2H); 4.77-5.09 (m, 2H); 5.73*, 5.94 (s, 1H); 7.69-7.73 (m, 3H); 7.76-7.81 (m, 2H); 7.89 (dd, 1H); 7.97-8.05 (m, 1H); 10.79*, 11.02 (s, 1H).

Example 37: Ethyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate

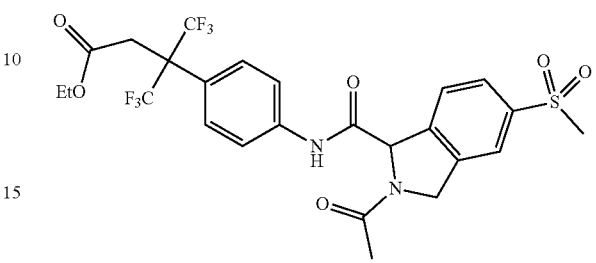

Step 1: Ethyl 4,4,4-trifluoro-3-[4-[(5-methylsulfonylisoindoline-1-carbonyl)amino]phenyl]-3-(trifluoromethyl)butanoate

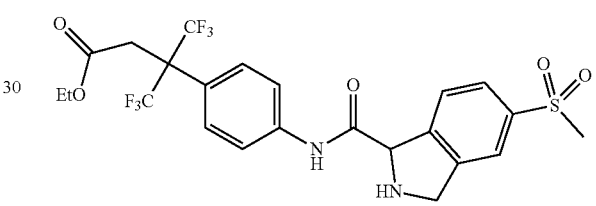

To a solution of tert-butyl 1-((4-(4-ethoxy-1,1,1-trifluoro-4-oxo-2-(trifluoromethyl)butan-2-yl)phenyl)carbamoyl)-5-(methylsulfonyl)isoindoline-2-carboxylate (Intermediate 11, 203 mg, 0.31 mmol) in DCM (2 mL), TFA (0.5 mL, 6.49 mmol) was added and the resulting reaction mixture was stirred at rt for 45 min. The volatiles were removed in vacuo and the residue was dissolved in EtOAc (200 mL), washed with saturated aqueous NaHCO$_3$ solution (2×15 mL), dried over Na$_2$SO$_4$, filtered and the filtrate was concentrated in vacuo to give a crude product (170 mg, 99%), which was used in the next step without further purification.
LC/MS: m/z=553 [M+H]$^+$.

Step 2: Ethyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate

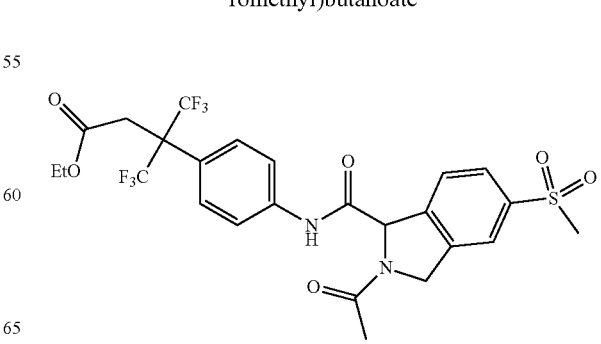

To a solution of ethyl 4,4,4-trifluoro-3-(4-(5-(methyl-sulfonyl)isoindoline-1-carboxamido)phenyl)-3-(trifluoromethyl)butanoate (product of step 1 of the synthesis of Example 37, 170 mg, 0.31 mmol) in pyridine (2 mL), Ac$_2$O (0.116 mL, 1.23 mmol) was added and the reaction mixture was stirred at rt for 1 h. The volatiles were removed in vacuo. The residue was dissolved in methanol (3 mL), concentrated in vacuo. This process was repeated for several times. The crude material was purified using RP-HPLC (chromatographic conditions: gradient 5-95% ACN in 0.2% NH$_3$, pH10; column: Waters Xbridge C18 5µ ODB 30×150 mm) to give 81.4 mg (45%) of the title compound. HRMS: calculated for (C$_{25}$H$_{24}$F$_6$N$_2$O$_6$S+H)$^+$ 595.1337; found (ESI [M+H]$^+$) 595.1324. $^1$H NMR (600 MHz, DMSO-d$_6$, mixture of rotamers, 4*:1) δ 1.03-1.10 (m, 3H); 1.99, 2.15* (s, 3H); 3.21, 3.22* (s, 3H); 3.55*, 3.56 (s, 2H); 3.99 (q, 2H); 4.78-5.07 (m, 2H); 5.72*, 5.92 (s, 1H); 7.55-7.79 (m, 5H); 7.89 (dd, 1H); 7.97-8.05 (s, 1H); 10.70*, 10.93 (s, 1H).

Example 38: 2-Acetyl-N-{4-[4-(cyclopropylamino)-1,1,1-trifluoro-4-oxo-2-

(trifluoromethyl)butan-2-yl]phenyl}-5-(methylsulfonyl)-2,3-dihydro-1H-isoindole-1- carboxamide

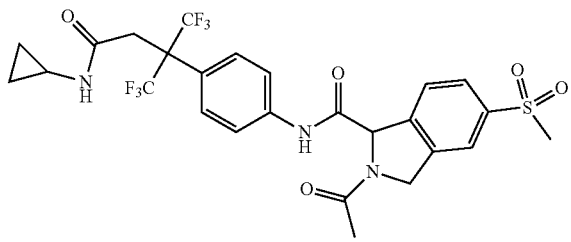 [SMILES: CC(=O)N1Cc2cc(S(C)(=O)=O)ccc2C1C(=O)Nc1ccc(C(CC(=O)NC2CC2)(C(F)(F)F)C(F)(F)F)cc1]

Step 1: N-[4-[3-(Cyclopropylamino)-3-oxo-1,1-bis(trifluoromethyl)propyl]phenyl]-5- methylsulfonyl-isoindoline-1-carboxamide

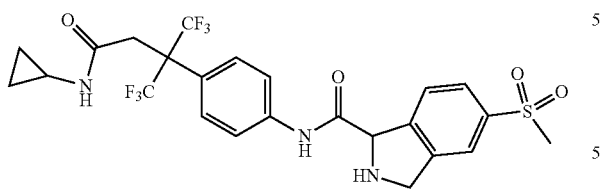

To a solution of tert-butyl 1-((4-(4-(cyclopropylamino)-1,1,1-trifluoro-4-oxo-2-(trifluoromethyl)butan-2-yl)phenyl)carbamoyl)-5-(methylsulfonyl)isoindoline-2-carboxylate (Intermediate 12, 58 mg, 0.09 mmol) in DCM (1 mL), TFA (0.3 mL, 3.89 mmol) was added and the resulting solution was stirred at rt for 40 min. The volatiles were removed in vacuo to give a crude product (59 mg, 100%), which was used in the next step.

LC/MS: m/z=564 [M+H]$^+$.

Step 2: 2-Acetyl-N-{4-[4-(cyclopropylamino)-1,1,1-trifluoro-4-oxo-2-(trifluoromethyl)

butan-2-yl]phenyl}-5-(methylsulfonyl)-2,3-dihydro-1H-isoindole-1-carboxamide

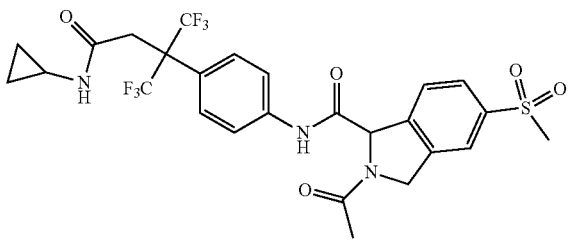 [SMILES: CC(=O)N1Cc2cc(S(C)(=O)=O)ccc2C1C(=O)Nc1ccc(C(CC(=O)NC2CC2)(C(F)(F)F)C(F)(F)F)cc1]

To a solution of N-(4-(4-(cyclopropylamino)-1,1,1-trifluoro-4-oxo-2-(trifluoromethyl)butan-2-yl)phenyl)-5-(methylsulfonyl)isoindoline-1-carboxamide 2,2,2-trifluoroacetate (product of step 1 of the synthesis of Example 38, 59 mg, 0.09 mmol) in pyridine (1 mL), Ac$_2$O (0.025 mL, 0.26 mmol) was added and the reaction mixture was stirred at rt for 2 h. The volatiles were removed in vacuo. The residue was dissolved in methanol (2 mL), and subsequently concentrated in vacuo. This process was repeated several times. The residue was dissolved in DMSO (1.5 mL), filtered and the filtrate was purified using SFC1-MS (chromatographic conditions: MeOH/NH$_3$ 20 mM; column: Waters BEH 5 µm 30×250 mm) to give 35.4 mg (67%) of the title compound.

LC/MS: m/z=604 [M−H]$^-$. $^1$H NMR (500 MHz, DMSO-d$_6$, mixture of rotamers, 4*:1) δ 0.29-0.32 (m 2H), 0.55-0.58 (m, 2H), 1.99, 2.15* (s, 3H); 2.47-2.49 (m, 1H); 3.21, 3.22* (s, 3H); 3.26*, 3.27 (s, 2H); 4.79-5.07 (m, 2H); 5.73*, 5.93 (s, 1H); 7.56-7.79 (m, 5H); 7.90 (d, 1H); 7.98-8.04 (m, 1H); 8.24-8.26 (m, 1H); 10.68*, 10.91 (s, 1H).

Example 39: 2-Acetyl-5-(methylsulfonyl)-N-{4-[1,1,1-trifluoro-4-(3-fluoro-3- methylazetidin-1-yl)-4-oxo-2-(trifluoromethyl)butan-2-yl]phenyl}-2,3-dihydro-1H-isoindole- 1-carboxamide

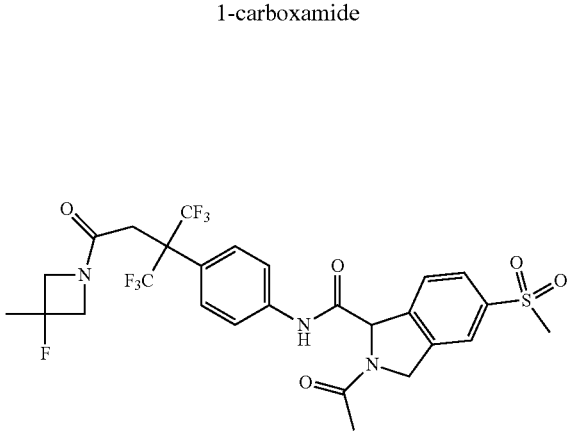

Step 1: 3-[4-[(2-acetyl-5-methylsulfonyl-isoindoline-1-carbonyl)amino]phenyl]-4,4,4- trifluoro-3-(trifluoromethyl)butanoic acid

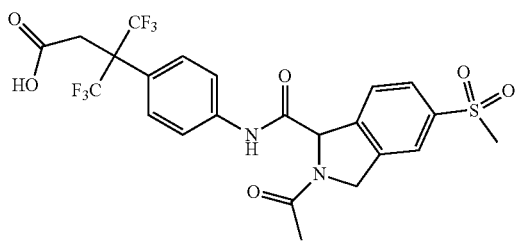 [SMILES: CC(=O)N1Cc2cc(S(C)(=O)=O)ccc2C1C(=O)Nc1ccc(C(CC(=O)O)(C(F)(F)F)C(F)(F)F)cc1]

To a solution of methyl 3-(4-(2-acetyl-5-(methylsulfonyl)isoindoline-1-carboxamido)phenyl)-4,4,4-trifluoro-3-(trifluoromethyl)butanoate (Example 32, 705 mg, 1.21 mmol) in 1,4-dioxane (8 mL), aqueous NaOH (1.822 mL, 3.64 mmol) was added and the reaction mixture was stirred at rt for 2 h 40 mins. The reaction mixture was diluted by addition of EtOAc (50 mL), ice (25 g) was added, and the pH was adjusted to ca 2 by addition of diluted aqueous HCl. The mixture was extracted with EtOAc (200 mL). The organic layer was washed with water (1×25 mL), dried over $Na_2SO_4$, filtered and the filtrate was concentrated in vacuo to give a crude (670 mg, 97%), which was used without further purification.

LC/MS: m/z=567 [M+H]$^+$. $^1$H NMR (600 MHz, DMSO-d$_6$, mixture of rotamers, 4*:1) δ 1.99, 2.15* (s, 3H); 3.21, 3.22* (s, 3H); 3.47*, 3.48 (s, 2H); 4.78-5.07 (m, 2H); 5.73*, 5.93 (s, 1H); 7.58-7.79 (m, 5H); 7.90 (d, 1H); 7.97-8.06 (s, 1H); 10.68*, 10.91 (s, 1H); 12.70 (br.s, 1H).

Step 2: 2-Acetyl-5-(methylsulfonyl)-N-{4-[1,1,1-trifluoro-4-(3-fluoro-3-methylazetidin-1- yl)-4-oxo-2-(trifluoromethyl)butan-2-yl]phenyl}-2,3-dihydro-1H-isoindole-1-carboxamide

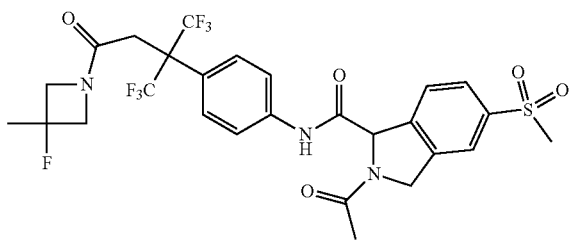 [SMILES: CC(=O)N1Cc2cc(S(C)(=O)=O)ccc2C1C(=O)Nc1ccc(C(CC(=O)N2CC(C)(F)C2)(C(F)(F)F)C(F)(F)F)cc1]

To a mixture of 3-fluoro-3-methylazetidine hydrochloride (18.62 mg, 0.15 mmol) and 3-(4-(2-acetyl-5-(methylsulfonyl)isoindoline-1-carboxamido)phenyl)-4,4,4-trifluoro-3-(trifluoromethyl)butanoic acid (product of step 1 of the synthesis of Example 39, 70 mg, 0.12 mmol) in EtOAc (1 mL), Et$_3$N (0.069 mL, 0.49 mmol) was added followed by T3P (50% in EtOAc, 0.147 mL, 0.25 mmol) and the reaction mixture was stirred at rt for 45 min. The reaction mixture was partitioned between EtOAc (150 mL) and water (15 mL). The layers were separated in a phase separator and the organic layer was washed further with water (2×20 mL), dried over $Na_2SO_4$, filtered and the filtrate was purified using RP-HPLC (chromatographic conditions: gradient 5-95% ACN in 0.1M HCO$_2$H, pH3; column: Waters Sunfire C18 ODB 5μ 30×150 mm) to give 16.4 mg (21%) of the title compound. HRMS: calculated for $(C_{27}H_{26}F_7N_3O_5S+H)^+$ 638.1559; found (ESI [M+H]$^+$) 638.1541. $^1$H NMR (600 MHz, DMSO-d$_6$, mixture of rotamers, 4*:1) δ 1.57 (d, 3H); 1.99, 2.15* (s, 3H); 3.21, 3.22* (s, 3H); 3.28-3.38 (m, 2H); 3.83-3.91 (m, 2H); 4.28-4.43 (m, 2H); 4.76-5.07 (m, 2H); 5.73*, 5.92 (s, 1H); 7.45-7.56 (m, 2H); 7.57-7.80 (m, 3H), 7.90 (d, 1H); 7.97-8.03 (m, 1H); 10.67*, 10.91 (s, 1H).

Example 40: Propan-2-yl 3-[4-({[2-acetyl-5-(methylsulfonyl)-2,3-dihydro-1H-isoindol-1- yl]carbonyl}amino)phenyl]-4,4,4-trifluoro-3-(trifluoromethyl)butanoate

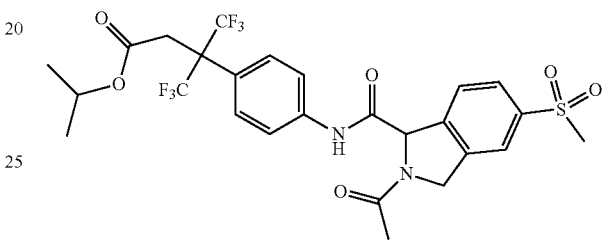

To a solution of 3-(4-(2-acetyl-5-(methylsulfonyl)isoindoline-1-carboxamido)phenyl)-4,4,4-trifluoro-3-(trifluoromethyl)butanoic acid (product of step 1 of the synthesis of Example 39, 35 mg, 0.06 mmol) in EtOAc (0.6 mL), propan-2-ol (93 mg, 1.54 mmol) was added, followed by Et$_3$N (0.026 mL, 0.19 mmol) and T3P (50% in EtOAc, 0.074 mL, 0.12 mmol). After the addition was completed the reaction mixture was stirred at rt for 1 h. The reaction mixture was partitioned between EtOAc (150 mL) and water (15 mL). The layers were separated in a phase separator. The organic layer was washed further with water (2×15 mL), dried over $Na_2SO_4$, filtered and the filtrate was concentrated in vacuo. The residue was dissolved in DMSO (1.5 mL), filtered and the filtrate was purified using SFC1-MS (chromatographic conditions: MeOH/NH$_3$ 20 mM; column: Waters BEH 5 μm 30×250 mm) to give 13 mg (35%) of the title compound.

HRMS: calculated for $(C_{26}H_{26}F_6N_2O_6S+H)^+$ 609.1494; found (ESI [M+H]$^+$) 609.1513. $^1$H NMR (600 MHz, DMSO-d$_6$, mixture of rotamers, 4*:1) δ 1.05-1.08 (m, 6H); 1.99, 2.15* (s, 3H); 3.21, 3.22* (s, 3H); 3.51*, 3.52 (s, 2H); 4.72-5.08 (m, 3H); 5.73*, 5.92 (s, 1H); 7.56-7.79 (m, 5H); 7.90 (dd, 1H); 7.98-8.04 (m, 1H); 10.69*, 10.93 (s, 1H).

Examples 41-44

Examples 41-44 (Table 3) were prepared using similar procedures to those described in examples 39 and 40.

Example 41: 2-Acetyl-5-(methylsulfonyl)-N-(4-{1,1,1-trifluoro-4-[(2-fluoroethyl)amino]-4-oxo-2-(trifluoromethyl)butan-2-yl}phenyl)-2,3-dihydro-1H-isoindole-1-carboxamide Example 42: 2-Acetyl-N-{4-[4-(dimethylamino)-1,1,1-trifluoro-4-oxo-2-(trifluoromethyl)butan-2-yl]phenyl}-5-(methylsulfonyl)-2,3-dihydro-1H-isoindole-1-carboxamide Example 43: 2-Acetyl-N-{4-[4-(tert-butylamino)-1,1,1-trifluoro-4-oxo-2-(trifluoromethyl)butan-2-yl]phenyl}-5-(methylsulfonyl)-2,3-dihydro-1H-isoindole-1-carboxamide Example 44: tert-Butyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate

TABLE 3

| Example No. | Structure | MS + NMR |
|---|---|---|
| 41 | 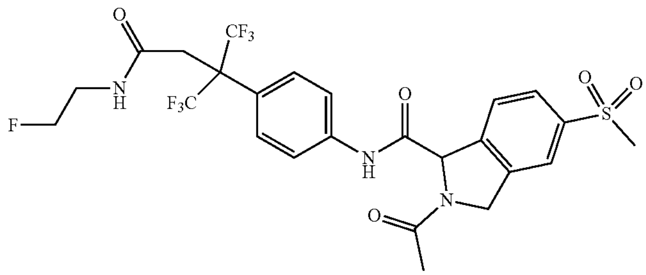 [SMILES: CC(=O)N1Cc2cc(S(C)(=O)=O)ccc2C1C(=O)Nc1ccc(C(CC(=O)NCCF)(C(F)(F)F)C(F)(F)F)cc1] | LC/MS: m/z = 610 [M − H]⁻.<br>¹H NMR (600 MHz, DMSO-d₆, mixture of rotamers, 4*:1) δ 1.99, 2.15* (s, 3H); 3.21, 3.22* (s, 3H); 3.28 (dq, 2H); 3.38*, 3.39 (s, 2H); 4.34 (dt, 2H); 4.78-5.07 (m, 2H); 5.72*, 5.93 (s, 1H); 7.57-7.79 (m, 5H); 7.90 (d, 1H); 7.97-8.06 (m, 1H); 8.48-8.51 (m, 1H); 10.67*, 10.90 (s, 1H). |
| 42 | 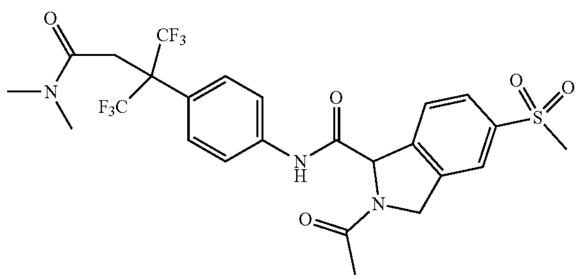 [SMILES: CC(=O)N1Cc2cc(S(C)(=O)=O)ccc2C1C(=O)Nc1ccc(C(CC(=O)N(C)C)(C(F)(F)F)C(F)(F)F)cc1] | HRMS: calculated for (C₂₅H₂₅F₆N₃O₅S + H)⁺<br>594.1497; found (ESI [M + H]⁺) 594.1480.<br>¹H NMR (600 MHz, DMSO-d₆, mixture of rotamers, 4*:1) δ 1.99, 2.15* (s, 3H); 2.75 (s, 3H); 3.09 (s, 3H); 3.21, 3.22* (s, 3H); 3.57*, 3.58 (s, 2H); 4.78-5.08 (m, 2H); 5.72*, 5.92 (s, 1H); 7.44-7.53 (m, 2H); 7.59-7.83 (m, 3H), 7.90 (d, 1H); 7.99*, 8.02 (s, 1H); 10.65*, 10.89 (s, 1H). |
| 43 | 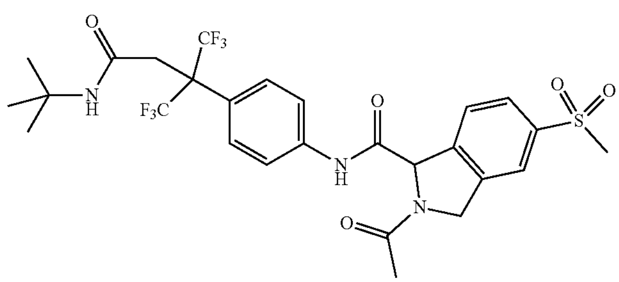 [SMILES: CC(=O)N1Cc2cc(S(C)(=O)=O)ccc2C1C(=O)Nc1ccc(C(CC(=O)NC(C)(C)C)(C(F)(F)F)C(F)(F)F)cc1] | LC/MS: m/z = 620 [M − H]⁻.<br>¹H NMR (600 MHz, DMSO-d₆, mixture of rotamers, 4*:1) δ 1.15 (s, 9H); 1.99, 2.15* (s, 3H); 3.20, 3.21* (s, 3H); 3.28*, 3.29 (s, 2H); 4.77-5.08 (m, 2H); 5.72*, 5.92 (s, 1H); 7.56-7.67 (m, 4H); 7.70 (d, 1H); 7.77*, 7.78 (s, 1H); 7.90 (d, 1H); 7.99*, 8.02 (s, 1H); 10.68*, 10.92 (s, 1H). |
| 44 | 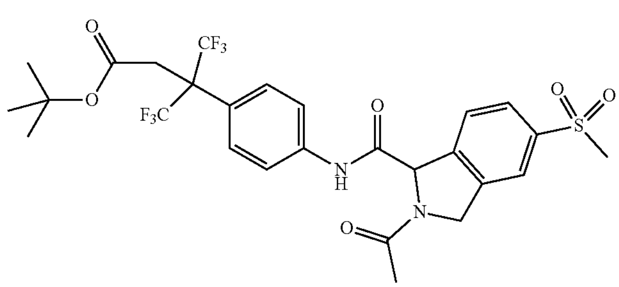 [SMILES: CC(=O)N1Cc2cc(S(C)(=O)=O)ccc2C1C(=O)Nc1ccc(C(CC(=O)OC(C)(C)C)(C(F)(F)F)C(F)(F)F)cc1] | HRMS: calculated for (C₂₇H₂₈F₆N₂O₆S + H)⁺<br>623.1650; found (ESI [M + H]⁺) 623.1693.<br>¹H NMR (600 MHz, DMSO-d₆, mixture of rotamers, 2*:1) δ 1.24*, 1.25 (s, 9H); 1.99, 2.15* (s, 3H); 3.21, 3.22* (s, 3H); 3.43*, 3.44 (s, 2H); 4.75-5.07 (m, 2H); 5.72*, 5.92 (s, 1H); 7.58-7.80 (m, 5H); 7.90 (d, 1H); 8.00*, 8.03 (s, 1H); 10.69*, 10.92 (s, 1H). |

Example 45: 2-Acetyl-N-{4-[4-(acetylamino)-1,1,1-trifluoro-2-(trifluoromethyl)butan-2-yl]phenyl}-5-(methylsulfonyl)-2,3-dihydro-1H-isoindole-1-carboxamide

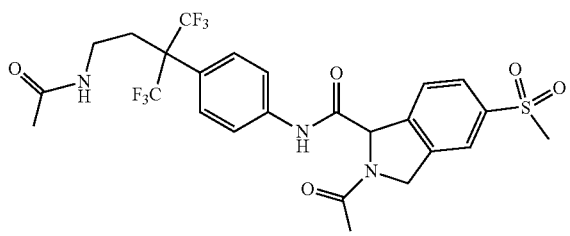 [SMILES: CC(=O)NCCC(c1ccc(NC(=O)C2c3ccc(S(C)(=O)=O)cc3CN2C(C)=O)cc1)(C(F)(F)F)C(F)(F)F]

Step 1: N-[4-[3-acetamido-1,1-bis(trifluoromethyl)propyl]phenyl]-5-methylsulfonyl-isoindoline-1-carboxamide

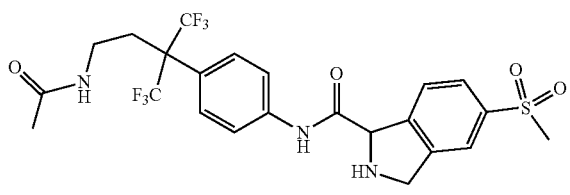 [SMILES: CC(=O)NCCC(c1ccc(NC(=O)C2NCc3cc(S(C)(=O)=O)ccc32)cc1)(C(F)(F)F)C(F)(F)F]

To a solution of tert-butyl 1-((4-(4-acetamido-1,1,1-trifluoro-2-(trifluoromethyl)butan-2-yl)phenyl)carbamoyl)-5-(methylsulfonyl)isoindoline-2-carboxylate (Intermediate 13, 99 mg, 0.15 mmol) in DCM (1.5 mL), TFA (0.5 mL, 6.49 mmol) was added and the resulting solution was stirred at rt for 1 h. The volatiles were removed in vacuo. The residue was dissolved in EtOAc (150 mL), washed with saturated aqueous NaHCO₃ solution (15 mL), dried over Na₂SO₄, filtered and the filtrate was concentrated in vacuo to give the title compound as a crude (80 mg, 95%) which was used in the next step without further purification.

LC/MS: m/z=552 [M+H]⁺.

Step 2: 2-Acetyl-N-{4-[4-(acetylamino)-1,1,1-trifluoro-2-(trifluoromethyl)butan-2-yl]phenyl}-5-(methylsulfonyl)-2,3-dihydro-1H-isoindole-1-carboxamide

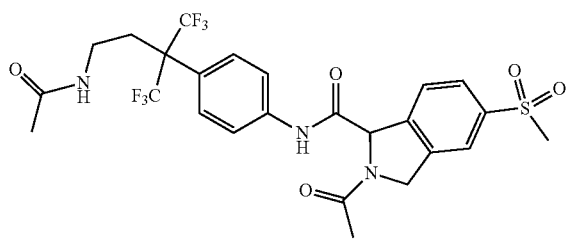 [SMILES: CC(=O)NCCC(c1ccc(NC(=O)C2c3ccc(S(C)(=O)=O)cc3CN2C(C)=O)cc1)(C(F)(F)F)C(F)(F)F]

To a solution of N-(4-(4-acetamido-1,1,1-trifluoro-2-(trifluoromethyl)butan-2-yl)phenyl)-5-(methylsulfonyl)isoindoline-1-carboxamide (product of step 1 of the synthesis of Example 45, 80 mg, 0.15 mmol) in pyridine (1 mL), Ac₂O (0.041 mL, 0.44 mmol) was added and the reaction mixture was stirred at rt for 1 h. The volatiles were removed in vacuo. The residue was dissolved in methanol (3 mL), concentrated in vacuo. This process was repeated for several times. The residue was dissolved in EtOAc (150 mL), washed with water (3×10 mL), dried over Na₂SO₄, filtered and the filtrate was concentrated in vacuo. The residue was dissolved in DMSO (2 mL), filtered and purified by SFC1-MS (chromatographic conditions: MeOH/NH₃ 20 mM, L; column: Phenomenex Luna Hilic 5μ 30×250 mm) to give 17.5 mg (98%) of the title compound.

HRMS: calculated for $(C_{25}H_{25}F_6N_3O_5S+H)^+$ 594.1497; found (ESI [M+H]⁺) 594.1510. ¹H NMR (500 MHz, DMSO-d₆, mixture of rotamers, 4*:1) δ 1.82 (s, 3H); 1.99, 2.15* (s, 3H); 2.47-2.51 (m, 2H); 2.97-3.08 (m, 2H); 3.21, 3.22* (s, 3H); 4.76-5.08 (m, 2H); 5.73*, 5.93 (s, 1H); 7.61-7.79 (m, 5H); 7.91 (d, 1H); 8.00*, 8.03 (s, 1H); 8.06 (t, 1H); 10.73*, 10.96 (s, 1H).

Biological Data

Compounds according to Formula I are RORγ modulators and their activities were determined in one of the following assays.

RORγ Radioligand Competition Binding Assay

The aim of this assay is to identify compounds which bind to the RORγ ligand binding domain, by competing with tritiated 2-(4-(ethylsulfonyl)phenyl)-N-(4-(2-(methoxymethyl)phenyl)thiophen-2-yl)acetamide.

Preparation of Tritiated 2-(4-(Ethylsulfonyl)phenyl)-N-(4-(2-(methoxymethyl)phenyl)thiophen-2-yl)acetamide

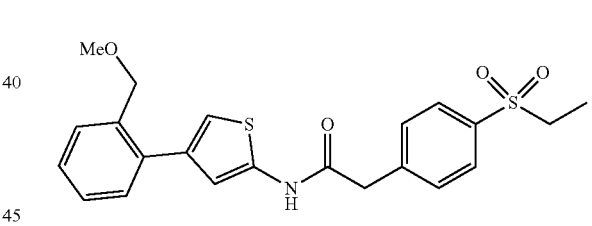

Step 1: N-(4-Bromothiophen-2-yl)-2-(4-(ethylsulfonyl)phenyl)acetamide

The trifluoroacetate salt of 4-bromothiophen-2-amine (2.45 g, 8.42 mmol, obtained by deprotection of tert-butyl N-(4-bromo-2-thienyl)carbamate with TFA in DCM) was added to 2-(4-(ethylsulfonyl)phenyl)acetic acid (2 g, 8.76 mmol), EDC (2.016 g, 10.51 mmol) and DMAP (3.21 g, 26.29 mmol) in DCM (30 mL) under nitrogen. The resulting mixture was stirred at rt for 12 h. The reaction mixture was diluted with EtOAc (100 mL), and washed sequentially with water (150 mL) and saturated brine (125 mL). The organic layer was dried over $Na_2SO_4$, filtered and evaporated to afford the crude product. The crude product was purified by flash silica chromatography, elution gradient 10% to 60% EtOAc in petroleum ether. Pure fractions were evaporated to dryness to afford N-(4-bromothiophen-2-yl)-2-(4-(ethylsulfonyl)phenyl)acetamide (2.0 g, 61%) as a solid. LC/MS: m/z=388, 390 [M+H]$^+$. $^1$H NMR (400 MHz, DMSO-d$_6$) δ 1.09, (t, 3H), 3.26 (q, 2H), 3.85 (s, 2H), 6.63 (d, 1H), 7.06, (d, 1H), 7.58 (d, 2H), 7.84 (d, 2H), 11.64 (s, 1H).

Step 2: 2-(4-(Ethylsulfonyl)phenyl)-N-(4-(2-(methoxymethyl)phenyl)thiophen-2-yl)acetamide

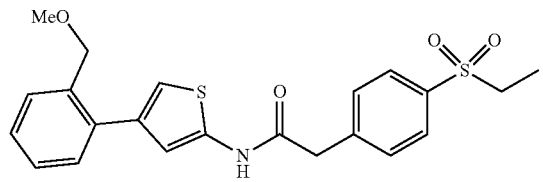 [SMILES: CCS(=O)(=O)c1ccc(CC(=O)Nc2cc(-c3ccccc3COC)cs2)cc1]

PdCl$_2$(dppf) (9.42 mg, 0.01 mmol) was added to N-(4-bromothiophen-2-yl)-2-(4-(ethylsulfonyl)phenyl)acetamide (100 mg, 0.26 mmol), (2-(methoxymethyl)phenyl)boronic acid (85 mg, 0.52 mmol) and K$_2$CO$_3$ (107 mg, 0.77 mmol) in 1,4-dioxane (4 mL) and water (0.5 mL) at 25° C. under nitrogen. The resulting mixture was stirred at 100° C. for 5 h. The reaction mixture was quenched with water (10 mL) and extracted with EtOAc (30×2 mL). The organic layer was dried over Na$_2$SO$_4$, filtered and evaporated to afford yellow solid. The crude product was purified by flash C18-flash chromatography, elution gradient 5 to 50% ACN in water. Pure fractions were evaporated to dryness to afford 2-(4-(ethylsulfonyl)phenyl)-N-(4-(2-(methoxymethyl)phenyl)thiophen-2-yl)acetamide (81 mg, 73.2%) as a solid.

HRMS: calculated for (C$_{22}$H$_{23}$NO$_4$S+H)$^+$ 430.1133; found: (ESI [M+H]$^+$) 430.1147. $^1$H NMR (300 MHz, CDCl$_3$) δ 1.29 (t, 3H), 3.11 (q, 2H), 3.38 (s, 3H), 3.82 (s, 2H), 4.38 (s, 2H), 6.80 (s, 1H), 6.92 (s, 1H), 7.28-7.39 (m, 3H), 7.43-7.47 (m, 1H), 7.51 (d, 2H), 7.85 (d, 2H), 8.35 (s, 1H).

Step 3: Tritiation of 2-(4-(ethylsulfonyl)phenyl)-N-(4-(2-(methoxymethyl)phenyl)thiophen-2-yl)acetamide 2-(4-(Ethylsulfonyl)phenyl)-N-(4-(2-(methoxymethyl)phenyl)thiophen-2-yl)acetamide (2.3 mg, 5.35 μmol) and 1-iodopyrrolidine-2,5-dione (1.3 mg, 5.78 μmol) were dissolved in DCM (0.2 mL) and TFA (0.02 mL) was added. The reaction mixture was stirred for 5 min, then concentrated by a stream of nitrogen. The residue was dissolved in EtOH (0.4 mL), triethylamine (20 μl, 144.28 μmol) was added and the solution was transferred to a tritiation vial containing Pd/C (3 mg, 2.82 μmol, 10% Pd). The vial was degassed by 3 freeze-pump-thaw-cycles. The flask was filled with T$_2$ gas (290 GBq). The reaction mixture was stirred at rt for 2.5 h. T$_2$ gas was recovered via the washing bed and the reaction mixture was concentrated by a stream of nitrogen. MeOH (0.7 mL) was added and the reaction mixture was concentrated by a stream of nitrogen. This procedure was repeated 3 times. The reaction mixture was filtered and dissolved in MeOH (15 mL total). After evaporation, the crude product was dissolved in DMSO and purified by preparative HPLC on a XBridge C18 column (10 μm, 250×19 mm) using a gradient of 5-95% ACN in H$_2$O/ACN/HOAc 95/5/0.5 buffer over 40 min with a flow of 15 mL/min. The product was detected by UV at 244 nm. Yield: 1717 MBq.

Protein Production

Human RORγ (Ligand Binding Domain (RORγ LBD) was expressed in *E. coli* (BL21DE3 Star) as a fusion protein: N-6×HN-Avi-GST-TCS-hRORγ LBD (S258-K518) subcloned into pET24a(+). The LBD (258-518) is underlined in the protein sequence:

(SEQ ID NO.: 1)
HNHNHNHNHNHNHNGGLNDIFEAQKIEWHEGSPILGYWKIKGLVQPTRLLLE

YLEEKYEEHLYERDEGDKWRNKKFELGLEFPNLPYYIDGDVKLTQSMAII

RYIADKHNMLGGCPKERAEISMLEGAVLDIRYGVSRIAYSKDFETLKVDF

LSKLPEMLKMFEDRLCHKTYLNGDHVTHPDFMLYDALDVVLYMDPMCLDA

FPKLVCFKKRIEAIPQIDKYLKSSKYIAWPLQGWQATFGGGDHPPKSDYD

IPTTGSGSGSLVPRGSTPEAPYASLTEIEHLVQSVCKSYRETCQLRLEDL

LRQRSNIFSREEVTGYQRKSMWEMWERCAHHLTEAIQYVVEFAKRLSGFM

ELCQNDQIVLLKAGAMEVVLVRMCRAYNADNRTVFFEGKYGGMELFRALG

CSELISSIFDFSHSLSALHFSEDEIALYTALVLINAHRPGLQEKRKVEQL

QYNLELAFHHHLCKTHRQSILAKLPPKGKLRSLCSQHVERLQIFQHLHPI

VVQAAFPPLYKELFSTETESPVGLSK.

The bacteria was grown in TB with Autoinduction media (Stock 50×ZYM-5052: 25% Glycerol, 2.5% Glucose, 10% Lactose), 3 mM MgOAc and 100 ug/ml Kan A. The culture was incubated at 180 rpm, at 37° C. At OD600 1.9, the temperature was decreased to 20° C. and at OD600 7.9 the cells were harvested. After centrifugation the bacterial pellet was resuspended in ice cold Lysis Buffer (20 mM Tris pH8.0, 250 mM NaCl, 10% (v/v) Glycerol, 0.5% CHAPS (w/v), 20 mM Imidazole, 1 mM TCEP, 1× Protease inhibitor (Complete, Roche), 1 μl Benzonase/100 ml buffer (E1014, Sigma)). Lysis was performed on ice at 30 kpsi using a Cell disruptor. To remove cell debris the sample was centrifuged at 48 000×g (20 000 rpm) for 20 min, at 4° C.

The protein was purified in two steps at rt. The 6×HN tag was utilized in the first affinity purification step where lysate was run over a HisTrap 5 ml Crude column (Amersham Pharmacia) using ÄKTA FPLC system (Amersham Pharmacia). After washing with Affinity purification buffer A (20 mM Tris pH8.0, 250 mM NaCl, 10% (v/v) Glycerol, 0.5% CHAPS (w/v), 20 mM Imidazole, 1 mM TCEP), proteins were eluted with a step gradient (50-100-150-200-250-300-500 mM Imidazole). Fractions of 0.5 ml volume were collected and analysed with SDS-PAGE (Novex system) and Coomassie staining. Fractions containing protein with expected molecular weight (from 50 mM Imidazole elution step) were pooled. The pool also contained protein with molecular weight corresponding to free GST. To separate GST from GST-RORγ a second size exclusion purification step was performed using a SEC Sephadex200 16/60 column (Amersham Pharmacia) at 0.8 ml/min in Size Exclusion/Storage Buffer (20 mM Tris pH8.0, 150 mM KCl, 0.5 mM EDTA, 20% (v/v) Glycerol, 0.5% (w/v) CHAPS, 1 mM TCEP). Fractions of 0.5 ml volume were collected and were analysed on a gel as described above. Fractions with no or low levels of the band corresponding to free GST, were pooled, frozen in liquid nitrogen and stored at −80° C. for use in the SPA binding assay.

Assay Protocol

The scintillation proximity assay (SPA) was run in white polystyrene flat-bottom 384-well plates (Greiner, cat. No. 781075). Assays were carried out in 40 µl reaction volumes. Various concentrations of test ligands in 0.4 microlitres of DMSO were added to assay plates using an acoustic liquid dispenser. 4 nM purified N-(HN)6-GST-TCS-hRORγ (258-518) was mixed with 40 micrograms Yttrium oxide (YOx) glutathione SPA imaging beads in assay buffer (20 mM Tris, 150 mM NaCl, 10% Glycerol, 0.25% CHAPS, 1 mM TCEP) prior to adding 30 microlitres to test ligands. Assay plates were incubated for one hour at room temperature before adding 10 microlitres tritiated 2-(4-(ethylsulfonyl)phenyl)-N-(4-(2-(methoxymethyl)phenyl)thiophen-2-yl)acetamide to test plates in assay buffer (final concentration, 25 nM). Test plates were incubated for 16 hours and read using a LEADseeker Multimodality imaging instrument.

The raw data was analysed and IC50 and Ki values for the compounds were calculated using Genedata Screener software. Raw data was transformed to % effect using equation 1:

Compound % effect=100*[(X−min)/(max−min)], where X represents the normalized value for the compound based on the Min (vehicle) and Max (reference compound) inhibition controls.

The concentration of test ligand that inhibited radioligand binding by 50% (i.e., the $IC_{50}$) was calculated by plotting the % effect versus test ligand concentration and fitting the data using the Genedata Screener Smart fit algorithm. $K_i$ is calculated from the $IC_{50}$ value using the equation Ki=IC50/ 1+[L]/Kd) where [L]=25 nmol/L and $K_d$=17 nmol/L RORγ Co-Factor Recruitment Assay A high throughput coactivator binding assay for the identification of inverse agonists of the recruitment of peptide SRC-1 (NCOA1_677-_700) to the RORγ ligand binding domain was established.

Protein Production

The ligand binding domain (LBD) of human RORγ was expressed in E. coli (BL21DE3 Star) as a fusion protein: N-6×HN-MBP-Avi-TCS-hRORγLBD(P260-K518) subcloned into pET24a(+). The LBD (P260-K518) is underlined in the protein sequence:

(SEQ ID NO.: 2)
MHNHNHNHNHNHNGGLNDIFEAQKIEWHEGMKIEEGKLVIWINGDKGYNG

LAEVGKKFEKDTGIKVTVEHPDKLEEKFPQVAATGDGPDIIFWAHDRFGG

YAQSGLLAEITPDKAFQDKLYPFTWDAVRYNGKLIAYPIAVEALSLIYNK

DLLPNPPKTWEEIPALDKELKAKGKSALMFNLQEPYFTWPLIAADGGYAF

KYENGKYDIKDVGVDNAGAKAGLTFLVDLIKNKHMNADTDYSIAEAAFNK

GETAMTINGPWAWSNIDTSKVNYGVTVLPTFKGQPSKPFVGVLSAGINAA

SPNKELAKEFLENYLLTDEGLEAVNKDKPLGAVALKSYEEELAKDPRIAA

TMENAQKGEIMPNIPQMSAFWYAVRTAVINAASGRQTVDEALKDAQTGSD

YDIPTTGSGSGSLVPRGST<u>PEAPYASLTEIEHLVQSVCKSYRETCQLRLE</u>

<u>DLLRQRSNIFSREEVTGYQRKSMWEMWERCAHHLTEAIQYVVEFAKRLSG</u>

<u>FMELCQNDQIVLLKAGAMEVVLVRMCRAYNADNRTVFFEGKYGGMELFRA</u>

<u>LGCSELISSIFDFSHSLSALHFSEDEIALYTALVLINAHRPGLQEKRKVE</u>

<u>QLQYNLELAFHHHLCKTHRQSILAKLPPKGKLRSLCSQHVERLQIFQHLH</u>

<u>PIVVQAAFPPLYKELFSTETESPVGLSK</u>.

Bacterial colonies were picked and inoculated in 16×500 mL TB medium supplemented with 25 mM $(NH_4)_2SO_4$, 50 mM $KH_2PO_4$, 50 mM $Na_2HPO_4$, 0.8% v/v Glycerol, 0.05% w/v Glucose, 0.2% w/v α-Lactose, 1 mM $MgSO_4$ and 200 µg/ml Kanamycin to promote autoinduction. After incubation at 37° C. at 200 rpm for two hours the temperature was decreased to 20° C. When the OD600 was 12.4, the temperature was further decreased to 16° C. Cells were harvested at OD600 24 by centrifugation at 4000 rpm for 10 min at 4° C. The pellet, approximately ~320 g was stored at −80° C.

The pellet was resuspended in 1600 mL Lysis Buffer (50 mM Tris-HCl, 10% v/v Glycerol, 1 mM TCEP, 2 tablets Protease Inhibitor/100 mL Lysis Buffer (Complete, Roche), 4 µl Benzonase/100 mL Lysis Buffer (E1014, Sigma), pH 8.0). Lysis was performed at 25 kpsi using Cell disruptor (Constant Cell Disruptor Systems). The sample was kept on ice during the whole lysis procedure. For removal of cell debris, the lysed cells were ultracentrifuged at 143719×g (43000 rpm) for 45 min at 4° C. The supernatant was stored at −80° C.

The thawed supernatant was captured utilizing the N-6× HN tag with washed 100 mL NiNTA Superflow resin (Qiagen) in Wash Buffer (50 mM Tris-HCl, 50 mM NaCl, 30 mM Imidazole, 10% v/v Glycerol, 1 mM TCEP, pH 8.0) and slowly stirred with a magnetic bar at rt. After 1.5 hours the supernatant was removed by vacuum suction through a porcelain funnel (sieve size 2). The resin, with the captured protein was washed with 700 mL Wash Buffer and transferred to three PD columns with filter (GE). Each column was eluted with 10 mL+90 mL Elution Buffer (50 mM Tris-HCl, 50 mM NaCl, 300 mM Imidazole, 10% v/v Glycerol, 1 mM TCEP, pH 8.0) and collected. All fractions from the columns were pooled and analysed with SDS-PAGE (Novex System) and stained in coomassie. The pooled sample was concentrated to ~30 mL using concentrators with 30K cutoff (Amicon, Millipore) at 4000 rpm and at 4° C. The concentrated sample was clarified at 30000×g for 15 min at 4° C. After centrifugation a small pellet of aggregated protein was visible which was discarded. In a size exclusion column (XK50/60, GE) 1000 mL Superdex 200 resin (GE) was equilibrated with GF Buffer (20 mM Tris-HCl, 150 mM NaCl, 10% v/v Glycerol, 1 mM TCEP, pH 8.0). The concentrated sample was loaded onto the column at the flow rate 6 mL/min and 14 mL fractions were collected. The fractions were analysed on a gel as described above. Fractions containing the major band which corresponded to the expected molecular weight for N-6×HN-MBP-Avi-TCS-hRORγLBD(P260-K518) (75.9 kDa) were collected and pooled. To further verify the mass, the pooled sample was analysed using mass spectrometry (Waters) and the mass corresponded to the expected mass. From 8 litres culture (~320 g bacteria cells) 348 mg of N-6×HN-MBP-Avi-TCS-hRORγLBD(P260-K518) was purified. Purified protein was flash frozen in liquid nitrogen and stored at −80° C.

Protein N-6×HN-MBP-Avi-TCS-hRORγLBD(P260-K518), 42 µM (223 mg) purified as described above was incubated with 15000 units BirA/µL (Avidity LLC) in 70 mL Biotinylation Buffer (200 µM Biotin, 10 mM ATP, 10 mM Mg$_2$OAc) at rt whilst slowly stirring with a magnetic bar for 9 hours. The reaction was analysed using mass spectrometry and the mass determined to be 76.2 kDa corresponding to biotinylated N-6×HN-MBP-Avi-TCS-hRORγLBD(P260-K518). After centrifugation at 19000 rpm for 15 min at 4° C. precipitation was visible which was discarded. The sample was concentrated as described above to ~25 mL. The reaction was polished in size exclusion columns (HiLoad Superdex 200 26/60, GE) equilibrated with GF Buffer using a flow rate of 2.5 mL/min and 2 mL/fractions were collected. The fractions were analysed on a gel as described above. Fractions containing the major band which corresponded to the expected molecular weight for biotinylated N-6×HN-MBP-Avi-TCS-hRORγ LBD(P260-K518) (76.2 kDa) were collected and pooled. The estimated yield was ~185 mg. Biotinylated protein was flash frozen in liquid nitrogen and stored at −80° C.

Assay Protocol

The assay was run in black 384 well plates (Greiner cat no: 784900). Various concentrations of test ligands in 0.1 microlitres DMSO were dispensed to assay plates using an Echo acoustic dispenser. Two pre-mixes were prepared and incubated for 1 h at room temp in the dark. Pre-mix 1 comprised 100 nM Protein (Biotinylated HN-Avi-MBP-TCS-hRORγ (258-518)) and 60 nM Streptavidin APC in assay buffer, 50 mM MOPS pH7.4, 50 mM KF, 0.003% (w/v) CHAPS, 10 mM DTT and 0.01% (w/v) BSA and pre-mix 2 comprised 160 nM biotinylated SRC-1 peptide (NCOA1-677-700) and 20 nM Europium-W8044 labelled Streptavidin in assay buffer. Five microlitres of pre-mix 2 was dispensed to assay plates containing 0.1 microlitres of test compound and was incubated for 15 min prior to adding five microlitres of pre-mix 1. Plates were incubated at rt for 1 hour in the dark, prior to reading in a Pherastar multi-mode plate reader using HTRF filter set (ex 320, em 612 and 665). The FRET signal at 665 nm was divided by the signal at 612 nm and multiplied by 10,000 to generate a signal ratio value for each well. The raw data was transformed to % effect using the equation:

Compound % effect=100*[(X−min)/(max−min)], where X represents the normalized value for the compound based on the Min (vehicle) and Max (reference compound) inhibition control.

The concentration of test ligand that inhibited the activity by 50% (i.e., the IC$_{50}$) was calculated by plotting the % effect versus test ligand concentration and fitting the data using the Genedata Screener Smart fit algorithm.

Inhibition of IL-17 Release from Human T$_H$17 Cells

This test is designed to screen compounds for their inhibitory effect on the release of IL-17 from isolated and cultured human T$_H$17 cells.

Peripheral blood mononuclear cells (PBMC) were isolated from heparin treated human whole blood from healthy donors by density gradient centrifugation. T$_H$17 cells (CD4+ CXCR3−CCR6+) were enriched using a human T$_H$17 Cell Enrichment Kit (Stemcell Technologies) according to the manufacturer's protocol. The isolated T$_H$17 cells were activated with aCD3aCD28 beads (MACS Miltenyi) and cultured in X-Vivo15 medium (Lonza) supplemented with L-glutamine, β-mercaptoethanol and a cytokine cocktail consisting of; IL-2, IL-23, IL-1β, IL-6, TGF-β. Cells were seeded at 8000 cells/well in a 384-plate (Corning, #3707) in the presence of compounds or DMSO and cultured for 4 days (37° C., 5% CO$_2$). On day 4 supernatants were collected and IL-17A was measured using a Human IL-17 HTRF Assay kit (Cisbio Bioassays) according to the manufacturer's protocol. The IC$_{50}$ values for the tested compounds was calculated using Genedata Screener® software (Genedata) using the following calculation method;

Compound % effect=100*[(X−min)/(max−min)], where X represents the normalized value for the compound based on the Min (DMSO) and Max (compound 3-(1,3-benzodioxol-5-yl)-1-(3,5-dimethylpiperidin-1-yl)-3-(2-hydroxy-4,6-dimethoxyphenyl)propan-1-one at 10 µM, described in J. R. Hu et al. ACS Med. Chem. Lett. 2013, 4, 79-84) inhibition controls.

Results

All exemplified compounds were tested in the FRET assay described above. All of the exemplified compounds were also tested in the SPA assay. Selected compounds were further characterized for the inhibition of Il-17 release in the cell assay. Results are summarized in the table below.

TABLE 5

Screening results of exemplified compounds

| Example No. | pIC$_{50}$ (FRET) | pIC$_{50}$ (SPA) | pIC$_{50}$ IL-17 release |
|---|---|---|---|
| 1 | 6.9 | 6.7 | 7.0 |
| 2 | 6.9 | 7.8 | 8.0 |
| 3 | 6.6 | 7.7 | 7.8 |
| 4 | 7.2 | 7.9 | 8.1 |
| 5 | 7.3 | 7.9 | 8.0 |
| 6 | 7.4 | 8.0 | — |
| 7 | 7.3 | 7.9 | — |
| 8 | 7.3 | 7.9 | — |
| 9 | 7.0 | 8.0 | — |
| 10 | 7.1 | 7.6 | — |
| 11 | 6.8 | 7.6 | — |
| 12 | 7.0 | 8.1 | 7.6 |
| 13 | 7.2 | 8.2 | 8.3 |
| 14 | 7.4 | 8.3 | 8.6 |
| 15 | 7.4 | 8.3 | 8.4 |
| 16 | 7.4 | 8.2 | — |
| 17 | 7.0 | 7.5 | 7.7 |
| 18 | 6.7 | 7.3 | 7.6 |
| 19 | 7.0 | 6.9 | 7.3 |
| 20 | 7.0 | 7.0 | 7.3 |
| 21 | 6.9 | 6.5 | 7.0 |
| 22 | 6.0 | 6.0 | 6.1 |
| 23 | 7.4 | 7.7 | 7.8 |
| 24 | 7.3 | 7.5 | — |
| 25 | 7.4 | 8.2 | — |
| 26 | 6.0 | 6.2 | — |
| 27 | <4.5 | 8.1 | — |
| 28 | 7.4 | 8.1 | — |
| 29 | 7.0 | 7.4 | — |
| 30 | 6.9 | 7.4 | 7.6 |
| 31 | 6.7 | 6.1 | 6.7 |
| 32 | 7.3 | 7.6 | 7.8 |
| 33 | 6.8 | 6.6 | 6.7 |
| 34 | 6.9 | 7.7 | 7.7 |
| 35 | 7.4 | 8.0 | 8.2 |
| 36 | 7.0 | 6.8 | 7.2 |
| 37 | 7.0 | 7.8 | 7.6 |
| 38 | 6.2 | 6.1 | 6.0 |
| 39 | <4.5 | 6.4 | — |
| 40 | <4.5 | 7.9 | — |
| 41 | 6.5 | 6.1 | <5.5 |
| 42 | 6.5 | 6.1 | 6.1 |
| 43 | 6.8 | 6.1 | 6.6 |
| 44 | <4.5 | 7.8 | — |
| 45 | 6.7 | 6.1 | 5.5 |

The invention claimed is:

1. A compound of formula (I):

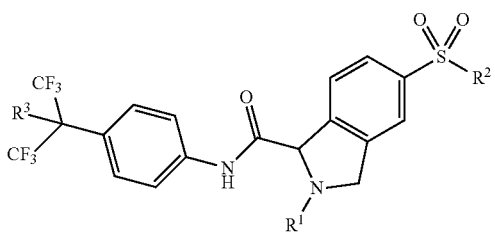

wherein:
$R^1$ is H, (CO)$R^4$ or (CO)NH—$C_{1-6}$ alkyl;
$R^2$ is $C_{1-6}$ alkyl or $CH_2$-cyclopropyl;
$R^3$ is $C_{1-6}$ alkyl, $C_{1-6}$ alkoxy, CN, heterocycloalkyl, heteroaryl, $NR^5R^6$, $CH_2(CO)$—O—$C_{1-6}$ alkyl, $CH_2(CO)NR^7R^8$, wherein said $C_{1-6}$ alkyl is further optionally substituted with one substituent selected from OH, halo, CN, heteroaryl, or NH(CO)Me, and wherein each heteroaryl is further optionally substituted with one methyl group;
$R^4$ is:
H;
$C_{1-6}$ alkyl optionally substituted with one substituent selected from OH, $C_{1-6}$ alkoxy, COOH or $N_2$;
$C_{3-7}$ cycloalkyl optionally substituted with $C_{1-6}$ alkoxy; or
$C_{1-6}$ alkoxy;
$R^5$ is H or $C_{1-6}$ alkyl;
$R^6$ is $C_{1-6}$ alkyl or heterocycloalkyl, wherein said $C_{1-6}$ alkyl is further optionally substituted with one substituent selected from OH, $C_{1-6}$ alkoxy, $C_{3-7}$ cycloalkyl (itself optionally substituted by $C_{1-6}$ alkoxy) or $SO_2$Me;
$R^7$ is H or $C_{1-6}$ alkyl;
$R^8$ is $C_{3-7}$ cycloalkyl or $C_{1-6}$ alkyl wherein said $C_{1-6}$ alkyl is further optionally substituted with halo; or
$R^7$ and $R^8$ together with the nitrogen atom to which they are both attached form a heterocycloalkyl (itself optionally substituted with one or two substituents selected from $C_{1-6}$ alkyl or halo);
or a pharmaceutically acceptable salt thereof.

2. A compound of formula (I) according to claim 1, or a pharmaceutically acceptable salt thereof, wherein
$R^1$ is (CO)$R^4$ or (CO)NH—$C_{1-6}$ alkyl;
$R^2$ is $C_{1-6}$ alkyl or $CH_2$-cyclopropyl;
$R^3$ is $C_{1-6}$ alkoxy, CN or heterocycloalkyl; and
$R^4$ is:
$C_{1-6}$ alkyl optionally substituted with OH; or
$C_{1-6}$ alkoxy.

3. A compound of formula (I) according to claim 1, or a pharmaceutically acceptable salt thereof, wherein $R^1$ is (CO)$R^4$.

4. A compound of formula (I) according to claim 1, or a pharmaceutically acceptable salt thereof, wherein $R^4$ is unsubstituted $C_{1-6}$ alkyl.

5. A compound of formula (I) according to claim 1, or a pharmaceutically acceptable salt thereof, wherein $R^2$ is unsubstituted $C_{1-6}$ alkyl.

6. A compound of formula (I) according to claim 1, or a pharmaceutically acceptable salt thereof, wherein $R^3$ is CN.

7. A compound according to claim 1 selected from:
N-[4-(2-Cyano-1,1,1,3,3,3-hexafluoropropan-2-yl)phenyl]-5-(methylsulfonyl)-2,3-dihydro-1H-isoindole-1-carboxamide;
2-Acetyl-N-[4-(2-cyano-1,1,1,3,3,3-hexafluoropropan-2-yl)phenyl]-5-(methylsulfonyl)-2,3-dihydro-1H-isoindole-1-carboxamide;
N-[4-(2-Cyano-1,1,1,3,3,3-hexafluoropropan-2-yl)phenyl]-2-[(1-methoxycyclopropyl)carbonyl]-5-(methylsulfonyl)-2,3-dihydro-1H-isoindole-1-carboxamide;
N'-[4-(2-Cyano-1,1,1,3,3,3-hexafluoropropan-2-yl)phenyl]-$N^2$-methyl-5-(methylsulfonyl)-1,3-dihydro-2H-isoindole-1,2-dicarboxamide;
N-[4-(2-Cyano-1,1,1,3,3,3-hexafluoropropan-2-yl)phenyl]-2-(hydroxyacetyl)-5-(methylsulfonyl)-2,3-dihydro-1H-isoindole-1-carboxamide;
N-[4-(2-Cyano-1,1,1,3,3,3-hexafluoropropan-2-yl)phenyl]-2-formyl-5-(methylsulfonyl)-2,3-dihydro-1H-isoindole-1-carboxamide;
Methyl 1-{[4-(2-cyano-1,1,1,3,3,3-hexafluoropropan-2-yl)phenyl]carbamoyl}-5-(methylsulfonyl)-1,3-dihydro-2H-isoindole-2-carboxylate;
N-[4-(2-Cyano-1,1,1,3,3,3-hexafluoropropan-2-yl)phenyl]-2-(methoxyacetyl)-5-(methylsulfonyl)-2,3-dihydro-1H-isoindole-1-carboxamide;
4-[1-{[4-(2-Cyano-1,1,1,3,3,3-hexafluoropropan-2-yl)phenyl]carbamoyl}-5-(methyl sulfonyl)-1,3-dihydro-2H-isoindol-2-yl]-4-oxobutanoic acid;
N-[4-(2-Cyano-1,1,1,3,3,3-hexafluoropropan-2-yl)phenyl]-2-glycyl-5-(methylsulfonyl)-2,3-dihydro-1H-isoindole-1-carboxamide;
2-(3-Aminopropanoyl)-N-[-4-[1-cyano-2,2,2-trifluoro-1-(trifluoromethyl)ethyl]phenyl]-5-methylsulfonyl-isoindoline-1-carboxamide;
N-[4-(2-Cyano-1,1,1,3,3,3-hexafluoropropan-2-yl)phenyl]-5-[(cyclopropylmethyl)sulfonyl]-2,3-dihydro-1H-isoindole-1-carboxamide;
2-Acetyl-N-[4-(2-cyano-1,1,1,3,3,3-hexafluoropropan-2-yl)phenyl]-5-[(cyclopropylmethyl)sulfonyl]-2,3-dihydro-1H-isoindole-1-carboxamide;
2-Acetyl-N-[4-(2-cyano-1,1,1,3,3,3-hexafluoropropan-2-yl)phenyl]-5-(ethylsulfonyl)-2,3-dihydro-1H-isoindole-1-carboxamide;
2-Acetyl-N-{4-[1,1,1,3,3,3-hexafluoro-2-(pyrrolidin-1-yl)propan-2-yl]phenyl}-5-(methyl sulfonyl)-2,3-dihydro-1H-isoindole-1-carboxamide;

2-Acetyl-N-{4-[1,1,1,3,3,3-hexafluoro-2-(propylamino) propan-2-yl]phenyl}-5-(methyl sulfonyl)-2,3-dihydro-1H-isoindole-1-carboxamide;

2-Acetyl-N-(4-{1,1,1,3,3,3-hexafluoro-2-[(2-methoxyethyl)amino]propan-2-yl}phenyl)-5-(methyl sulfonyl)-2,3-dihydro-1H-isoindole-1-carboxamide;

2-Acetyl-N-[4-(1,1,1,3,3,3-hexafluoro-2-{[(1-methoxycyclopropyl)methyl]amino}propan-2-yl)phenyl]-5-(methyl sulfonyl)-2,3-dihydro-1H-isoindole-1-carboxamide;

2-Acetyl-N-{4-[1,1,1,3,3,3-hexafluoro-2-(oxetan-3-ylamino)propan-2-yl]phenyl}-5-(methyl sulfonyl)-2,3-dihydro-1H-isoindole-1-carboxamide;

2-Acetyl-N-{4-[1,1,1,3,3,3-hexafluoro-2-(tetrahydro-2H-pyran-4-ylamino)propan-2-yl]phenyl}-5-(methyl sulfonyl)-2,3-dihydro-1H-isoindole-1carboxamide;

2-Acetyl-N-(4-{1,1,1,3,3,3-hexafluoro-2-[(2-hydroxyethyl)amino]propan-2-yl}phenyl)-5-(methyl sulfonyl)-2,3-dihydro-1H-isoindole-1-carboxamide;

2-Acetyl-N-[4-(1,1,1,3,3,3-hexafluoro-2-{[3-(methylsulfonyl)propyl]amino}propan-2-yl)phenyl]-5-(methylsulfonyl)-2,3-dihydro-1H-isoindole-1-carboxamide;

2-Acetyl-N-{4-[1,1,1,3,3,3-hexafluoro-2-(morpholin-4-yl)propan-2-yl]phenyl}-5-(methyl sulfonyl)-2,3-dihydro-1H-isoindole-1-carboxamide;

2-Acetyl-N-{4-[1,1,1,3,3,3-hexafluoro-2-(methylamino)propan-2-yl]phenyl}-5-(methylsulfonyl)-2,3-dihydro-1H-isoindole-1-carboxamide;

2-Acetyl-N-{4-[2-(dimethylamino)-1,1,1,3,3,3-hexafluoropropan-2-yl]phenyl}-5-(methylsulfonyl)-2,3-dihydro-1H-isoindole-1-carboxamide;

2-Acetyl-N-[4-(1,1,1,3,3,3-hexafluoro-2-{[2-(methylsulfonyl)ethyl]amino}propan-2-yl)phenyl]-5-(methylsulfonyl)-2,3-dihydro-1H-isoindole-1-carboxamide;

2-Acetyl-N-[4-(1,1,1,3,3,3-hexafluoro-2-{[2-(propan-2-yloxy)ethyl]amino}propan-2-yl)phenyl]-5-(methylsulfonyl)-2,3-dihydro-1H-isoindole-1-carboxamide;

2-Acetyl-N-[4-(1,1,1,3,3,3-hexafluoro-2-methoxypropan-2-yl)phenyl]-5-(methylsulfonyl)-2,3-dihydro-1H-isoindole-1-carboxamide;

2-Acetyl-N-{4-[1,1,1,3,3,3-hexafluoro-2-(1H-1,2,3-triazol-1-yl)propan-2-yl]phenyl}-5-(methylsulfonyl)-2,3-dihydro-1H-isoindole-1-carboxamide;

2-Acetyl-N-{4-[1,1,1,3,3,3-hexafluoro-2-(2-methyl-2H-tetrazol-5-yl)propan-2-yl]phenyl}-5-(methylsulfonyl)-2,3-dihydro-1H-isoindole-1-carboxamide;

Methyl 4,4,4-trifluoro-3-[4-[(5-methylsulfonylisoindoline-1-carbonyl)amino]phenyl]-3-(trifluoromethyl)butanoate;

Methyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate;

2-Acetyl-5-(methylsulfonyl)-N-{4-[1,1,1-trifluoro-4-hydroxy-2-(trifluoromethyl)butan-2-yl]phenyl}-2,3-dihydro-1H-isoindole-1-carboxamide;

2-Acetyl-N-(4-{1,1,1,3,3,3-hexafluoro-2-[(3-methyl-1,2,4-oxadiazol-5-yl)methyl]propan-2-yl}phenyl)-5-(methylsulfonyl)-2,3-dihydro-1H-isoindole-1-carboxamide;

2-Acetyl-5-(methylsulfonyl)-N-{4-[1,1,1,4-tetrafluoro-2-(trifluoromethyl)butan-2-yl]phenyl}-2,3-dihydro-1H-isoindole-1-carboxamide;

2-Acetyl-N-{4-[2-(cyanomethyl)-1,1,1,3,3,3-hexafluoropropan-2-yl]phenyl}-5-(methylsulfonyl)-2,3-dihydro-1H-isoindole-1-carboxamide;

Ethyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate;

2-Acetyl-N-{4-[4-(cyclopropylamino)-1,1,1-trifluoro-4-oxo-2-(trifluoromethyl)butan-2-yl]phenyl}-5-(methylsulfonyl)-2,3-dihydro-1H-isoindole-1-carboxamide;

2-Acetyl-5-(methylsulfonyl)-N-{4-[1,1,1-trifluoro-4-(3-fluoro-3-methylazetidin-1-yl)-4-oxo-2-(trifluoromethyl)butan-2-yl]phenyl}-2,3-dihydro-1H-isoindole-1-carboxamide;

Propan-2-yl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate;

2-Acetyl-5-(methylsulfonyl)-N-(4-{1,1,-trifluoro-4-[(2-fluoroethyl)amino]-4-oxo-2-(trifluoromethyl)butan-2-yl}phenyl)-2,3-dihydro-1H-isoindole-1-carboxamide;

2-Acetyl-N-{4-[4-(dimethylamino)-1,1,1-trifluoro-4-oxo-2-(trifluoromethyl)butan-2-yl]phenyl}-5-(methylsulfonyl)-2,3-dihydro-1H-isoindole-1-carboxamide;

2-Acetyl-N-{4-[4-(tert-butylamino)-1,1,1-trifluoro-4-oxo-2-(trifluoromethyl)butan-2-yl]phenyl}-5-(methylsulfonyl)-2,3-dihydro-1H-isoindole-1-carboxamide;

tert-Butyl 3-[4-({[2-acetyl-5-(methylsulfonyl)-2,3-dihydro-1H-isoindol-1-yl]carbonyl}amino)phenyl]-4,4,4-trifluoro-3-(trifluoromethyl)butanoate; and 2-Acetyl-N-{4-[4-(acetylamino)-1,1,1-trifluoro-2-(trifluoromethyl)butan-2-yl]phenyl}-5-(methylsulfonyl)-2,3-dihydro-1H-isoindole-1-carboxamide or a pharmaceutically acceptable salt thereof.

8. A compound according to claim 1 selected from:

2-Acetyl-N-[4-(2-cyano-1,1,1,3,3,3-hexafluoropropan-2-yl)phenyl]-5-(methylsulfonyl)-2,3-dihydro-1H-isoindole-1-carboxamide;

$N^1$-[4-(2-Cyano-1,1,1,3,3,3-hexafluoropropan-2-yl)phenyl]-$N^2$-methyl-5-(methylsulfonyl)-1,3-dihydro-2H-isoindole-1,2-dicarboxamide;

N-[4-(2-Cyano-1,1,1,3,3,3-hexafluoropropan-2-yl)phenyl]-2-(hydroxyacetyl)-5-(methylsulfonyl)-2,3-dihydro-1H-isoindole-1-carboxamide;

Methyl 1-{[4-(2-cyano-1,1,1,3,3,3-hexafluoropropan-2-yl)phenyl]carbamoyl}-5-(methylsulfonyl)-1,3-dihydro-2H-isoindole-2-carboxylate;

2-Acetyl-N-[4-(2-cyano-1,1,1,3,3,3-hexafluoropropan-2-yl)phenyl]-5-[(cyclopropylmethyl)sulfonyl]-2,3-dihydro-1H-isoindole-1-carboxamide;

2-Acetyl-N-[4-(2-cyano-1,1,1,3,3,3-hexafluoropropan-2-yl)phenyl]-5-(ethylsulfonyl)-2,3-dihydro-1H-isoindole-1-carboxamide;

2-Acetyl-N-{4-[1,1,1,3,3,3-hexafluoro-2-(pyrrolidin-1-yl)propan-2-yl]phenyl}-5-(methylsulfonyl)-2,3-dihydro-1H-isoindole-1-carboxamide; and 2-Acetyl-N-[4-(1,1,1,3,3,3-hexafluoro-2-methoxypropan-2-yl)phenyl]-5-(methylsulfonyl)-2,3-dihydro-1H-isoindole-1-carboxamide;

or a pharmaceutically acceptable salt thereof.

9. A pharmaceutical composition which comprises a compound, or a pharmaceutically acceptable salt thereof, as claimed in any one of claims 1 to 8, and one or more pharmaceutically acceptable excipients.

10. A pharmaceutical composition comprising a compound, or a pharmaceutically acceptable salt thereof, as claimed in any one of claims 1 to 8, and at least one active ingredient selected from:

(a) a beta-adrenoceptor agonist;
(b) a muscarinic receptor antagonist;
(c) a joint muscarinic receptor antagonist and beta-adrenoceptor agonist; and (d) a glucocorticoid receptor agonist (steroidal or non-steroidal).

11. A method of treating chronic obstructive pulmonary disease (COPD), asthma, ankylosing spondylitis, psoriatic arthritis or psoriasis in a warm-blooded animal, which comprises administering to a mammal in need of such treatment a therapeutically effective amount of a compound of formula (I), or a pharmaceutically acceptable salt thereof, as claimed in any one of claims 1 to 8.

12. A method of treating psoriasis in a mammal suffering from, or at risk of, said disease, which comprises administering to a mammal in need of such treatment a therapeutically effective amount of a compound of formula (I), or a pharmaceutically acceptable salt thereof, as claimed in any one of claims 1 to 8.

* * * * *

SEQUENCE LISTING

<160> NUMBER OF SEQ ID NOS: 2

<210> SEQ ID NO 1
<211> LENGTH: 526
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| His | Asn | His | Asn | His | Asn | His | Asn | His | Asn | His | Asn | Gly | Gly | Leu | Asn |
| 1 | | | | 5 | | | | | 10 | | | | | 15 | |
| Asp | Ile | Phe | Glu | Ala | Gln | Lys | Ile | Glu | Trp | His | Glu | Gly | Ser | Pro | Ile |
| | | | 20 | | | | | 25 | | | | | 30 | | |
| Leu | Gly | Tyr | Trp | Lys | Ile | Lys | Gly | Leu | Val | Gln | Pro | Thr | Arg | Leu | Leu |
| | | | 35 | | | | | 40 | | | | | 45 | | |
| Leu | Glu | Tyr | Leu | Glu | Glu | Lys | Tyr | Glu | Glu | His | Leu | Tyr | Glu | Arg | Asp |
| | | | 50 | | | | | 55 | | | | | 60 | | |
| Glu | Gly | Asp | Lys | Trp | Arg | Asn | Lys | Lys | Phe | Glu | Leu | Gly | Leu | Glu | Phe |
| 65 | | | | 70 | | | | | 75 | | | | | 80 | |
| Pro | Asn | Leu | Pro | Tyr | Tyr | Ile | Asp | Gly | Asp | Val | Lys | Leu | Thr | Gln | Ser |
| | | | | 85 | | | | | 90 | | | | | 95 | |
| Met | Ala | Ile | Ile | Arg | Tyr | Ile | Ala | Asp | Lys | His | Asn | Met | Leu | Gly | Gly |
| | | | 100 | | | | | 105 | | | | | 110 | | |
| Cys | Pro | Lys | Glu | Arg | Ala | Glu | Ile | Ser | Met | Leu | Glu | Gly | Ala | Val | Leu |
| | | | 115 | | | | | 120 | | | | | 125 | | |
| Asp | Ile | Arg | Tyr | Gly | Val | Ser | Arg | Ile | Ala | Tyr | Ser | Lys | Asp | Phe | Glu |
| | | 130 | | | | | 135 | | | | | 140 | | | |
| Thr | Leu | Lys | Val | Asp | Phe | Leu | Ser | Lys | Leu | Pro | Glu | Met | Leu | Lys | Met |
| 145 | | | | | 150 | | | | | 155 | | | | | 160 |
| Phe | Glu | Asp | Arg | Leu | Cys | His | Lys | Thr | Tyr | Leu | Asn | Gly | Asp | His | Val |
| | | | | 165 | | | | | 170 | | | | | 175 | |
| Thr | His | Pro | Asp | Phe | Met | Leu | Tyr | Asp | Ala | Leu | Asp | Val | Val | Leu | Tyr |
| | | | 180 | | | | | 185 | | | | | 190 | | |
| Met | Asp | Pro | Met | Cys | Leu | Asp | Ala | Phe | Pro | Lys | Leu | Val | Cys | Phe | Lys |
| | | | 195 | | | | | 200 | | | | | 205 | | |
| Lys | Arg | Ile | Glu | Ala | Ile | Pro | Gln | Ile | Asp | Lys | Tyr | Leu | Lys | Ser | Ser |
| | | 210 | | | | | 215 | | | | | 220 | | | |
| Lys | Tyr | Ile | Ala | Trp | Pro | Leu | Gln | Gly | Trp | Gln | Ala | Thr | Phe | Gly | Gly |
| 225 | | | | | 230 | | | | | 235 | | | | | 240 |
| Gly | Asp | His | Pro | Pro | Lys | Ser | Asp | Tyr | Asp | Ile | Pro | Thr | Thr | Gly | Ser |
| | | | | 245 | | | | | 250 | | | | | 255 | |
| Gly | Ser | Gly | Ser | Leu | Val | Pro | Arg | Gly | Ser | Thr | Pro | Glu | Ala | Pro | Tyr |
| | | | 260 | | | | | 265 | | | | | 270 | | |
| Ala | Ser | Leu | Thr | Glu | Ile | Glu | His | Leu | Val | Gln | Ser | Val | Cys | Lys | Ser |
| | | | 275 | | | | | 280 | | | | | 285 | | |
| Tyr | Arg | Glu | Thr | Cys | Gln | Leu | Arg | Leu | Glu | Asp | Leu | Leu | Arg | Gln | Arg |
| | | 290 | | | | | 295 | | | | | 300 | | | |
| Ser | Asn | Ile | Phe | Ser | Arg | Glu | Glu | Val | Thr | Gly | Tyr | Gln | Arg | Lys | Ser |
| 305 | | | | | 310 | | | | | 315 | | | | | 320 |
| Met | Trp | Glu | Met | Trp | Glu | Arg | Cys | Ala | His | His | Leu | Thr | Glu | Ala | Ile |
| | | | | 325 | | | | | 330 | | | | | 335 | |
| Gln | Tyr | Val | Val | Glu | Phe | Ala | Lys | Arg | Leu | Ser | Gly | Phe | Met | Glu | Leu |
| | | | 340 | | | | | 345 | | | | | 350 | | |
| Cys | Gln | Asn | Asp | Gln | Ile | Val | Leu | Leu | Lys | Ala | Gly | Ala | Met | Glu | Val |
| | | | 355 | | | | | 360 | | | | | 365 | | |

```
Val Leu Val Arg Met Cys Arg Ala Tyr Asn Ala Asp Asn Arg Thr Val
    370                 375                 380

Phe Phe Glu Gly Lys Tyr Gly Gly Met Glu Leu Phe Arg Ala Leu Gly
385                 390                 395                 400

Cys Ser Glu Leu Ile Ser Ser Ile Phe Asp Phe Ser His Ser Leu Ser
                405                 410                 415

Ala Leu His Phe Ser Glu Asp Glu Ile Ala Leu Tyr Thr Ala Leu Val
            420                 425                 430

Leu Ile Asn Ala His Arg Pro Gly Leu Gln Glu Lys Arg Lys Val Glu
        435                 440                 445

Gln Leu Gln Tyr Asn Leu Glu Leu Ala Phe His His Leu Cys Lys
    450                 455                 460

Thr His Arg Gln Ser Ile Leu Ala Lys Leu Pro Pro Lys Gly Lys Leu
465                 470                 475                 480

Arg Ser Leu Cys Ser Gln His Val Glu Arg Leu Gln Ile Phe Gln His
                485                 490                 495

Leu His Pro Ile Val Val Gln Ala Ala Phe Pro Pro Leu Tyr Lys Glu
            500                 505                 510

Leu Phe Ser Thr Glu Thr Glu Ser Pro Val Gly Leu Ser Lys
    515                 520                 525

<210> SEQ ID NO 2
<211> LENGTH: 678
<212> TYPE: PRT
<213> ORGANISM: Homo sapiens

<400> SEQUENCE: 2

Met His Asn His Asn His Asn His Asn His Asn Gly Gly Leu
1               5                   10                  15

Asn Asp Ile Phe Glu Ala Gln Lys Ile Glu Trp His Glu Gly Met Lys
                20                  25                  30

Ile Glu Glu Gly Lys Leu Val Ile Trp Ile Asn Gly Asp Lys Gly Tyr
            35                  40                  45

Asn Gly Leu Ala Glu Val Gly Lys Lys Phe Glu Lys Asp Thr Gly Ile
        50                  55                  60

Lys Val Thr Val Glu His Pro Asp Lys Leu Glu Glu Lys Phe Pro Gln
65                  70                  75                  80

Val Ala Ala Thr Gly Asp Gly Pro Asp Ile Ile Phe Trp Ala His Asp
                85                  90                  95

Arg Phe Gly Gly Tyr Ala Gln Ser Gly Leu Leu Ala Glu Ile Thr Pro
            100                 105                 110

Asp Lys Ala Phe Gln Asp Lys Leu Tyr Pro Phe Thr Trp Asp Ala Val
        115                 120                 125

Arg Tyr Asn Gly Lys Leu Ile Ala Tyr Pro Ile Ala Val Glu Ala Leu
    130                 135                 140

Ser Leu Ile Tyr Asn Lys Asp Leu Leu Pro Asn Pro Lys Thr Trp
145                 150                 155                 160

Glu Glu Ile Pro Ala Leu Asp Lys Glu Leu Lys Ala Lys Gly Lys Ser
                165                 170                 175

Ala Leu Met Phe Asn Leu Gln Glu Pro Tyr Phe Thr Trp Pro Leu Ile
            180                 185                 190

Ala Ala Asp Gly Gly Tyr Ala Phe Lys Tyr Glu Asn Gly Lys Tyr Asp
        195                 200                 205

Ile Lys Asp Val Gly Val Asp Asn Ala Gly Ala Lys Ala Gly Leu Thr
    210                 215                 220
```

```
Phe Leu Val Asp Leu Ile Lys Asn Lys His Met Asn Ala Asp Thr Asp
225                 230                 235                 240

Tyr Ser Ile Ala Glu Ala Ala Phe Asn Lys Gly Glu Thr Ala Met Thr
            245                 250                 255

Ile Asn Gly Pro Trp Ala Trp Ser Asn Ile Asp Thr Ser Lys Val Asn
                260                 265                 270

Tyr Gly Val Thr Val Leu Pro Thr Phe Lys Gly Gln Pro Ser Lys Pro
            275                 280                 285

Phe Val Gly Val Leu Ser Ala Gly Ile Asn Ala Ala Ser Pro Asn Lys
290                 295                 300

Glu Leu Ala Lys Glu Phe Leu Glu Asn Tyr Leu Leu Thr Asp Glu Gly
305                 310                 315                 320

Leu Glu Ala Val Asn Lys Asp Lys Pro Leu Gly Ala Val Ala Leu Lys
                325                 330                 335

Ser Tyr Glu Glu Leu Ala Lys Asp Pro Arg Ile Ala Ala Thr Met
                340                 345                 350

Glu Asn Ala Gln Lys Gly Glu Ile Met Pro Asn Ile Pro Gln Met Ser
            355                 360                 365

Ala Phe Trp Tyr Ala Val Arg Thr Ala Val Ile Asn Ala Ala Ser Gly
370                 375                 380

Arg Gln Thr Val Asp Glu Ala Leu Lys Asp Ala Gln Thr Gly Ser Asp
385                 390                 395                 400

Tyr Asp Ile Pro Thr Thr Gly Ser Gly Ser Gly Ser Leu Val Pro Arg
                405                 410                 415

Gly Ser Thr Pro Glu Ala Pro Tyr Ala Ser Leu Thr Glu Ile Glu His
            420                 425                 430

Leu Val Gln Ser Val Cys Lys Ser Tyr Arg Glu Thr Cys Gln Leu Arg
            435                 440                 445

Leu Glu Asp Leu Leu Arg Gln Arg Ser Asn Ile Phe Ser Arg Glu Glu
            450                 455                 460

Val Thr Gly Tyr Gln Arg Lys Ser Met Trp Glu Met Trp Glu Arg Cys
465                 470                 475                 480

Ala His His Leu Thr Glu Ala Ile Gln Tyr Val Val Glu Phe Ala Lys
                485                 490                 495

Arg Leu Ser Gly Phe Met Glu Leu Cys Gln Asn Asp Gln Ile Val Leu
                500                 505                 510

Leu Lys Ala Gly Ala Met Glu Val Val Leu Val Arg Met Cys Arg Ala
            515                 520                 525

Tyr Asn Ala Asp Asn Arg Thr Val Phe Phe Glu Gly Lys Tyr Gly Gly
            530                 535                 540

Met Glu Leu Phe Arg Ala Leu Gly Cys Ser Glu Leu Ile Ser Ser Ile
545                 550                 555                 560

Phe Asp Phe Ser His Ser Leu Ser Ala Leu His Phe Ser Glu Asp Glu
                565                 570                 575

Ile Ala Leu Tyr Thr Ala Leu Val Leu Ile Asn Ala His Arg Pro Gly
                580                 585                 590

Leu Gln Glu Lys Arg Lys Val Glu Gln Leu Gln Tyr Asn Leu Glu Leu
            595                 600                 605

Ala Phe His His His Leu Cys Lys Thr His Arg Gln Ser Ile Leu Ala
            610                 615                 620

Lys Leu Pro Pro Lys Gly Lys Leu Arg Ser Leu Cys Ser Gln His Val
625                 630                 635                 640
```

```
Glu Arg Leu Gln Ile Phe Gln His Leu His Pro Ile Val Val Gln Ala
                645                 650                 655

Ala Phe Pro Pro Leu Tyr Lys Glu Leu Phe Ser Thr Glu Thr Glu Ser
                660                 665                 670

Pro Val Gly Leu Ser Lys
                675
```